US009409963B2

(12) United States Patent
Soo et al.

(10) Patent No.: US 9,409,963 B2
(45) Date of Patent: Aug. 9, 2016

(54) FIBROMODULIN PEPTIDE

(75) Inventors: B. Chia Soo, Beverly Hills, CA (US);
Kang Ting, Beverly Hills, CA (US);
Zhong Zheng, Van Nuys, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/322,124

(22) PCT Filed: May 26, 2010

(86) PCT No.: PCT/US2010/036262
§ 371 (c)(1),
(2), (4) Date: Mar. 14, 2012

(87) PCT Pub. No.: WO2010/138637
PCT Pub. Date: Dec. 2, 2010

(65) Prior Publication Data
US 2012/0171253 A1 Jul. 5, 2012

Related U.S. Application Data

(60) Provisional application No. 61/181,226, filed on May 26, 2009.

(51) Int. Cl.
*A61K 38/16* (2006.01)
*C07K 14/47* (2006.01)
*A61K 38/18* (2006.01)

(52) U.S. Cl.
CPC ......... *C07K 14/4725* (2013.01); *A61K 38/1841* (2013.01); *C07K 2319/02* (2013.01); *C07K 2319/21* (2013.01)

(58) Field of Classification Search
CPC .......................... A61K 38/00; A61K 38/1841
See application file for complete search history.

(56) References Cited

U.S. PATENT DOCUMENTS 5,654,270 A 8/1997 Longaker et al.

FOREIGN PATENT DOCUMENTS

WO WO 96-25178 8/1996
WO WO 2004/099784 11/2004

OTHER PUBLICATIONS

Hildebrand et al., "Interaction of the small interstitial proteoglycans biglycan, decorin and fibromodulin with transforming growth factor β", Biochem. J. vol. 302, pp. 527-534 (1994).
Honardoust et al., "Localization of small leucine-rich proteoglycans and transforming growth factor-beta in human oral mucosal wound healing", Wound Rep. Reg. vol. 16, pp. 814-823 (2008).
Soo et al. "Differential expression of fibromodulin, a transforming growth factor-β modulator, in fetal skin development and scarless repair", Am J. of Pathol. vol. 157, No. 2, pp. 423-433 (2000).
Supplemental European Search Report mailed Oct. 2, 2012, 2 pages.
Ebner, R., Chen, R.H., Lawler, S., Zioncheck, T. & Derynck, R. Determination of Type-I Receptor Specificity by the Type-II Receptors for TGF-Beta or Activin. *Science* 262, 900-902 (1993).
Brandes, M.E., Mai, U.E., Ohura, K. & Wahl, S.M. Type I transforming growth factor-beta receptors on neutrophils mediate chemotaxis to transforming growth factor-beta. *J Immunol* 147, 1600-6 (1991).
De Crescenzo, G., Pham, P.L., Durocher, Y. & O'Connor-McCourt, M.D. Transforming growth factor-beta (TGF-beta) binding to the extracellular domain of the type II TGF-beta receptor: receptor capture on a biosensor surface using a new coiled-coil capture system demonstrates that avidity contributes significantly to high affinity binding. *J Mol Biol* 328, 1173-83 (2003).
Cui, W. et al. Concerted action of TGF-beta 1 and its type II receptor in control of epidermal homeostasis in transgenic mice. *Genes Dev* 9, 945-55 (1995).
Lopez-Casillas, F. et al. Structure and expression of the membrane proteoglycan betaglycan, a component of the TGF-beta receptor system. *Cell* 67, 785-795 (1991).
Lopez-Casillas, F., Payne, H.M., Andres, J.L. & Massague, J. Betaglycan Can Act as a Dual Modulator of TGF-Beta Access to Signaling Receptors—Mapping of Ligand-Binding and Gag Attachment Sites. *Journal of Cell Biology* 124, 557-568 (1994).
Boucher, P. et al. LRP1 Functions as an Atheroprotective Integrator of TGF beta and PDGF Signals in the Vascular Wall: Implications for Marfan Syndrome. *Plos One* 2(2007).
Baghy, K., Iozzo, R.V. & Kovalszky, I. Decorin-TGF beta Axis in Hepatic Fibrosis and Cirrhosis. *Journal of Histochemistry & Cytochemistry* 60, 262-268 (2012).
Hildebrand, A. et al. Interaction of the small interstitial proteoglycans biglycan, decorin and fibromodulin with transforming growth factor β. *Biochem J* 302, 527-534 (1994).
Annes, J.P., Chen, Y., Munger, J.S. & Rifkin, D.B. Integrin alpha(v)beta(6)-mediated activation of latent TGF-beta requires the latent TGF-beta binding protein-1. *Journal of Cell Biology* 165, 723-734 (2004).
Hyytiainen, M., Penttinen, C. & Keski-Oja, J. Latent TGF-beta binding proteins: Extracellular matrix association and roles in TGF-beta activation. *Critical Reviews in Clinical Laboratory Sciences* 41, 233-264 (2004).
Keski-Oja, J. et al. Latent Tgf-Beta Binding Proteins (Ltbps) in Targeting TGF-Beta Action. *Anticancer Research* 28, 3345-3346 (2008).
Todorovic, V. et al. Latent TGF-beta binding proteins. *International Journal of Biochemistry & Cell Biology* 37, 38-41 (2005).
Vehvilainen, P. et al. Latent TGF-beta binding proteins (LTBPs) 1 and 3 differentially regulate transforming growth factor-beta activity in malignant mesothelioma. *Human Pathology* 42, 269-278 (2011).
Philip, A., Bostedt, L., Stigbrand, T. & Oconnormccourt, M.D. Binding of Transforming Growth-Factor-Beta (Tgf-Beta) to Pregnancy Zone Protein (Pzp)—Comparison to the Tgf-Beta-Alpha(2)-Macroglobulin Interaction. *European Journal of Biochemistry* 221, 687-693 (1994).
Lastres, P. et al. Endoglin modulates cellular responses to TGF-beta 1. *Journal of Cell Biology* 133, 1109-1121 (1996).
Mooradian, D.L., Lucas, R.C., Weatherbee, J.A. & Furcht, L.T. Transforming Growth Factor-Beta-1 Binds to Immobilized Fibronectin. *Journal of Cellular Biochemistry* 41, 189-200 (1989).

*Primary Examiner* — Prema Mertz
(74) *Attorney, Agent, or Firm* — Duane Morris LLP

(57) ABSTRACT

Embodiments of the present invention provide a fibromodulin (FMOD) peptide (FMOD-P), a composition and a formulation comprising a FMOD-P, option-ally with a TGF-β isoform, or comprising FMOD with a TGF-β isoform. The present invention also provides methods of making and using the FMOD-P, composition, or formulation.

8 Claims, 23 Drawing Sheets

```
REMARK query     DPRDCPQECDCPPNFPTAMYCDNRRLKYLPF-VPSRMKYYFQNNQITSIQEGVFDNATGLLWIALEGNQITSDKVGRKV  SEQ ID NO:67
REMARK 1xec_A    -GPVCFFRDXC----HLKYYQKSDLGLEKVPKDLPPDTALLDLQRKKITEIKDGDFKKLENLHTLILINNEISK---ISPGA  SEQ ID NO:68
REMARK ACCI      -+663222134----685411311114386128712653113111121615413741135161411311216156--23621
REMARK SS_QP     CCCCCCCCCCCCCCCEEEBCCCCCCCCCC--CCCCCEEEECCCCCCEECHHHCCCCCEEECCCEEEECCCCHHH
REMARK SS        -CCCCCCCCEE----ECCEEEECCCCCCCCCCCCCCCEEEECCCCCCEECCCCCCCCCEEECCCCCE--ECCCC
REMARK
REMARK query     PSKLRHLERLYLDHQQLTRMPGPLPRSLRELHLDHNQISRVPNVALEGLEDLTALYLHNKIQE----YGSSMRGLRSLIL  SEQ ID NO:67
REMARK 1xec_A    FAPLVKLERLYLSENQLKELPEKMPKTLQELRVHENEITKVBKSVFNGLKQMIVVELGTNPLKSSGIENGAPQQMKLSY  SEQ ID NO:68
REMARK ACCI      16418513311112136511361163132111141413183411544443111113161639214711141178131
REMARK SS_QP     HHCCCCEEEECCCCCCCCCCCCCCCCEEEECCCCCEEEECCCCCHBBCCCCCCCEEECCCCCCC----CCHHBHCCCCCCCE
REMARK SS        CCCCCCCCEEECCCCCCCCCCCCCCCCEECCCCCCEEEECCCCHHHCCCCCCCEEECCCCCCHHHCCCCCCCCCCCCE
REMARK
REMARK query     LDLSYNHLRKVPDGLPSALEQLYMEHNHVYTNPDSYFRGAPKLLYVRLSHNSLTPNGLASNTPNS5SLLELILSYNQLQK  SEQ ID NO:67
REMARK 1xec_A    IRIADTNITTIPQGLPPSLTELHLGGKEITKVDAASLEGLNRLAKLGLSPNSIGAVDNGSLA-NTPHLRELHLNNNKLVR  SEQ ID NO:68
REMARK ACCI      11115141441144118313211112153441223811761351221112613154248511S-2144142111316158
REMARK SS_QP     EECCCCCCCCCCCCCCCCCCEEEECCCEEEEEECHHHCCCCCCCCCCCCEEECCCCCCCEEEECCCCCCCCCCC
REMARK SS        EEECCCCCCCCCCCCCCEEECCCCCCEECCCCCCCCCCCEEECCCCCCEECCCCCHH-BCCCCCEEECCCCCCC
REMARK
REMARK query     IPPVK----TRLERLYLQGNRIKEFSISSSFCTVVDVYNFSKLQVLRLDGNEIKRSAMPADAPLCLRLASLIEI     SEQ ID NO:67
REMARK 1xec_A    VPGGLADHKYIQVVYLRNNKISAIGSNDFCPPGYNTKRASYSGVGLFSNPYGYWEIQPSTFRCVYVRAAVQL     SEQ ID NO:68
REMARK ACCI      118441271451311312416614653111947498134161111361418775189412212668811S5
REMARK SS_QP     CCCCC----CCCCEEEECCCCCCEECCCCCCCCCCCCCCCCEEECCCCEECCCCCHHHCCCCCCCEEEC
REMARK SS        CCCCCCCCCCCCEEECCCCCCCCCCCCCCCCCCCCCCCEEECCCCCCHHHCCHHHCCCCCHHHHEEC
```

Figure 5

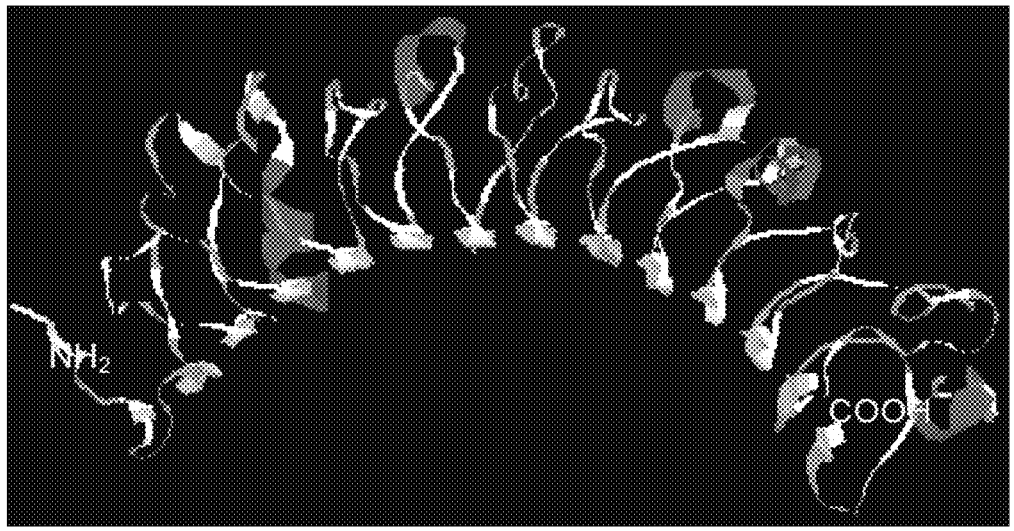

Figure 6

FIBROMODULIN PEPTIDE

CROSS-REFERENCE TO THE RELATED APPLICATIONS

This application is a national phase application under 35 U.S.C. §371(c) of International Application No. PCT/US10/36262, filed on May 26, 2010, which claims the benefit of U.S. provisional application Ser. No. 61/181,226, filed on May 26, 2009.

TECHNICAL FIELD OF THE INVENTION

The present invention generally relates to fibromodulin and a peptide thereof and methods of making and using the same.

BACKGROUND OF THE INVENTION

Fibromodulin (FMOD) is a member of small leucine rich proteoglycan (SLRP) family. Fibromodulin is a cytosolic secreted protein with an expression pattern restricted mainly to cartilage, bone, connective tissue, and tissue rich in collagen (Heinegard, Larsson et al. 1986). Fibromodulin is involved in fibrillogenesis, cell adhesion, and cytokine activity modulation (Yamaguchi, Mann et al. 1990; Hildebrand, Romaris et al. 1994). Previous studies shown that FMOD can combine with both transforming growth factor (TGF)-$\beta$ isoforms and collagens (Hedbom and Heinegard 1989; Hildebrand, Romaris et al. 1994) to modulate the extracellular matrix. TGF-$\beta$ is a profibrotic factor that increases fibroblast proliferation, stimulates the synthesis and deposition of connective tissue, and inhibits connective tissue breakdown (Gharaee-Kermani, Hu et al. 2009). Kalamajski and Oldberg reported that FMOD binds type I collagen via glu-353 and lys-355 in leucine-rich repeat 11 locates in the C-terminal of the protein (Kalamajski and Oldberg 2007). Svensson et al., have reported that FMOD functions in the assembly of the collagen network in connective tissues and that mice lacking a functional fibromodulin gene exhibit an altered morphological phenotype in tail tendon with fewer and abnormal collagen fiber bundles (Svensson, Aszodi et al. 1999).

It is an objective of the present invention to generate a FMOD-P that binds TGF-$\beta$ and modulates in vitro TGF-$\beta$ activity. It is another objective of the present invention to provide a composition for treating, preventing, or ameliorating a body condition by modulating TGF-$\beta$ activities and/or collagen assembly.

SUMMARY OF THE INVENTION

According to one aspect of the invention, it is provided a fibromodulin (FMOD) peptide (FMOD-P) comprising at least one site capable of binding to beta-tissue growth factor (TGF-$\beta$). In some embodiments, the FMOD-P has an amino acid sequence that may be selected from, but not limited to, the group consisting of SEQ ID NO:13, SEQ ID NO:14, SEQ ID NO:15, SEQ ID NO:16, SEQ ID NO:17, SEQ ID NO:18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, and SEQ ID NO:63.

According to another aspect of the present invention, it is provided a composition. The composition comprises an effective amount of any of the following ingredients:
a) a FMOD-P;
b) a combination of FMOD-P;
c) a FMOD-P or a combination of FMOD-P and at least one TGF-$\beta$ isoform;
d) FMOD and at least one TGF-$\beta$ isoform;
e) FMOD and a FMOD-P or a combination of FMOD-P; and
f) any combination of (a)-(e),
wherein the composition is effective for modulating activities of TGF-$\beta$ and/or collagen assembly.

In some embodiments, the FMOD-P has an amino acid sequence that may be selected from, but not limited to, the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, and SEQ ID NO:63.

In some embodiments, the TGF-$\beta$ isoform can be one of TGF-$\beta$1, TGF-$\beta$2, and TGF-$\beta$3.

In some further embodiments, the composition further comprises an excipient. In some embodiment, the excipient is a pharmaceutically acceptable carrier or dermatologically acceptable carrier.

The composition disclosed herein can be a formulated for systemic or local delivery. In some embodiments, local delivery is topical delivery, transdermal delivery, intradermal delivery, microneedle delivery, delivery as a coating on medical devices (e.g., cardiovascular stents, breast implants), or delivery by impregnating or coating on various scaffold devices (e.g., allograft dermis, Integra dermal regeneration template). In some further embodiments, systemic delivery is injection, oral administration, nasal delivery, or inhalation.

According to a further aspect of the present invention, it is provided a method of making a FMOD-P. The method comprises:
designing a FMOD-P having the function and at least one binding site of FMOD, and
preparing the FMOD-P.

In some embodiments, preparing comprises splicing FMOD at one or more selected sites to generate the FMOD-P.

In some embodiments, preparing comprises expressing the FMOD-P in a recombinant system e.g., expressing the FMOD-P in a bacterial, yeast, mammalian, or plant cell.

In some embodiments, preparing comprises synthesizing the FMOD-P using peptide synthesizer machines.

In some embodiments, designing comprises hydrophobic analysis of a primary or secondary structure of FMOD.

According to a further aspect of the present invention, it is provided a method of making a composition. The method comprises:

providing an ingredient selected from any of the following:
a) a FMOD-P;
b) a combination of FMOD-P;
c) a FMOD-P or a combination of FMOD-P and at least one TGF-β isoform;
d) FMOD and at least one TGF-β isoform;
e) FMOD and a FMOD-P or a combination of FMOD-P; and
f) any combination of (a)-(e), and
forming a composition comprising any of ingredients (a)-(f).

In some embodiments, the step forming further comprises: providing an excipient, and forming a formulation comprising the ingredient and the excipient.

According to a still further aspect of the present invention, it is provided a method of treating, preventing, or ameliorating a body condition. The method comprises administering to a subject:
a FMOD-P disclosed herein;
a composition disclosed herein; or
a formulation disclosed herein.

In some embodiments, the body condition can be excessive fibrosis or scar formation that are associated with high TGF-β expression, hypertrophic scars, keloids, radiation fibrosis, and fibrotic conditions in organ systems other than skin. In some embodiments, such fibrotic conditions include pulmonary fibrosis or a liver, kidney, cornea, intra-abdominal, gastrointestinal, urological, neurological, or cardiovascular condition.

BRIEF DESCRIPTION OF THE DRAWINGS

FIG. 5 shows structural alignment between human FMOD (query: SEQ ID NO:67) and the template (1xec_A: SEQ ID NO:68). ACCI value indicated the relative solvent accessibility of each residue of the template, from low to high: *, 1, 2, 3, 4, 5, 6, 7, 8, 9; SS and SS_QP indicated the known secondary structure of the template and predicted secondary structure of the FMOD, respectively; H: helix, E: sheet, and C: coil.

FIG. 6 shows the predicted 3D structure of recombinant human FMOD (AA 71-375). Yellow: sheet; red: helix; blue and white: coil.

leucine-rich repeat (LRR). Some invention FMOD peptides were designed from the primary structure of human FMOD.

Figure 12:
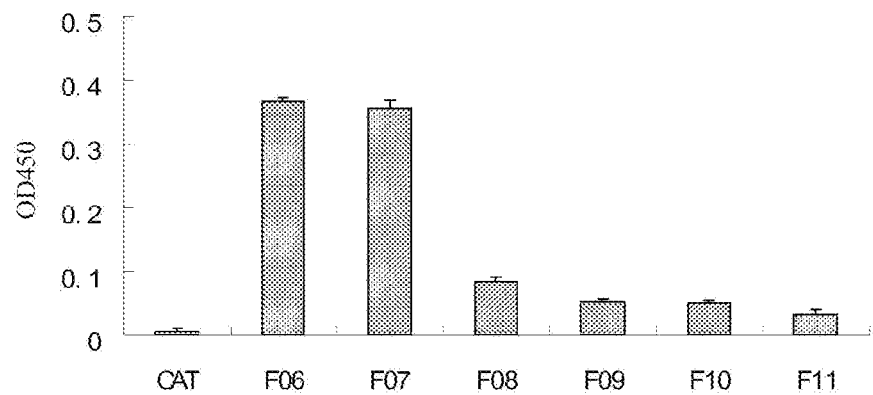

FIG. 12 shows the ELISA analysis of some of the SUMO-fused FMOD peptide fragments binding with TGF-β1.

Figure 13:
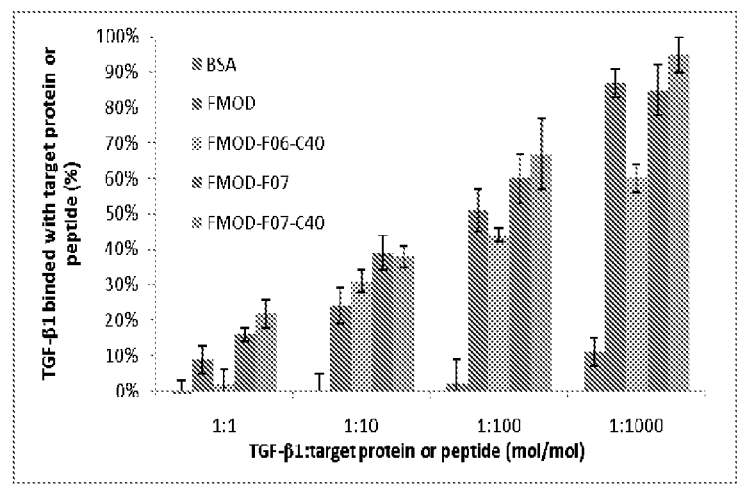

FIG. 13 shows the binding activity of TGF-β1 to FMOD and/or FMOD-P.

Figure 14:
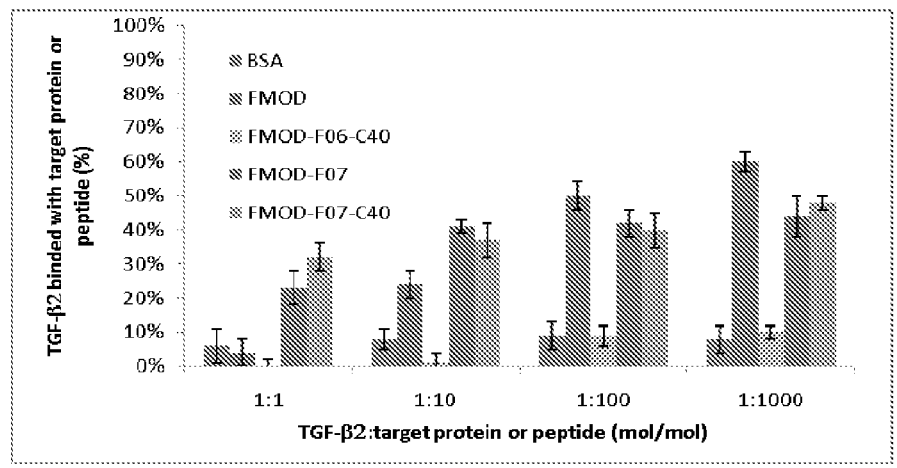

FIG. 14 shows the binding activity of TGF-β2 to FMOD and/or FMOD-P.

Figure 15:
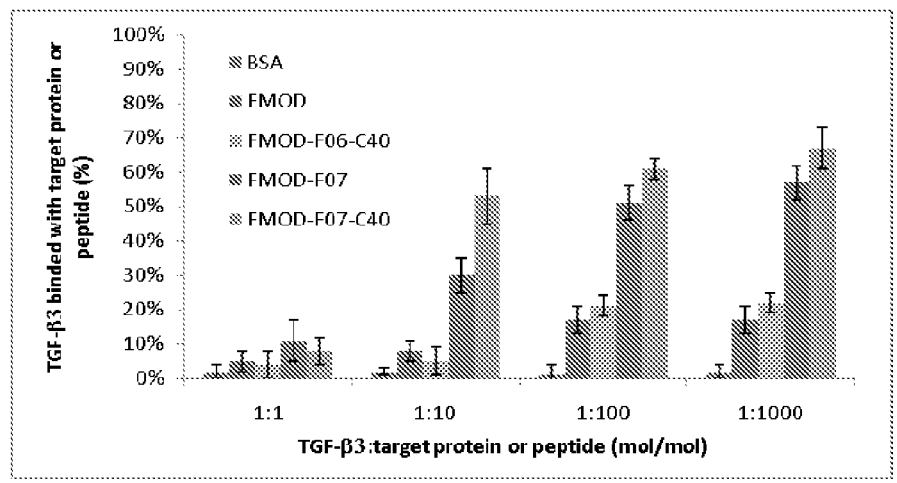

FIG. 15 shows the binding activity of TGF-β3 to FMOD and/or FMOD-P.

Figure 16:
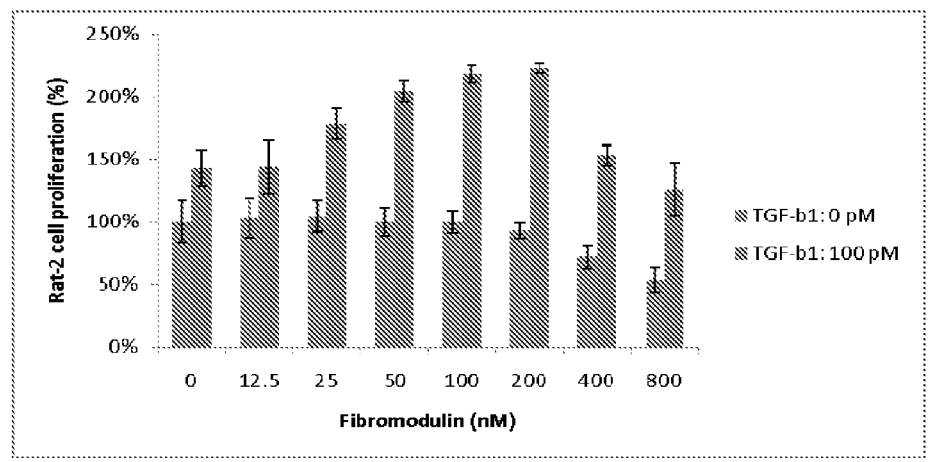

FIG. 16 shows the effect of TGF-β combined with FMOD on cell proliferation

Figure 17A:
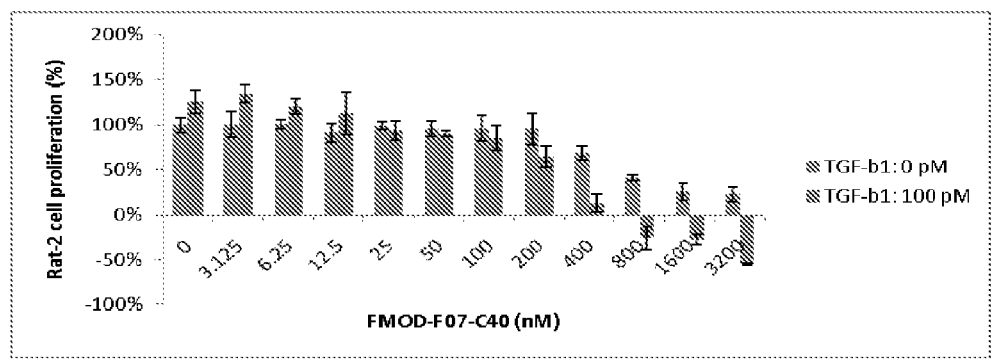
Figure 17B:
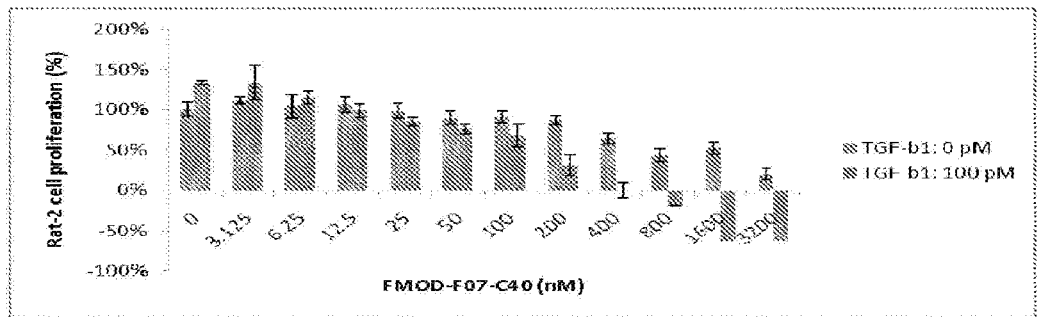

FIGS. 17A and 17B show the effect of TGF-β combined with F07-C40 on cell proliferation.

Figure 17C:
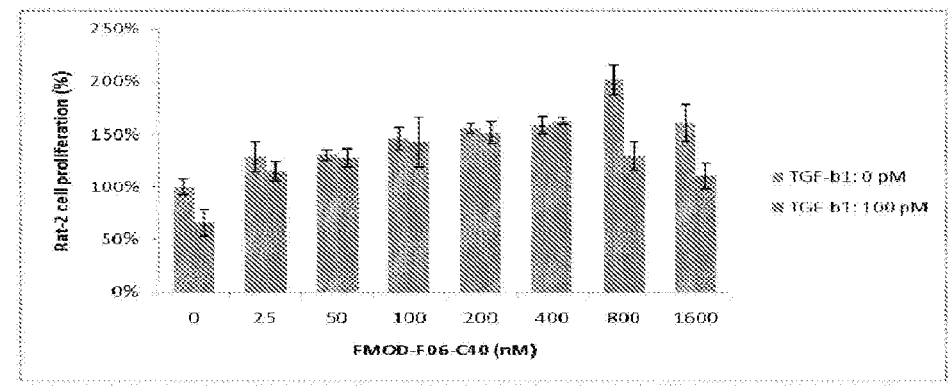

FIG. 17C shows the effect of TGF-β combined with F06-C40 on cell proliferation.

FIGS. 18A-18D shows the results of a few examples of tests on the effect of FMOD and/or TGF-β on cell migration.

FIGS. 19A-19D show test results of cell migration/invasion in Matrigel at 200× magnificent after 24 hour treatment and quantitated using DAPI nuclear staining.

FIGS. 20A-20E show test results of cell migration/invasion in Matrigel at 100× magnificent after 24 hour treatment and quantitated using DAPI nuclear staining.

FIGS. 21A-21D show results of tests on the effect of FMOD and TGF-β or FMOD peptides and TGF-β on connective tissue growth factor (CTGF) expression and cell aggregation.

Figure 22:
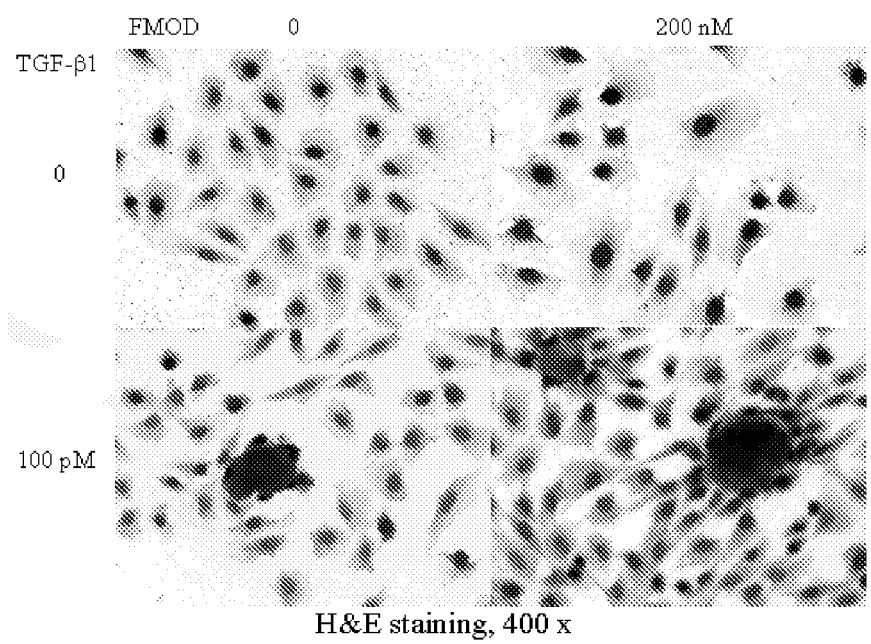

FIG. 22 shows the results on H&E morphology of Rat-2 cells after FMOD, TGF-131, or FMOD and TGF-β1 treatment.

Figure 23A:
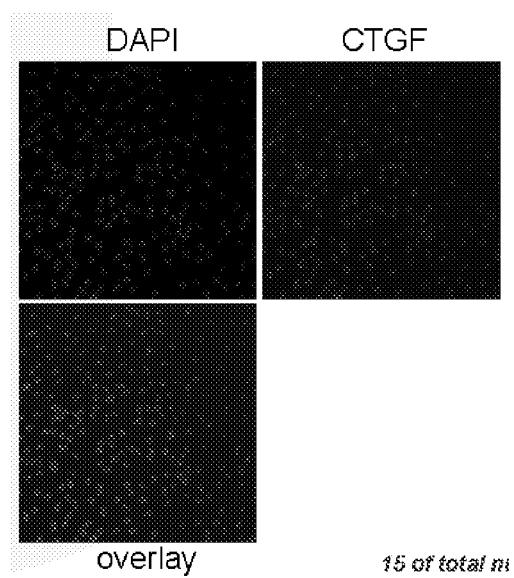
Figure 23B:
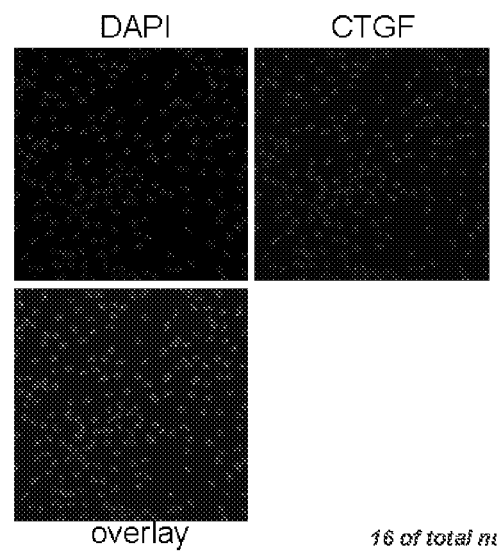
Figure 23C:
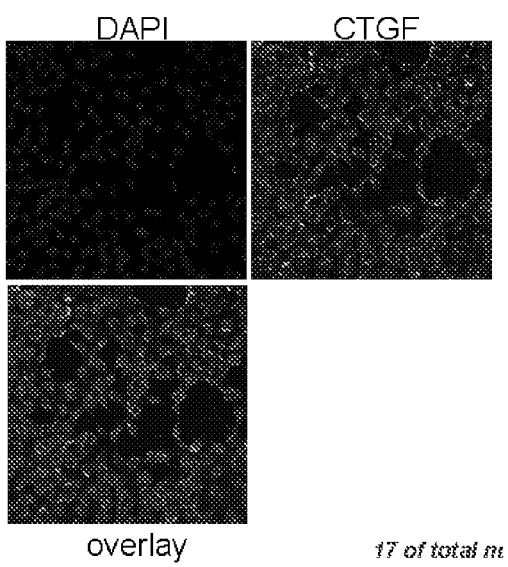
Figure 23D:
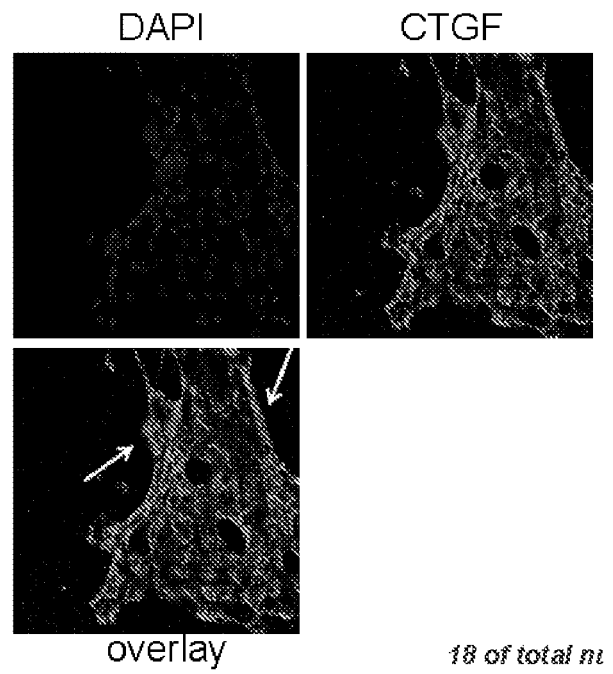
Figure 23E:
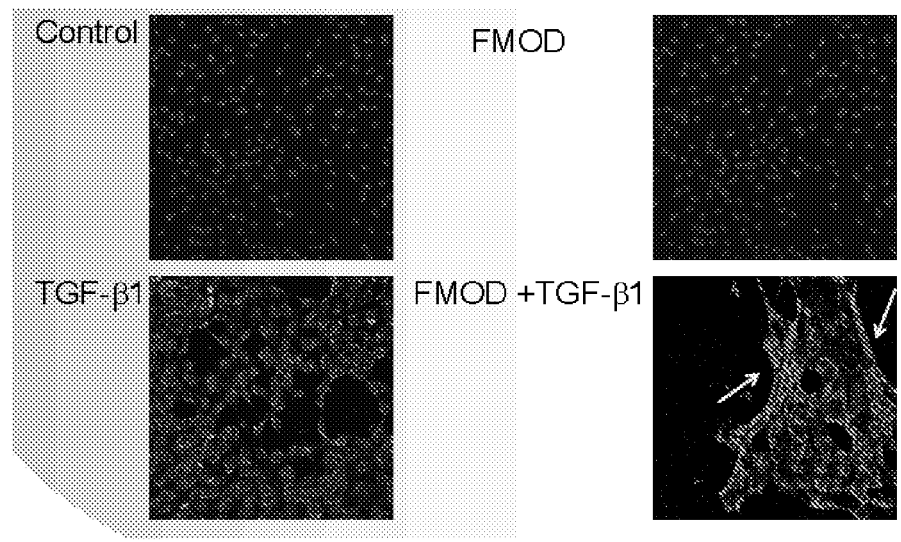

FIGS. 23A-23E show the results of tests on effects of FMOD, alone or in combination with TGF-β on expression of CTGF. FIG. 23A shows the results from 2-day control treatment. FIG. 23B shows the results from 2-day FMOD mono-treatment. FIG. 23C shows the results from 2-day TGF-β mono-treatment. FIG. 23D shows the results from 2-day FMOD+TGF-β1 combo-treatment. FIG. 23E shows a comparison chart of the results in FIGS. 23A-23D, respectively.

Figure 24:
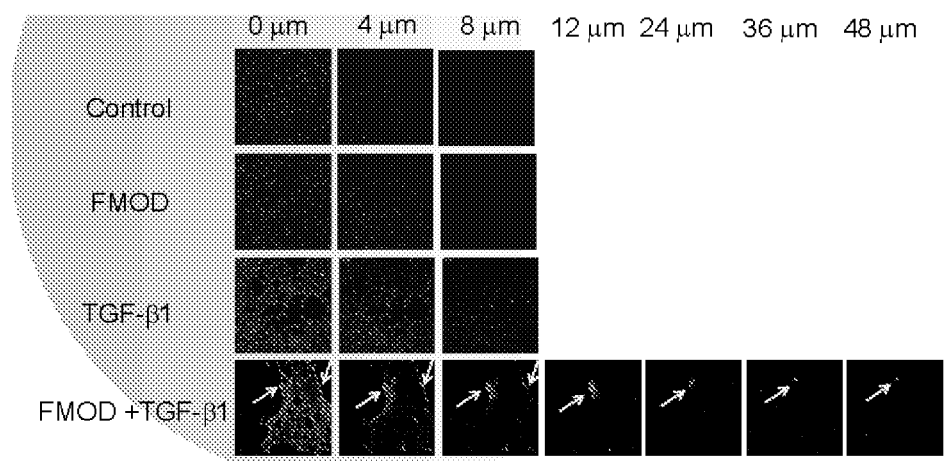

FIG. 24 shows that TGF-β1 treatment increases expression of CTGF (green fluorescence), while TGF-β1/FM26OD combo-treatment significantly increases expression of CTGF (green fluorescence) relative to TGF-β1 mono-treatment.

Figure 25A:
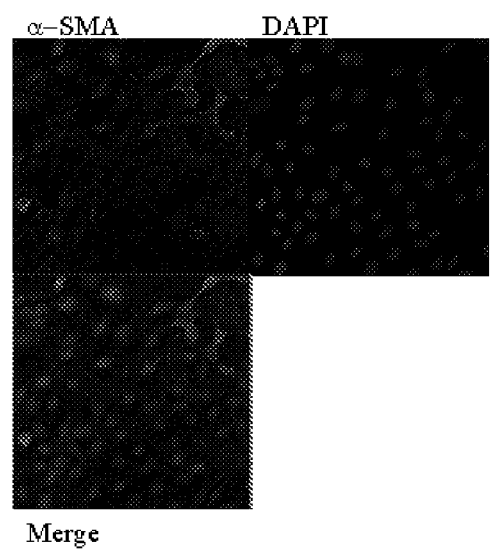
Figure 25B:
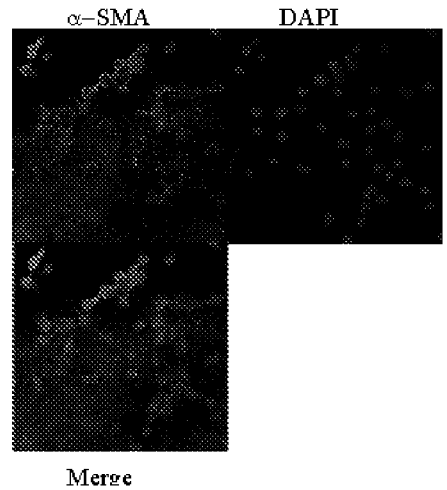

FIGS. 25A-25D show the results of tests on effects of FMOD and TGF-β or FMOD peptides and TGF-β on α-smooth muscle actin (α-SMA) expression. FIG. 25A shows the results from control tests, which shows minimal α-SMA staining. FIG. 25B shows the results from 200 nM FMOD treatment, which shows minimal α-SMA staining.

Figure 25C:
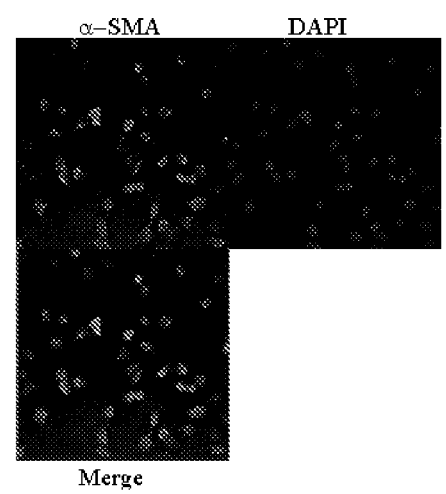
Figure 25D:
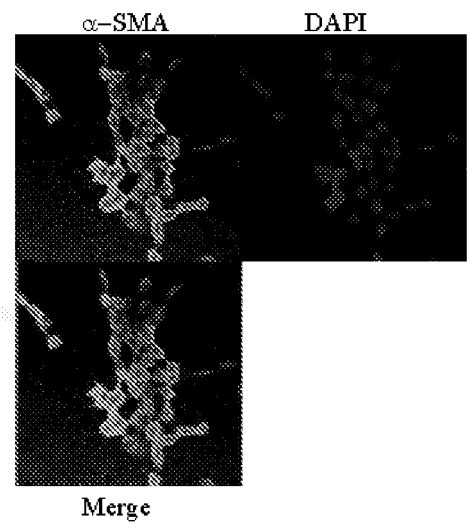

FIG. 25C shows the results from 100 pM TGF-β1 treatment, which shows moderate α-SMA staining. FIG. 25D shows the results from 100 pM TGF-β1+200 nM FMOD treatment, which shows significantly increased α-SMA staining accompanied by increased cell density/cell aggregation.

Figure 26A:
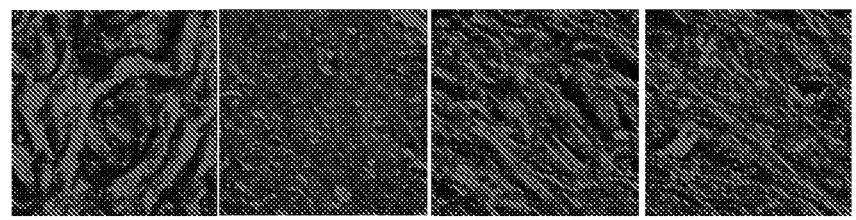
Figure 26B:
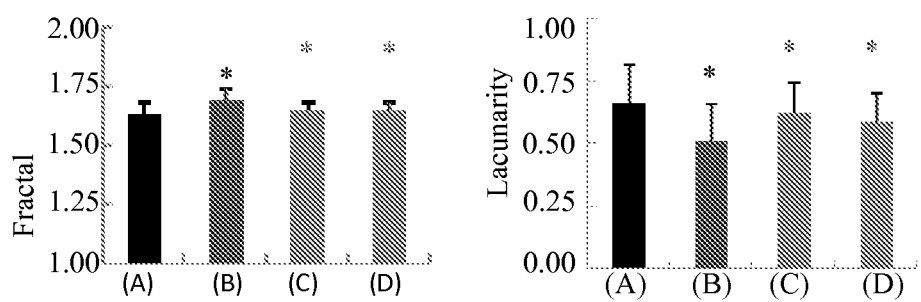

FIGS. 26A-26B show the results of tests on healing by a FMOD-P.

DETAILED DESCRIPTION OF THE INVENTION

According to one aspect of the invention, it is provided a fibromodulin (FMOD) peptide (FMOD-P) comprising at least one site capable of binding to transforming growth factor-β (TGF-β). In some embodiments, the FMOD-P has an amino acid sequence selected from the group, but not limited to consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, and SEQ ID NO:63.

According to another aspect of the present invention, it is provided a composition.

The composition comprises an effective amount of any of the following ingredients:
 a) a FMOD-P;
 b) a combination of FMOD-P;
 c) a FMOD-P or a combination of FMOD-P and at least one TGF-β isoform;
 d) FMOD and at least one TGF-β isoform;
 e) FMOD and a FMOD-P or a combination of FMOD-P; and
 f) any combination of (a)-(e), wherein the composition is effective for modulating activities of TGF-β and/or collagen assembly.

In some embodiments, the FMOD-P has an amino acid sequence selected from, but not limited to, the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, and SEQ ID NO:63.

In some further embodiments, a TGF-β isoform is one of TGF-β1 (SEQ ID NO:64), TGF-β2 (SEQ ID NO:65), and TGF-β3 (SEQ ID NO:66).

In some further embodiments, the composition further comprises an excipient. In some embodiment, the excipient is a pharmaceutically acceptable carrier or dermatologically acceptable carrier.

The composition disclosed herein can be a formulated for systemic or local delivery. In some embodiments, local delivery is topical delivery, transdermal delivery, intradermal delivery, microneedle delivery, delivery as a coating on medical devices (e.g., cardiovascular stents, breast implants), or delivery by impregnating or coating on various scaffold devices (e.g., allograft dermis, Integra dermal regeneration template). In some further embodiments, systemic delivery is injection, oral administration, nasal delivery, or inhalation.

According to a further aspect of the present invention, it is provided a method of making a FMOD-P. The method comprises:
 designing a FMOD-P having the function and at least one binding site of FMOD, and
 preparing the FMOD-P.

In some embodiments, preparing comprises splicing FMOD at one or more selected sites to generate the FMOD-P.

In some embodiments, preparing comprises expressing the FMOD-P in a recombinant system, e.g., expressing the FMOD-P in a bacterial, yeast, mammalian, or plant cell or producing the peptide in a cell free system (e.g., a cell free translation system).

In some embodiments, preparing comprises synthesizing the FMOD-P using peptide synthesizer machines.

In some embodiments, designing comprises hydrophobic analysis of a primary or secondary structure of FMOD.

According to a further aspect of the present invention, it is provided a method of making a composition. The method comprises:
 providing an ingredient selected from any of the following:
 a) a FMOD-P;
 b) a combination of FMOD-P;
 c) a FMOD-P or a combination of FMOD-P and at least one TGF-β isoform;
 d) FMOD and at least one TGF-β isoform;
 e) FMOD and a FMOD-P or a combination of FMOD-P; and
 f) any combination of (a)-(e), and
 forming a composition comprising any of ingredients (a)-(f).

In some embodiments, the step forming further comprises: providing an excipient, and forming a formulation comprising the ingredient and the excipient.

According to a still further aspect of the present invention, it is provided a method of treating, preventing, or ameliorating a body condition. The method comprises administering to a subject:
 a FMOD-P disclosed herein;
 a composition disclosed herein; or
 a formulation disclosed herein.

The body condition can be any condition in which modulation of TGF-β activity and/or collagen assembly at ultra-, micro-, and macrostructural levels is desired, for example, such a condition can be one where modulation of TGF-β activity and/or collagen assembly imparts a beneficial effect. Examples of such body conditions can be, diseases such as excessive fibrosis or scar formation that are associated with high TGF-β expression, hypertrophic scars, keloids, radiation fibrosis, fibrotic conditions in organs systems other than skin conditions, such as, but not limited to lung (pulmonary fibrosis) (Gharaee-Kermani, Hu et al. 2009), liver, kidney, cornea, intra-abdominal, gastrointestinal, urological, neurological, or cardiovascular conditions.

The FMOD-P or a composition thereof can be applied to a patient through a suitable mode of delivery, e.g., topical application, injection, local delivery such as delivery via a drug-eluting stent, balloon, or catheter, or delivery through an inhaler. The smaller size of the novel FMOD peptides may make pulmonary delivery using inhalational techniques much more feasible than the much larger FMOD whole protein.

As used herein, the term "fibromodulin (FMOD)" (SEQ ID NO:1; Genebank NM_002023) refers to a fibromodulin molecule as generally known in the art. Examples of FMOD molecules are disclosed in (Heinegard, Larsson et al. 1986), as shown in SEQ ID NO:1, and SEQ ID NO:2 (Genebank BC035381), SEQ ID NO:3 (Genebank U05291), SEQ ID NO:4 (Genebank AK303866), SEQ ID NO:5 (Genebank AK172740), SEQ ID NO:6 (Genebank AK092999), SEQ ID NO:7 (Genebank AK027694), SEQ ID NO:8 (Genebank DQ892112), SEQ ID NO:9 (Genebank X72913), SEQ ID NO:10 (Genebank S75546), SEQ ID NO:11 (Genebank AY890642), SEQ ID NO:12 (Genebank AY893119). Information for these sequences is:

SEQ ID NO: 1:
NH$_2$-

WTSLLLLAGLFSLSQAQYEDDPHWWFHYLRSQQSTYYDPYDPYPYETYEP

YPYGVDEGPAYTYGSPSPPDPRDCPQECDCPPNFPTAMYCDNRNLKYLPF

VPSRMKYVYFQNNQITSIQEGVFDNATGLLWIALHGNQITSDKVGRKVFS

KLRHLERLYLDHNNLTRMPGPLPRSLRELHLDHNQISRVPNNALEGLENL

TALYLQHNEIQEVGSSMRGLRSLILLDLSYNHLRKVPDGLPSALEQLYME

HNNVYTVPDSYFRGAPKLLYVRLSHNSLTNNGLASNTFNSSSLLELDLSY

NQLQKIPPVNTNLENLYLQGNRINEFSISSFCTVVDVVNFSKLQVLRLDG

NEIKRSAMPADAPLCLRLASLIEI-COOH

SEQ ID NO: 2:
NH$_2$-

MQWTSLLLLAGLFSLSQAQYEDDPHWWFHYLRSQQSTYYDPYDPYPYET

YEPYPYGVDEGPAYTYGSPSPPDPRDCPQECDCPPNFPTAMYCDNRNLKY

LPFVPSRMKYVYFQNNQITSIQEGVFDNATGLLWIALHGNQ

ITSDKVGRKVFSKLRHLERLYLDHNNLTRMPGPLPRSLRELHLDHNQISR

VPNNALEGLENLTALYLQHNEIQEVGSSMRGLRSLILLDLSYNHLRKVPD

GLPSALEQLYMEHNNVYTVPDSYFRGAPKLLYVRLSHNSLTNNGLASNTF

NSSSLLELDLSYNQLQKIPPVNTNLENLYLQGNRINEFSISSFCTVVDVV

NFSKLQVLRLDGNEIKRSAMPADAPLCLRLASLIEI-COOH

SEQ ID NO: 3:
NH$_2$-

YLQGNRINEFSISSFCTVVDVVNFSKLQVLRLDGNEIKRSAMPADAPLCL

RLASLIEI-COOH

SEQ ID NO: 4:
NH$_2$-

QWTSLLLLAGLFSLSQAQYEDDPHWWFHYLRSQQSTYYDPYDPYPYETY

EPYPYGVDEGPAYTYGSPSPPDPRDCPQECDCPPNFPFVPSRMKYVYFQN

NQITSIQEGVFDNATGLLWIALHGNQITSDKVGRKVFSKLRHLERLYLDH

NNLTRMPGPLPRSLRELHLDHNQISRVPNNALEGLENLTALYLQHNEIQE

VGSSMRGLRSLILLDLSYNHLRKVPDGLPSALEQLYMEHNNVYTVPDSYF

RGAPKLLYVRLSHNSLTNNGLASNTFNSSSLLELDLSYNQLQKIPPVNT

NLENLYLQGNRINEFSISSFCTVVDVVNFSKLQVLRLDGNEIKRSAMPAD

APLCLRLASLIEI-COOH

SEQ ID NO: 5:
NH$_2$-

MKMTLIGGSTTSAASSPPTTIPMTLTRMRPTSLTPMGWMKGQPTPTALHL

DHNQISRVPNNALEGLENLTAMYCDNRNLKYLPFVPSRMKYVYFQNNQIT

SIQEGVFDNATGLLWIALHGNQITSDKVGRKVFSKLRHLERLYLDHNNLT

RMPGPLPRSLRELHLDHNQIPATAPRNATAHPTSPRPCTSNTMRSRKWAV

P-COOH

SEQ ID NO: 6:
NH$_2$-

MKMTLIGGSTTSAASSPPTTIPMTLTRMRPTSLTPMGWMKGQPTPTALHP

LQIPATAPRKVFSKLRHLERLYLDHNNLTRMPGPLPRSLRELHLDHNQIS

RVPNNALEGLENLTALYLQHNEIQEVGSSMRGLRSLILLDLSYNHLRKVP

DGLPSALEQLYMEHNNVYTVPDSYFRGAPKLLYVRLSHNSLTNNGLASNT

FNSSSLLELDLSYNQLQKIPPVNTNLENLYLQGNRINEFSISSFCTVVDV

VNFSKLQVLRLDGNEIKRSAMPADAP LCLRLASLIEI-COOH

SEQ ID NO: 7:
NH$_2$-

MQWTSLLLLAGLFSLSQAQYEDDPHWWFHYLRSQQSTYYDPYDPYPYET

YEPYPYGVDEGPAYTYGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIEI-COOH

SEQ ID NO: 8:
NH$_2$-

MQWTSLLLLAGLFSLSQAQYEDDPHWWFHYLRSQQSTYYDPYDPYPYET

YEPYPYGVDEGPAYTYGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIEI-COOH

SEQ ID NO: 9:
NH$_2$-

MQWTSLLLLAGLFSLSQAQYEDDPHWWFHYLRSQQSTYYDPYDPYPYET

YEPYPYGVDEGPAYTYGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLYLLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSQLQVVR

LDGNEMKRSAMPAEAPLCLRLASLIEI-COOH

SEQ ID NO: 10:
NH$_2$-

MQWASLLLLAGLFSLSQAQYEDDPHWWFHYLRSQQSTYYDPYDPYPYET

YEPYPYGVDEGPAYTYGSPSPPDPRDCPQECDCPPNFLTAMYCDNRNLKY

LPFVPSRMKYVYFQNNQITSIQEGVFDNATGLLWIALHGNQITSDKVGRK

SEQ ID NO: 10 (continued)

VFSKLRHLERLYLDHNNLTRMPGPLPRSLRELHLDHNQISRVPNNALEGL

ENLTALYLQHDEIQEVGSSMRGLRSLILLDLSYNHLRKVPDGLPSALEQL

YMEHNNVYTVPDSYFRGAPKLLYVRLSHNSLTNNGLASNTFNSSSLELDL

SYNQLQKIPPVNTNLENLYLQGNRINEFSISSFCTVVDVVNFSKLQVVRL

DGNEIKRSAMPADAPLCLRLASLIEI-COOH

SEQ ID NO: 11:
NH$_2$-

MQWTSLLLLAGLFSLSQAQYEDDPHWWFHYLRSQQSTYYDPYDPYPYET

YEPYPYGVDEGPAYTYGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIGI-COOH

SEQ ID NO: 12:
NH$_2$-

MQWTSLLLLAGLFSLSQAQYEDDPHWWFHYLRSQQSTYYDPYDPYPYET

YEPYPYGVDEGPAYTYGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIEIL-COOH

As used herein, the term TGF-β isoform refers to a TGF-β peptide having a shorter amino acid sequence as compared to TGF-β that retains the function and binding sites of TGF-β. In some embodiments, the term TGF-β isoform can be used interchangeably with the term TGF-β peptide. Examples of such TGF-β isoforms are TGF-β-1 (SEQ ID NO:64), TGF-β-2 (SEQ ID NO:65), and TGF-β-3 (SEQ ID NO:66). Information for these sequences is:

SEQ ID NO: 64:
NH$_2$-

ALDTNYCFSSTEKNCCVRQLYIDFRKDLGWKWIHEPKGYHANFCLGPCPY

IWSLDTQYSKVLALYNQHNPGASAAPCCVPQALEPLPIVYYVGRKPKVEQ

LSNMIVRSCKCS-COOH

SEQ ID NO: 65:
NH$_2$-

QDNCCLRPLYIDFKRDLGWKWIHEPKGYNANFCAGACPYLWSSDTQHRV

LSLYNTINPEASASPCCVSQDLEPLTILYYIGKTPKIEQLSNMIVKSCK

CS-COOH

SEQ ID NO: 66:
NH$_2$-NCCVRPLYIDFRQDLGWKWVHEPKGYYANFCSGPCPYLRSA

DTTHSTVLGLYNTLNPEASASPCCVPQDLEPLTILYYVGRTPKVEQLSNM

VVKSCKCS-COOH

As used herein, the term "beneficial effect" refers to a biologically significant improvement of a body condition, which is readily ascertainable by a person of ordinary or specialized skill in the art, depending on the "beneficial effect" described. For instance, if the "beneficial effect" is improvement in scar appearance, then a person of ordinary skill can make that ascertainment. However, if the "beneficial effect" is decreased biliary stent stenosis or decreased coronary vessel stent stenosis or decreased intra-abdominal adhesions, then a person of specialized skill is required to make that ascertainment.

Fibromodulin Peptides

As used herein, the term fibromodulin peptide (FMOD-P) refers to a FMOD isoform having a shorter amino acid sequence as compared to FMOD that retains some of the function and binding sites of fibromodulin (FMOD) or perhaps novel function and binding sites not normally exposed in FMOD. In some embodiments, FMOD-P can be used interchangeably with the term FMOD isoform. Throughout the whole document of the instant application, FMOD-P is sometimes described as FMOD peptide(s), invention FMOD-P(s) or invention FMOD peptide(s).

In some embodiments, the term FMOD-P encompasses a functional or structural derivative of the invention FMOD-P. Such derivatives can be made by, e.g., derivatizing an invention FMOD-P by established methodology, e.g., chemical modification or physical modification. Chemical modification includes, e.g., modification using an acid, a base, esterification, PEGylation, or alkylation with a short chain alkyl group. Physical modification includes, e.g., heating, moisture treatment, light treatment, mechanical impact, etc.

Examples of FMOD-P include, but are not limited to, peptides of the following sequences: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, and SEQ ID NO:63.

Sequence information for some of the amino acid sequences is listed as follows:

SEQ ID NO: 13:
NH$_2$-NRNLKYKPFVPSRMK-COOH

SEQ ID NO: 14:
NH$_2$-FQNNQITSIQEGVFDNATGLL-COOH

SEQ ID NO: 15:
NH₂-NRNLKYKPFVPSRMK-COOH

SEQ ID NO: 16:
NH₂-YLRSQQSTYYDPYDPYPYETYEPYPYGVDEGPAYTYGSPSPPDPRDCPQECDCPPNFPTAMYCD-COOH

SEQ ID NO: 17:
NH₂-PYGVDEGPAYTYGSPSPPDPRDCPQECDCPPNFPTAMYD-COOH

SEQ ID NO: 18:
NH₂-SRMKYVYFQNNQITSIQEGVFDNATGLLWIALHGNQITS-COOH

SEQ ID NO: 19:
NH₂-NRNLKYLPFVPSRMKYVYFQNNQITSIQEGVFDNATGLLWIALHGNQITS-COOH

SEQ ID NO: 20:
NH₂-DKVGRKVFSKLRHLERLYLDHNNLTRMPGPLPRSLRELHLDHNQI-COOH

SEQ ID NO: 21:
NH₂-SRVPNNALEGLENLTALYLQHNEIQEVGSSMRGLRSLILLDLSYNHLRKVPDGLPSALEQLYMEHNNV-COOH

SEQ ID NO: 22:
NH₂-YTVPDSYFRGAPKLLYVRLSHNSLTNNGLASNTFNSSSLLELDLSYNQLQKIPPVNTNLENLYLQGNRI-COOH

SEQ ID NO: 23:
NH₂-NEFSISSFCTVVDVVNFSKLQVLRLDGNEIKRSAMPADAPLCLRLASLIEI-COOH

SEQ ID NO: 24:
NH₂-QWTSLLLLAGLFSLSQAQYEDDPHWWFHYLRSQQSTYYDP-COOH

SEQ ID NO: 25:
NH₂-DDPHWWFHYLRSQQSTYYDPYDPYPYETYEPYPYGVDEGP-COOH

SEQ ID NO: 26:
NH₂-DPRDCPQECDCPPNFPTAMYCDNRNLKYLPFVPSRMKYVYFQNNQITSIQ-COOH

SEQ ID NO: 27:
NH₂-YGSPSPPDPRDCPQECDCPPNFPTAMYCDNRNLKYLPFVPSRMKYVYFQNN-COOH

SEQ ID NO: 28:
NH₂-FPTAMYCDNRNLKYLPFVPSRMKYVYFQNNQITSIQEGVFDNATGLLWIA-COOH

SEQ ID NO: 29:
NH₂-LLWIALHGNQITSDKVGRKVFSKLRHLERLYLDHNNLTRMPGPLPRSLRELHLDHNQI-COOH

SEQ ID NO: 30:
NH₂-AYTYGSPSPPDPRDCPQECDCPPNFPTAMYCDNRNLKYLPFVPSRMKYVY-COOH

SEQ ID NO: 31:
NH₂-SRVPNNALEGLENLTALYLQHNEIQEVGSSMRGLRSLILLDLSYNHL-COOH

SEQ ID NO: 32:
NH₂-RKVPDGLPSALEQLYMEHNNVYTVPDSYFRGAPKLLYVRLSHNSLT-COOH

SEQ ID NO: 33:
NH₂-NNGLASNTFNSSSLLELDLSYNQLQKIPPVNTNLENLYLQGNRI-COOH

SEQ ID NO: 34:
NH₂-TSIQEGVFDNATGLLWIALHGNQITSDKVGRKVFSKLRHLERLYLDHNNL-COOH

SEQ ID NO: 35:
NH₂-TRMPGPLPRSLRELHLDHNQISRVPNNALEGLENLTALYLQHNEIQE-COOH

SEQ ID NO: 36:
NH₂-VGSSMRGLRSLILLDLSYNHLRKVPDGLPSALEQLYMEHNNV-COOH

SEQ ID NO: 37:
NH₂-YTVPDSYFRGAPKLLYVRLSHNSLTNNGLASNTFNSSSLLELDLSYNQL-COOH

SEQ ID NO: 38:
NH₂-QKIPPVNTNLENLYLQGNRINEFSISSFCTVVDVVNFSKLQVLRLDGNEI-COOH

SEQ ID NO: 39:
NH₂-DKVGRKVFSKLRHLERLYLDHNNLTRMPGPLPRSLRELHLDHNQISRVPNNALEGLEN-COOH

SEQ ID NO: 40:
NH₂-NATGLLWIALHGNQITSDKVGRKVFSKLRHLERLYLDHNN-COOH

SEQ ID NO: 41:
NH₂-NATGLLWIALHGNQITSDKVGRKVFSKLRHLERLYLDHNNLTRMPGPLPRSLRELHLDHNQISRVPNNALEGLEN-COOH

SEQ ID NO: 42:
NH₂-NLTALYLQHNEIQEVGSSMRGLRSLILLDLSYNHLRKVPDGLPSALEQLYMEHNNVYTVPDSYFRGAPKLLYVRLSHNSLTNNGLASNTFN-COOH

SEQ ID NO: 43:
NH₂-TRMPGPLPRSLRELHLDHNQISRVPNNALEGLENLTALYLQHNEIQEVGSSMRGLRSLILLDLSYNHL-COOH

SEQ ID NO: 44:
NH₂-RKVPDGLPSALEQLYMEHNNVYTVPDSYFRGAPKLLYVRLSHNSLTNNGLASNTFN-COOH

SEQ ID NO: 45:
NH₂-NSSSLLELDLSYNQLQKIPPVNTNLENLYLQGNRINEFSISSFC-COOH

SEQ ID NO: 46:
NH₂-CTVVDVVNFSKLQVLRLDGNEIKRSAMPADAPLC-COOH

SEQ ID NO: 47:
NH₂-QKIPPVNTNLENLYLQGNRINEFSISSFCTVVDVVNFSKLQVLRLDGNEIKRSAMPADAPLC-COOH

SEQ ID NO: 48:
NH₂-CPQECDCPPNFPTAMYCDNRNLKYLPFVPSRMKYVYFQNNQI-COOH

SEQ ID NO: 49:
NH₂-ATGLLWIALHGNQITSDKVGRKVFSKLRHLERLYLDHNNLTRMPGPLPRSLRELHLDHNQIS-COOH

SEQ ID NO: 50:
NH₂-NLTRMPGPLPRSLRELHLDHNQISRVPNNALEGLENLTALYLQHNEIQE-COOH

SEQ ID NO: 51:
NH₂-NLTRMPGPLPRSLRELHLDHNQISRVPNNALEGLEN-COOH

SEQ ID NO: 52:
NH₂-GLPSALEQLYMEHNNVYTVPDSYFRGAPKLLYVRLSHNSLTNNGLAS-COOH

SEQ ID NO: 53:
NH₂-HLDHNQISRVPNNALEGLENLTALYLQHNEIQEVGSSMRG-COOH

SEQ ID NO: 54:
NH₂-FSKLQVLRLDGNEIKRSAMPADAPLCRLASLIE-COOH

SEQ ID NO: 55:
NH₂-PNNALEGLENLTALYLQHNEIQEVGSSMRGLRSLILLDL-COOH

SEQ ID NO: 56:
NH₂-PDGLPSALEQLYMEHNNVYTVPDSYFRGAPKLLYVRLSHNSLTNNGLAS-COOH

SEQ ID NO: 57:
NH₂-LLDLSYNHLRKVPDGLPSALEQLYMEHNNVYTVPDSYFRG-COOH

SEQ ID NO: 58:
NH₂-SKLRHLERLYLDHNNLTRMPGPLPRSLRELHLDHNQISRVPNNALEGLEN-COOH

SEQ ID NO: 59:
NH₂-LRSLILLDLSYNHLRKVPDGLPSALEQLYMEHNNVYTVPD-COOH

SEQ ID NO: 60:
NH₂-YVRLSHNSLTNNGLASNTFNSSSLLELDLSYNQLQKIPPV-COOH

SEQ ID NO: 61:
NH₂-NNGLASNTFNSSSLLELDLSYNQLQKIPPVNTNLENLYLQ-COOH

SEQ ID NO: 62:
NH₂-HWWFHYLRSQQSTYYDPYDPYPYETYEPYPYGVDEGPAYTYGSPSPPDPRD-COOH

SEQ ID NO: 63:
NH₂-HNSLTNNGLASNTFNSSSLLELDLSYNQLQKIPPVNTNL-COOH

The FMOD-P disclosed herein can be made by a method comprising:
designing a peptide having a shorter amino acid sequence as compared to FMOD that retains the function and binding sites of FMOD or perhaps novel function and binding sites not normally exposed in FMOD; and
preparing the peptide.

In some embodiments, the act of designing can include steps of performing a hydrophobic analysis of a primary or secondary structure of FMOD and finding the binding site of FMOD.

In some embodiments, the act of preparing comprises splicing a FMOD at a specific site or sites so as to form a peptide as defined. Splicing a protein to form a peptide at a site or sites are well established laboratory techniques, which can be readily performed by a person of ordinary skill in the art.

In some further embodiments, the act preparing the peptide includes expressing the peptide in a recombinant system or producing the peptide in a cell free system (e.g., a cell free translation system). Such a recombinant system can be a bacteria, yeast, mammalian cell, or plant cell, which can be readily performed by a person of ordinary skill in the art.

In some other embodiments, preparing comprises synthesizing the FMOD-P using peptide synthesizer machines.

Compositions

The composition disclosed herein can include any of the following:

a) a FMOD-P;
b) a combination of FMOD-P;
c) a FMOD-P or a combination of FMOD-P and at least one TGF-β isoform;
d) FMOD and at least one TGF-β isoform;
e) FMOD and a FMOD-P or a combination of FMOD-P; and
f) any combination of (a)-(e).

In some embodiments, the TGF-β isoform can be any TGF-β peptide, e.g., TGF-β1, TGF-β2, TGF-β3, or a combination of TGF-β1, TGF-β2, and TGF-03, such as (TGF-β1+ TGF-β2), (TGF-β1+TGF-β3), or (TGF-β2+TGF-×3).

In the above compositions, the FMOD-P is as defined above. In some embodiments, the composition includes an effective amount of any of the above (a)-(e) elements.

The composition described herein can be formulated into any desired formulation. The composition can include materials and carriers to effect a desired formulation. For example, the composition can include an injectable or moldable material that can set within a pre-defined period of placement. Such a pre-defined period can be, e.g., 10 minutes, 30 minutes, one hour, two hours, etc.

In some embodiments, the composition can include a chemical gel that includes primary bonds formed due to changes in pH, ionic environment, and solvent concentration. Examples of such chemical gels can be, but are not limited to, polysaccharides such as chitosan, chitosan plus ionic salts such as beta-glycerophosphates, aginates plus $Ba^{2+}$, $Sr^{2+}$, $Ca^{2+}$, $Mg^{2+}$, collagen, fibrin, plasma or combinations thereof.

In some embodiments, the composition can include a physical gel that includes secondary bonds formed due to temperature changes. Examples of such physical gels can be, but are not limited to, alginate, poly(ethylene glycol)-poly (lactic acid-co-glycolic acid)-poly(ethylene glycol) (PEG-PLGA-PEG) tri-block copolymers, agarose, and celluloses. In some embodiments, physical gels that can be used in the composition described herein can include physical gels that are liquid under high shear but gels to solid at low shear. Examples of such physical gels include, but are not limited to, hyaluronic acid, or polyethylene oxides. The physical gels can have pre-formed materials with pre-defined dimensions and shape.

In some embodiments, the composition described herein can include a material that degrades or releases active agents in response to a stimulus. Some examples of such stimuli are mechanical stimuli, light, temperature changes, pH changes, change of ionic strength, or electromagnetic field. Such materials are known in the art. Some examples of such materials are chitosan, alginates, pluronics, methyl cellulose, hyaluronic acids, and polyethylene oxides. Other examples are described by Brandl F, Sommer F, Goepferich A. "Rational design of hydrogels for tissue engineering: Impact of physical factors on cell behavior" in Biomaterials. Epub 2006 Sep. 29.

In some embodiments, the composition described herein can include a gel containing any of hydroxyapatites, apatites, tricalcium phosphates, calcium phosphates, bioactive glass, human allograft bone and cartilage, bovine bone and cartilage, or their mixtures thereof.

In some embodiments, the composition described herein including any of the gels described above can further include a crosslinker to further tailor degradation kinetics and controlled release. Alternatively, in some embodiments, the composition described herein can include an interpenetrating phase composite or interpenetrating network (IPN) that includes any of the above described gels. Some examples of the crosslinker includes, but are not limited to, common crosslinking agents (polyalkylene oxide, ethylene dimethacrylate, N,N'-methylenebisacrylamide, methylenebis(4-phenyl isocyanate), ethylene dimethacrylate, divinylbenzene, allyl methacrylate, carbodiimidazole, sulfonyl chloride, chlorocarbonates, n-hydroxysuccinimide ester, succinimidyl ester, epoxides, aryl halides, sulfasuccinimidyl esters, and maleimides); PEG based crosslinkers (e.g. MAL-dPEGx-NHS-esters, MAL-dPEGx acid, Bis-MAL-dPEGx, etc.) and photo/light activated crosslinkers, N-hydroxysuccinimide-based crosslinkers, dilysine, trilysine, and tetralysine.

The composition described herein can include a carrier. The carrier can be a polymeric carrier or non-polymeric carrier. In some embodiments, the carrier can be biodegradable, such as degradable by enzymatic or hydrolytic mechanisms. Examples of carriers include, but are not limited to synthetic absorbable polymers such as but not limited to poly(α-hydroxy acids) such as poly (L-lactide) (PLLA), poly (D, L-lactide) (PDLLA), polyglycolide (PGA), poly (lactide-co-glycolide) (PLGA), poly (-caprolactone), poly (trimethylene carbonate), poly (p-dioxanone), poly (-caprolactone-co-glycolide), poly (glycolide-co-trimethylene carbonate) poly (D, L-lactide-co-trimethylene carbonate), polyarylates, polyhydroxybutyrate (PHB), polyanhydrides, poly (anhydride-co-imide), propylene-co-fumarates, polylactones, polyesters, poly carbonates, polyanionic polymers, polyanhydrides, polyester-amides, poly(amino-acids), homopolypeptides, poly(phosphazenes), poly (glaxanone), polysaccharides, and poly(orthoesters), polyglactin, polyglactic acid, polyaldonic acid, polyacrylic acids, polyalkanoates; copolymers and admixtures thereof, and any derivatives and modifications. See for example, U.S. Pat. No. 4,563,489, and PCT Int. Appl. No. WO/03024316, herein incorporated by reference. Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

In one embodiment, the carrier can further be coated by compositions, including bioglass and or apatites derived from sol-gel techniques, or from immersion techniques such as, but not limited to simulated body fluids with calcium and phosphate concentrations ranging from about 1.5 to 7-fold the natural serum concentration and adjusted by various means to solutions with pH range of about 2.8-7.8 at temperature from about 15-65 degrees C. See, for example, U.S. Pat. Nos. 6,426,114 and 6,013,591; and PCT Int. Appl. WO/9117965 herein incorporated by reference.

Other examples of carriers include, collagen (e.g. Collastat, Helistat collagen sponges), hyaluronan, fibrin, chitosan, alginate, and gelatin. See for example, PCT Int. Appls. WO/9505846; WO/02085422, herein incorporated by reference.

In one embodiment, the carrier can include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity.

See for example, Journal of Biological Chemistry (2003), 278(44), p. 43229-43235, herein incorporated by reference.

In one embodiment, the composition can be in the form of a liquid, solid or gel. In one embodiment, the substrate can include a carrier that is in the form of a flowable gel. The gel can be selected so as to be injectable, such as via a syringe at the site where cartilage formation is desired. The gel can be a chemical gel which can be a chemical gel formed by primary bonds, and controlled by pH, ionic groups, and/or solvent concentration. The gel can also be a physical gel which can be formed by secondary bonds and controlled by temperature and viscosity. Examples of gels include, but are not limited to, pluronics, gelatin, hyaluronan, collagen, polylactide-polyethylene glycol solutions and conjugates, chitosan, chitosan & b-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263(4), 342-349, herein incorporated by reference.

In one embodiment, the carrier can be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate. See for example, U.S. Pat. No. 5,410,016, herein incorporated by reference.

In one embodiment, the composition can include a carrier that is temperature sensitive. Examples include carriers made from N-isopropylacrylamide (NiPAM), or modified NiPAM with lowered lower critical solution temperature (LCST) and enhanced peptide (e.g. NELL1) binding by incorporation of ethyl methacrylate and N-acryloxysuccinimide; or alkyl methacrylates such as butylmethacrylate, hexylmethacrylate and dodecylmethacrylate. PCT Int. Appl. WO/2001070288; U.S. Pat. No. 5,124,151 herein incorporated by reference.

In one embodiment, where the carrier can have a surface that is decorated and/or immobilized with cell adhesion molecules, adhesion peptides, and adhesion peptide analogs which can promote cell-matrix attachment via receptor mediated mechanisms, and/or molecular moieties which can promote adhesion via non-receptor mediated mechanisms binding such as, but not limited to polycationic polyamino-acid-peptides (e.g. poly-lysine), polyanionic polyamino-acid-peptides, Mefp-class adhesive molecules and other DOPA-rich peptides (e.g. poly-lysine-DOPA), polysaccharides, and proteoglycans. See for example, PCT Int. Appl. WO/2004005421; WO/2003008376; WO/9734016, herein incorporated by reference.

In one embodiment, the carrier can include various naturally occurring matrices or their components such as devitalized cartilage matrix, demineralized bone matrix, or other components derived from allograft, xenograft, or any other naturally occurring material derived from Monera, Protista, Fungi, Plantae, or Animalia kingdoms.

In one embodiment, the carrier can include one or more sequestering agents such as, but not limited to, collagen, gelatin, hyaluronic acid, alginate, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, blood, fibrin, polyoxyethylene oxide, calcium sulfate hemihydrate, apatites, carboxyvinyl polymer, and poly(vinyl alcohol). See for example, U.S. Pat. No. 6,620,406, herein incorporated by reference.

In one embodiment, the carrier can include surfactants to promote stability and/or distribution of FMOD-P, FMOD, and/or TGF-β isoform within the carrier materials such as, but not limited to polyoxyester (e.g. polysorbate 80, polysorbate 20 or Pluronic F-68).

In one embodiment, the carrier can include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier can include a combination of materials such as those listed above. By way of example, the carrier can be a PLGA/collagen carrier membrane. The membrane can be soaked in a solution including FMOD-P, FMOD, and/or TGF-β isoform.

An implant can include a substrate formed into the shape of a stent, mesh, pin, screw, plate, or prosthetic joint. An implant can include a substrate that is resorbable, such as a substrate including collagen.

The FMOD-P, FMOD, and/or TGF-β isoform peptide can be combined with a acceptable carrier to form a pharmacological composition. Acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a carrier, including a physiologically acceptable compound depends, for example, on the route of administration.

The compositions can be administered in a variety of unit dosage forms depending upon the method of administration. For example, unit dosage forms suitable can include powder, or injectable or moldable pastes or suspension.

The compositions of this invention can comprise a solution of the FMOD-P, FMOD, and/or TGF-β isoform dissolved in a pharmaceutically acceptable carrier, such as an aqueous carrier for water-soluble peptides. A variety of carriers can be used, e.g., buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of FMOD-P, FMOD, and/or TGF-β isoform in these formulations can vary widely, and will be selected primarily based on fluid volumes, viscosities, body weight and the like in accordance with the particular mode of administration selected and the patient's needs.

The dosage regimen will be determined by the clinical indication being addressed, as well as by various patient variables (e.g. weight, age, sex) and clinical presentation (e.g. extent of injury, site of injury, etc.).

However, a therapeutically effective dose of a FMOD-P, FMOD, and/or TGF-β isoform useful in this invention is one which has a positive clinical effect on a patient or desired effect in cells as measured by the ability of the agent to impart a beneficial effect to a body condition. The therapeutically effective dose of each peptide or agent can be modulated to achieve the desired clinical effect, while minimizing negative side effects. The dosage of the peptide or agent can be selected for an individual patient depending upon the route of administration, severity of the disease, age and weight of the patient, other medications the patient is taking and other factors normally considered by an attending physician, when determining an individual regimen and dose level appropriate for a particular patient.

Dosages

Dosages of FMOD-P, FMOD, and/or TGF-β isoform can be determined according to methods known in the art based on type of agent, the disease, and other factors such as age and gender.

In one embodiment, the dosage of FMOD-P, FMOD, and/or TGF-β isoform generally ranges from 0.001 pg/mm$^2$ to 1 pg/mm$^2$, or more preferably from 0.001 ng/mm$^2$ to 1 ng/mm$^2$, or more preferably from 0.001 µg/mm$^2$ to 1 pg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage of FMOD-P, FMOD, and/or TGF-β isoform generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage of FMOD-P, FMOD, and/or TGF-β generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

Dosage Form

The therapeutically effective dose of an agent included in the dosage form can be selected by considering the type of agent selected and the route of administration. The dosage form can include an agent in combination with other inert ingredients, including adjutants and pharmaceutically acceptable carriers for the facilitation of dosage to the patient, as is known to those skilled in the pharmaceutical arts.

In one embodiment, the invention can include a method of treating, preventing, or ameliorating (improving) a body condition, comprising administering to a patient a FMOD-P, FMOD, and/or in a therapeutically effective dose in an effective dosage form at a selected interval to improve a body condition.

Method of Use

In another aspect, the present invention provides a method of using the FMOD-P or composition disclosed herein for treating, preventing, or ameliorating a body condition. The method comprises applying FMOD-P or composition disclosed herein to a patient having such a body condition. Such body conditions can be any condition where modulation of TGF-β activities imparts a beneficial effect on the body condition, e.g., diseases such as excessive fibrosis or scar formation that are associated with high TGF-β expression, hypertrophic scars, keloids, radiation fibrosis, fibrotic conditions in organs systems other than skin conditions, such as, but not limited to lung (pulmonary fibrosis) (Gharaee-Kermani, Hu et al. 2009), liver, kidney, cornea, intra-abdominal, gastrointestinal, urological, neurological, or cardiovascular conditions. In addition, there may be other conditions in which modulation of TGF-β activities imparts a beneficial effect on the body condition through modulation of cell proliferation, cell migration, connective tissue growth factor (CTGF) expression and cell aggregation, α-SMA expression, and extra cellular matrix (ECM) organization by FMOD-P or composition disclosed herein.

The FMOD-P or a composition disclosed herein can be also effective for modulating collagen assembly. We have demonstrated that FMOD is also required for proper dermal collagen architecture and that FMOD null animals exhibit profound alterations in collagen ultrastructure as assessed by transmission electron microscopy and in collagen architecture as assessed by confocal laser scanning microscopy and by light microscopy (Khorasani, Zheng et al. 2010).

EXAMPLES

The embodiments of the present invention will be illustrated by the following set forth examples. All parameters and data do not limit the scope of the embodiments of the invention Example 1

Studies on Binding Site Regulation Process of FMOD on TGF-β

Recombinant FMOD Production

Figure 1:
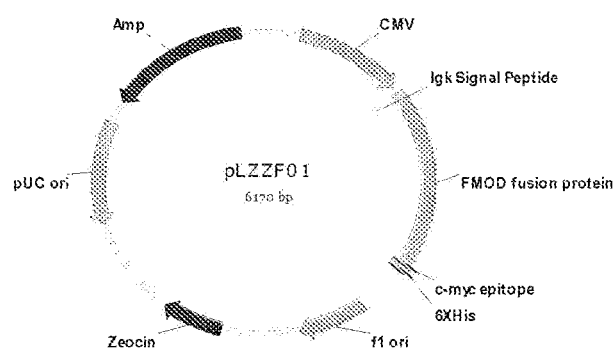
FIG. 1 shows Plasmid pLZZF01.
Figure 2:
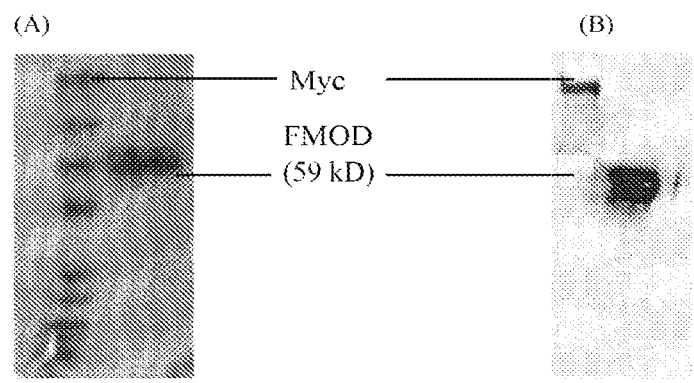
FIG. 2 shows the identification of recombinant FMOD by SDS-PAGE (A) and Western blotting (B).

DNA fragment coding human FMOD (SEQ ID NO:1) was obtained from human FMOD cDNA by PCR and inserted into the commercial vector pSecTag2A (Invitrogen) to yield plasmid pLZZF01 (FIG. 1). FMOD coding gene was under the control with CMV promoter and fused with Igκ signal peptide at N-terminal and c-Myc epitope and 6×His tag at C-terminal. The plasmid pLZZF01 was transformed into Chinese hamster ovarian cell line CHO-K1. The stable transfected cell line was cultured in F12-K medium containing 10% fetal bovine serum (FBS) and 300 µg/ml Zeocin. FMOD recombinant protein was isolated by Probond Purification System (Invitrogen) and dissolved in 1×PBS buffer. Recombinant FMOD was identified by SDS-PAGE and Western blotting with anti-FMOD antibody (FIG. 2).

Figure 3:
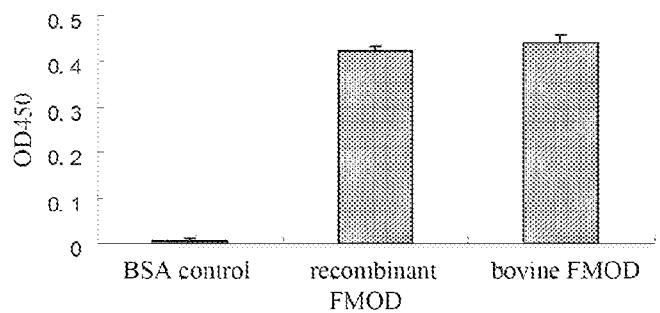
FIG. 3 shows the ELISA analysis of FMOD binding with TGF-β1.

Recombinant FMOD obtained from CHO-K1 was found to be able to bind with TGF-β1 as well as native extract bovine FMOD in ELISA assay (FIG. 3) (Hildebrand, Romaris et al. 1994). Bovine serum albumin (BSA) was used as negative control.

Figure 4:
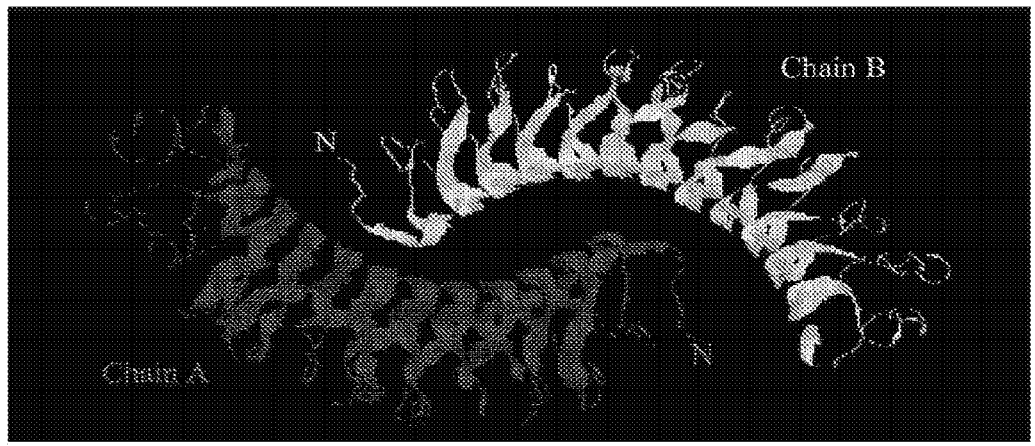
FIG. 4 shows the dimeric bovine tissue-extracted decorin, crystal form 2 (1xec).

Three Dimensional (3D) Structure Prediction of FMOD 3D structure of FMOD was predicted employing 3D-Jigsaw server. Dimeric bovine tissue-extracted decorin, crystal form 2, Chain A (1xec_A, FIG. 4) (Scott, McEwan et al., 2004) was used as the template.

FIG. 5 presents the structural alignment of human FMOD (SEQ ID NO:67) and the template—dimeric bovine tissue-extracted decorin, crystal form 2, chain A (1xec_A: SEQ ID NO:68).

Figure 7:
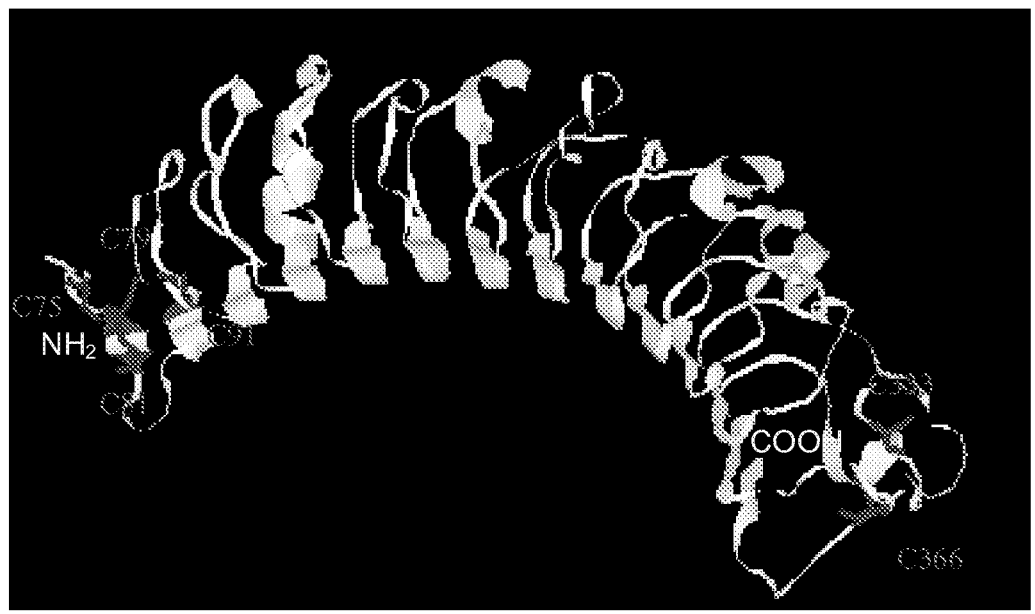
FIG. 7 shows the predicted 3D structure of recombinant human FMOD (AA 71-375). Red: cysteines could build disulfide binds.
Figure 8:
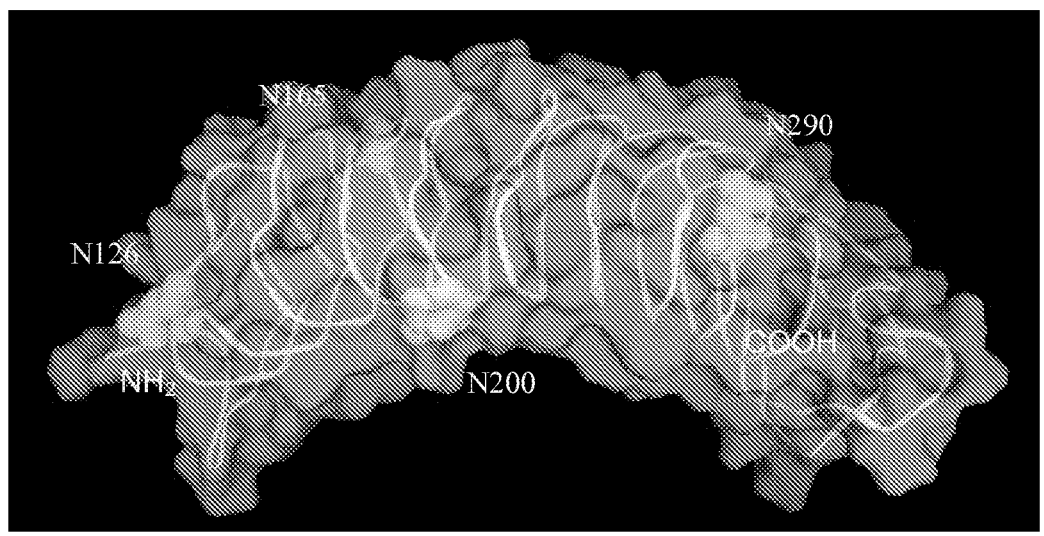
FIG. 8 shows the predicted 3D structure of recombinant human FMOD (AA 71-375) with molecular surface prediction, which was based on the Conolley Method. Yellow: N-glycoside points.

FIG. 6 presents the predicted 3D structure of human FMOD protein (AA 71-375). Due to the low structural homology, no template can be found to predict the 3-D structure of the N-terminal fragment. FIG. 7 highlights the cysteines which build disulfide binds. Using commercial software Vector NTI 9.0, the predicted molecular surface based on Conolly method (Connolly 1993) was shown in FIG. 8. N-glycoside points were also highlighted in this structure (FIG. 8) (Plaas, Neams et al. 1990).

Figure 9:
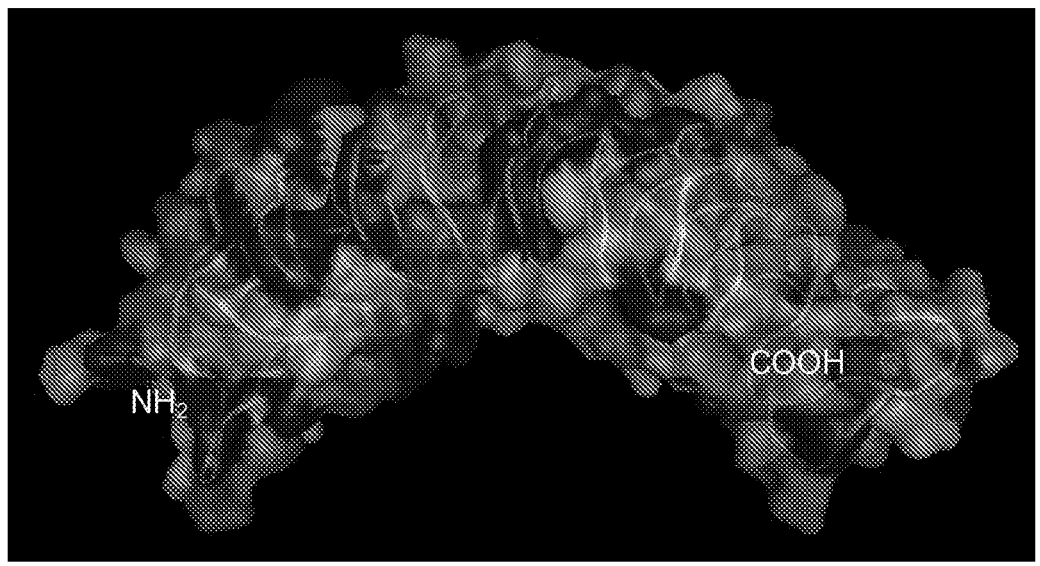
FIG. 9 shows the predicted 3D structure of recombinant human FMOD (AA 71-375) with hydrophobicity. The hydrophobicity is increased from blue to red.
Figure 10:
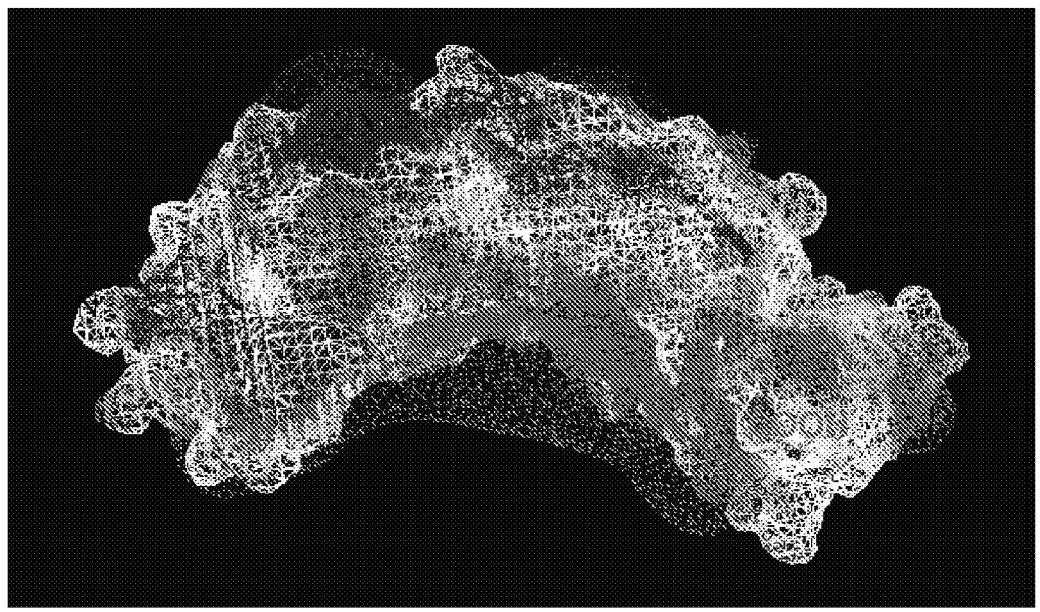
FIG. 10 shows the predicted 3D structure of recombinant human FMOD (AA 71-375) with electrostatic potential based on Coulomb method. Red: negative charged; blue: positive charged.

Hydrophobicity of the FMOD was also analyzed by Vector NTI (FIG. 9). While, electrostatic potential of FMOD was predicted by software Spdbv using Coulomb Method (FIG. 10) (Abagyen, Totrov et al. 2004).

Construct the Plasmids Harboring Different Fragments of FMOD

Figure 11:
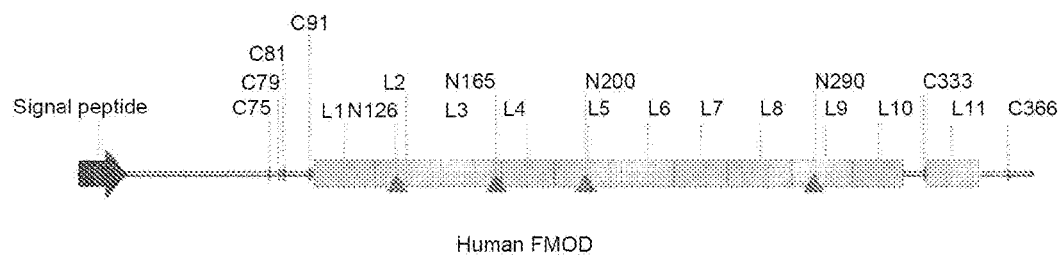
FIG. 11 shows the primary structure of human FMOD. C: Cysteines to build disulfide bind; N: N-glycoside points; L.

The first structure of human FMOD was shown in FIG. 11. Employing PCR method, DNA fragments encoding different part of human FMOD were inserted into commercial vector pET_SUMO (Invitrogen) to yield various plasmids pLZZF01-pLZZF040. For instance pLZZF09 (harboring LRR5, LRR6 and LRR7 of human FMOD), pLZZF10 (harboring LRR8, LRR9 and LRR10 of human FMOD), and pLZZF11 (harboring C-terminal of human FMOD including LRR11), respectively. The target peptides were fused with N-terminal SUMO and G-6×His tag.

The fused target peptide-SUMO plasmids (e.g., pLZZF09) were transformed into *Escherichia coli* BL21 (DE3) strain as well as the control plasmids pET_SUMO/CAT. Recombinant bacteria were cultured in LB medium containing 100 mM IPTG to produced SUMO-fusion protein. Fusion proteins were purified by Probond Purification System (Invitrogen) and dissolved in 1×PBS buffer.

Example 2

Binding Studies on FMOD-P

SUMO-Fused FMOD Fragments Binding with TGF-βI

Employing ELISA method, some SUMO-fused FMOD peptide fragments were found to be able to bind with TGF-β1 (SEQ ID NO: 20) (FIG. 12) (Hildebrand, Romaris et al. 1994). SUMO-CAT from the recombinant bacteria harboring control plasmid pET_SUMO/CAT was used as negative control. To the knowledge of inventors, the TGF-binding sites within FMOD have not been reported.

Example 3

Studies Relative Binding Affinities of Invention FMOD Peptides F06 and F07 to the Different TGF-β Isoforms Binding of FMOD and FMOD Peptides with TGF-β Isoforms FMOD (whole protein) (SEQ ID NO:1), FMOD peptides and control protein BSA were biotinylated. While, the biotinylated proteins and peptides were bound to commercial available Piece Monomeric Avidin UltraLink Resin (Piece). The amounts of each test peptides/proteins are 1:1, 10:1, 100:1 and 1000:1 to TGF-βs, respectively. After washing out the non-bound residues, appropriate amount TGF-βs (based on the primary test assay) were added to the resin at 4° C. After overnight binding, non-bound TGF-βs were collected, followed by filter sterilization. Then, the TGF-βs residue were diluted 100 times in DEME-0.5% FBS to ensure the concentration was located in the linear region of TGF-βs on Mv1Lu proliferate inhibition.

Diluted TGF-βs was added to overnight serum-starved Mv1Lu, and fresh TGF-βs media were added for another 24 hour before MTT assay. Samples with no TGF-βs added were employed as controls. From the results of Mv1Lu growth inhibition, the binding radio of TGF-β1 (SEQ ID NO:64) are shown in FIG. 13.

The results show that control BSA demonstrated minimal TGF-β1 binding except at very high ratios (1000:1 mol/mol). FMOD protein demonstrated TGF-β1 binding that also increased with higher FMOD protein ratios. Unexpectedly, some FMOD peptides demonstrated significantly greater TGF-β1 binding than FMOD at some of the ratios tested. The significance of the results is even more striking given the relatively low purity of the FMOD peptides. It is anticipated that even greater TGF-Ø1 binding will be obtained with more highly purified FMOD peptides.

The binding activity of TGF-β2 (SEQ ID NO:65) are shown in FIG. 14.

Similar as to TGF-β1, control BSA demonstrated minimal TGF-β2 binding. FMOD protein demonstrated TGF-β2 binding that also expectedly increased with higher FMOD protein ratios—although not to as great a degree as TGF-β1. Unexpectedly, some FMOD peptides demonstrated significantly greater TGF-β2 binding than FMOD at some of the ratios tested. The significance of these results is even more striking given the relatively low purity of the FMOD peptides. It is anticipated that even greater TGF-β2 binding will be obtained with more highly purified FMOD peptides. Also surprisingly, the peptide FMOD-F06-C40 does not bind TGF-β2. This indicates that F06-C40 can selectively bind TGF-βI and not TGF-β2.

The binding activity of TGF-β3 (SEQ ID NO:66) is shown in FIG. 15.

In FIG. 15, BSA did not bind to TGF-β3 even at high ratios. FMOD protein demonstrated TGF-β3 binding that also expectedly increased with higher FMOD protein ratios up to 1:100—although to a significantly lesser degree than TGF-β1 or TGF-β2 (i.e., FMOD binds TGF-β1>TGF-β2>TGF-β3). Unexpectedly, some novel FMOD peptides demonstrated significantly greater TGF-β3 binding than FMOD at some of the ratios tested.

In summary these novel data demonstrate that we have created novel FMOD peptides F07 and F07-C40 that can bind all three TGF-β isoforms TGF-β2 and TGF-×3) more effectively than FMOD whole protein. We have also created novel FMOD peptides that can selectively bind TGF-β1 and TGF-β3 more effectively than FMOD whole protein.

The different binding characteristics of the FMOD related peptides F06-C40 vs. F07/F07-C40 for different TGF-β isoforms indicates that FMOD has at least two binding sites for TGF-β and that the two binding sites of FMOD have different binding affinities to TGF-β isoforms. It also suggests that the two different TGF-β binding sites of FMOD may have different effects or interactions with TGF-β ligands. Overall, these data indicate that FMOD peptides can exhibit different interactions with TGF-β ligands that was previously impossible to distinguish on the FMOD whole protein.

From a clinical standpoint, these results indicate that novel FMOD peptides can modulate TGF-β activity in a novel fashion than FMOD whole protein.

Example 4

Studies on Combination of TGF-β Combined with FMOD or FMOD Peptides

Introduction

The effect of TGF-β isoforms alone or of FMOD alone on cell proliferation has been described. However, the novel concept of using FMOD and TGF-β isoforms to modulate cell proliferation has not been described. Furthermore, the novel concept of using FMOD peptides and TGF-β isoforms to modulate cell proliferation has also not been described TGF-β Combined with FMOD or FMOD Peptides on Cell Proliferation 2000 cell/well passage 18 Rat-2 (rat fibroblast cell line) cells were seeded in 96-well plates with 200 μl DMEM-10% FBS for 6 hours, followed by overnight serum starving with 200 μl DMEM-0.5% FBS. 200 μl treatment medium, DMEM-0.5% FBS harboring different concentration of FMOD (SEQ ID NO:1), FMOD-F07-C40 peptide with/without 100 pM TGF-βI (SEQ ID NO:64), was added to the well and refreshed on the second day. After 48 hours treatment, proliferation of Rat-2 cells was evaluated by Click-iT® Microplate Assay (Invitrogen). Results using FMOD (whole protein) are shown in FIG. 16.

Unexpectedly, combination of FMOD and TGF-β1 significantly increased fibroblast proliferation. This is a novel finding that can be applied to chronic wounds (e.g., diabetic foot ulcers) to accelerate healing.

Results using F07-C40 are shown in FIG. 17A and repeat results in FIG. 17B.

Even more unexpectedly, combination of F07-C40 and TGF-β1 increased fibroblast proliferation at low F07-C40 doses but in marked distinction to the FMOD whole protein, F07-C40 significantly inhibited fibroblast proliferation at moderately high doses, and decreased cell viability at high doses. This is a novel finding that combination F07-C40 and TGF-β1 can be modulated so that low F07-C40 doses are used for situations in which increased cell proliferation are desired (e.g., chronic wounds) and moderately high F07-C40 doses are used for situations in which decreased cell proliferation are desired (e.g., hypertrophic scars) and high F07-C40 doses are used for situations in which decreased cell viability are desired (e.g., keloids).

On the other hand, another peptide F06-C40 also exhibits the ability to induce fibroblast proliferation (FIG. 17C).

From a clinical standpoint, these results indicate that FMOD combined with TGF-13 can potently induce cell proliferation. Thus, it can be used to treat a large variety of impaired or deficient wound healing conditions. In contrast novel FMOD peptides combined with TGF-β can promote cell proliferation at low FMOD peptide doses and inhibit cell proliferation at moderately high FMOD peptide doses and decrease cell viability at high FMOD peptide doses. Inhibition of cell proliferation and promotion of decreased cell viability can be especially desirable in certain conditions with excessive cell proliferation such as hypertrophic scars and keloids (Lim, Phan et al. 2006).

TGF-β Combined with FMOD or FMOD Peptides on Cell Migration

Introduction

The effect of TGF-β isoforms alone on cell migration/chemotaxis, angiogenesis, and extracellular matrix production and remodeling is well known [reviewed in (Roberts and Sporn 1996)]. The effect of combination of FMOD and TGF-β isoforms on cell migration has not been described. The effect of combination of FMOD peptides and TGF-13 isoforms on cell migration has also not been described.

FMOD (Whole Protein)

Figure 18A:
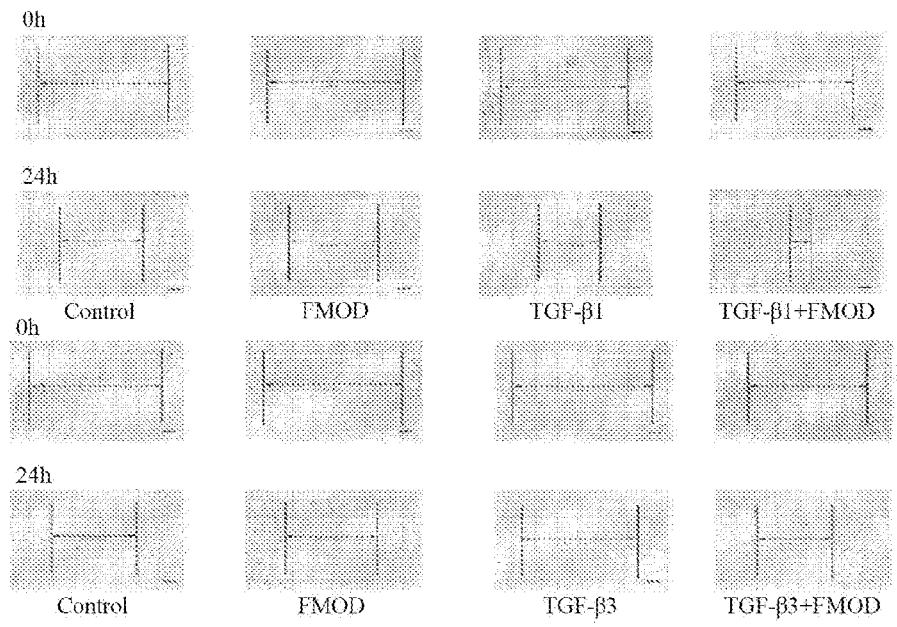

FIG. 18A shows the results of a few examples of tests on the effect of FMOD (SEQ ID NO:1) and/or TGF-β on cell migration. $1 \times 10^6$ cell/well Rat-2 cells were seeded in 6-well plated with 3 ml DMEM-10% FBS. After 6 hours for adhesion, fresh DMEM-0.5% FBS medium was changed for serum-starving overnight. After pre-warmed DMEM rinsing, four wounds (each 1 mm wide; two horizontal and two vertical) were scratched employing a 1-ml tip for each treatment group. Cells were rinsed by DMEM for three times, followed by incubation with treatment medium [DMEM-0.5 FBS containing 100 pM (2.5 ng/ml) TGF-β1 (SEQ ID NO:64) or -β3 (SEQ ID NO:66) w/o 200 nM (11.2 pg/ml) FMOD (SEQ ID NO:1)] for 24 hours. Photos were captured at both 0-h and 24-h after the scratching. The unclosed distance was measured and quantified as an average gap (A) and migration index (B). Similar results were reproduced in four independent experiments. The scale bar in (A) equal to 100 The asterisks in (B) present $P<0.05$.

Figure 18B:
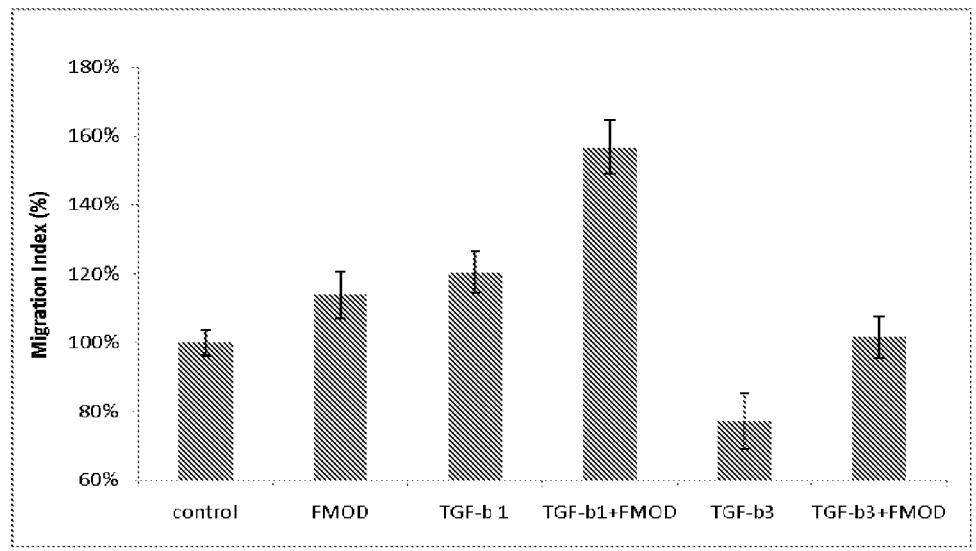

These results show that FMOD alone induced Rat-2 minimal migration, while surprisingly, combination of FMOD and TGF-β1 induced significant migration (FIG. 18B). In contrast, TGF-β3 inhibited migration, while combination of FMOD and TGF-β3 decreased TGF-β3 mediated inhibition of migration.

Figure 19A:
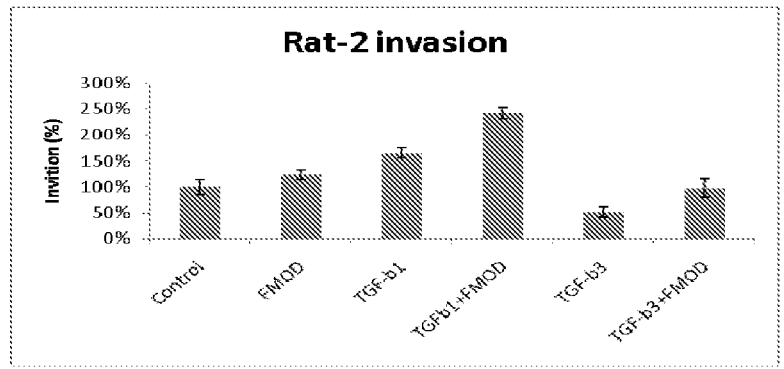
Figure 19B:
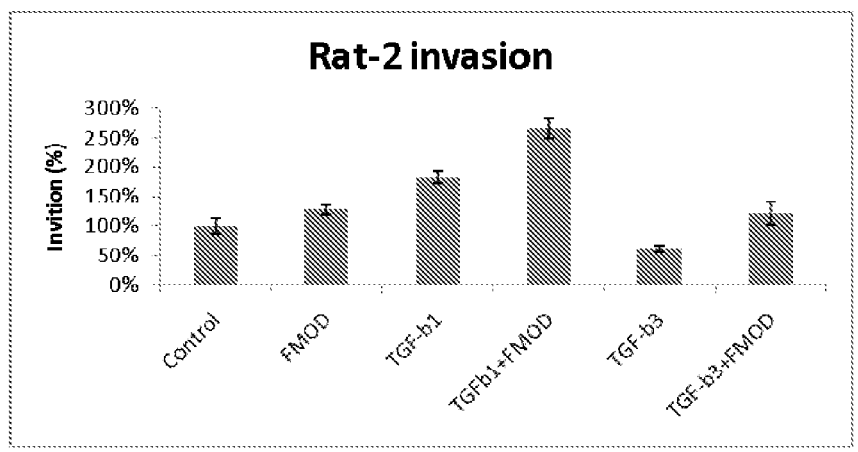
Figure 19C:
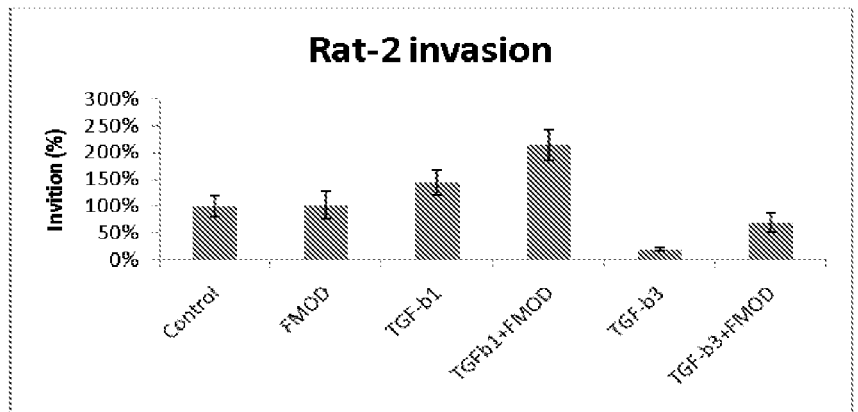
Figure 19D:
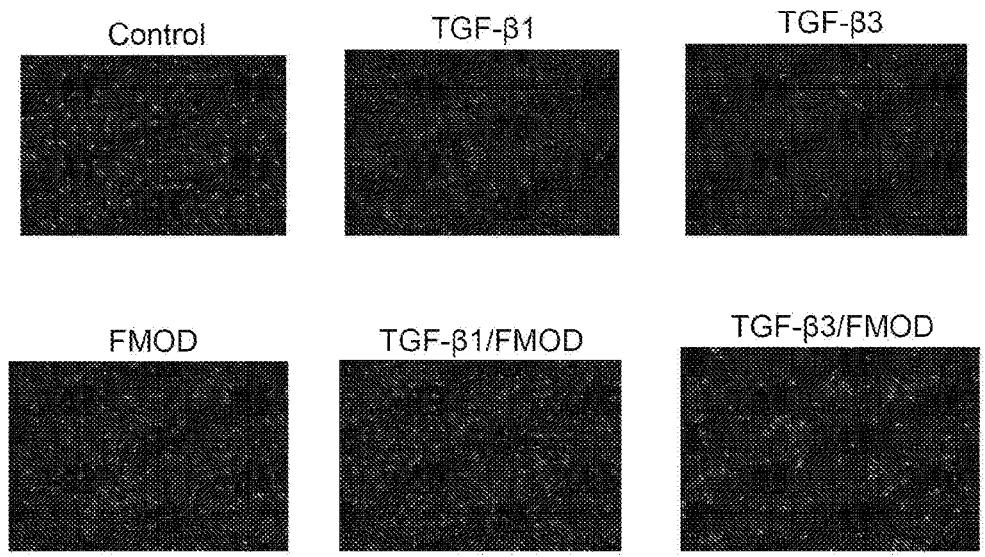

Cell migration/invasion in Matrigel was documented at 200× magnificent after 24 hour treatment and quantitated using DAPI nuclear staining (results shown in FIG. 19A and repeat results in FIGS. 26B and 26C; DAPI pictures are shown in FIG. 19D). FMOD alone induced Rat-2 moderate migration, while surprisingly, combination of FMOD and TGF-β1 also induced significant migration. In contrast, TGF-β3 inhibited migration, while combination of FMOD and TGF-β3 decreased TGF-β3 mediated inhibition of migration.

These results indicate that FMOD augments the cell migration effects of TGF-β1, while FMOD decreases the inhibitory cell migration effects of TGF-β3.

FMOD Peptides

Figure 18C:
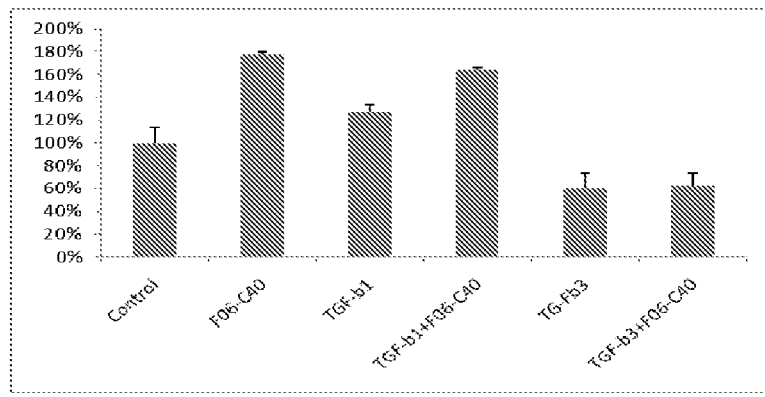
Figure 18D:
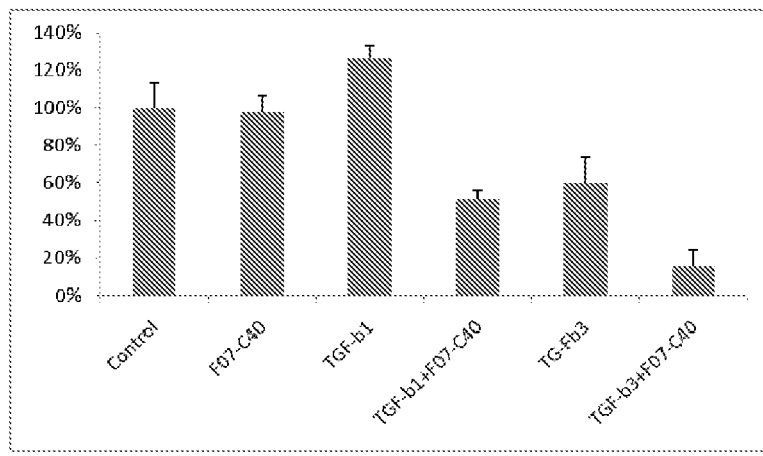

Similar to FMOD (whole protein), the effect of FMOD peptides and/or TGF-β on cell migration was also evaluated by scratching method (FIGS. 18C and 25D). At the same time, cell migration/invasion in Matrigel was documented at 100× magnificent after 24 hour treatment and quantitated using DAPI nuclear staining (100 rather than 200× magnification was used because one group's invasion is quite low) (see the results in FIG. 20A and DAPI pictures in FIG. 20B). Passage 18 Rat-2 cells (20,000 cells/well) were used for the test under the treatment of 100 pM TGF-β1 (SEQ ID NO:64)/β3 (SEQ ID NO:66) with/without 200 nM FMOD-F07-40C in DMEM-0.5% FBS.

F07-C40 alone did not induce significant Rat-2 migration, while completely unexpectedly, combination of F07-C40 and TGF-β1 significantly inhibited TGF-β1 mediated Matrigel migration. This activity of F07-C40 is completely the opposite of FMOD whole protein which increased cell migration effects of TGF-β1. Also remarkably, while TGF-β3 expectedly inhibited migration, combination of F07-C40 and TGF-β3 increased TGF-β3 mediated inhibition of migration. This activity of F07-C40 is also completely the opposite of FMOD whole protein which decreased the inhibitory cell migration effects of TGF-β3.

Figure 20A:
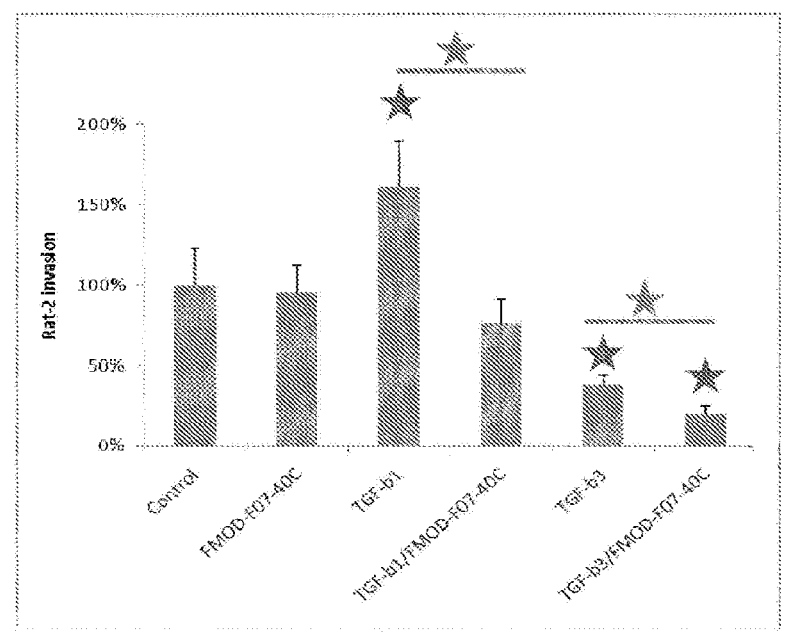
Figure 20B:
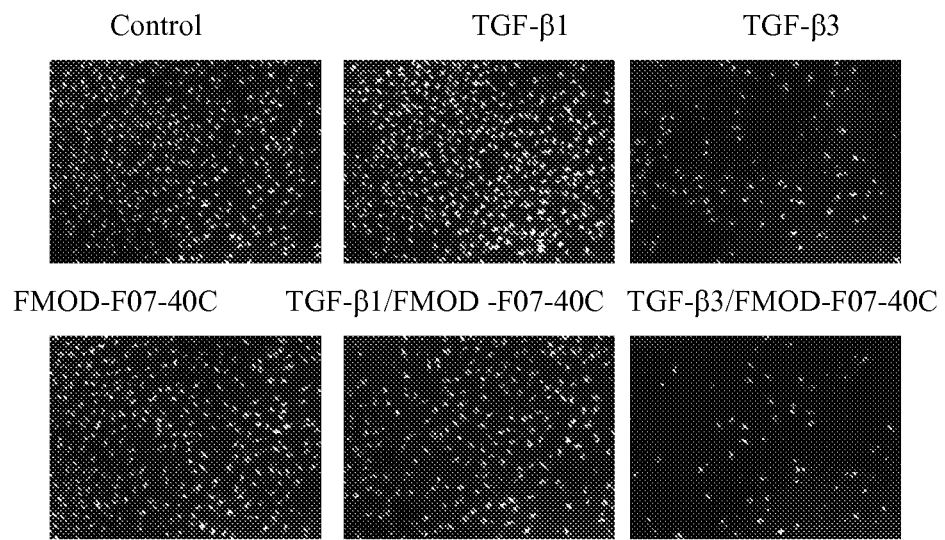
Figure 20C:
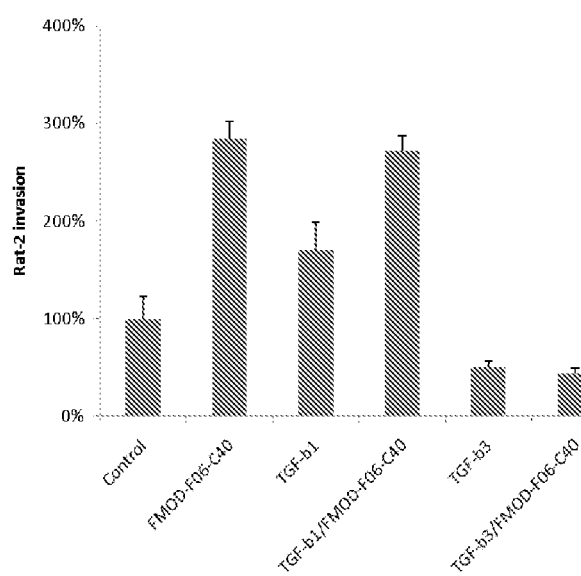
Figure 20D:
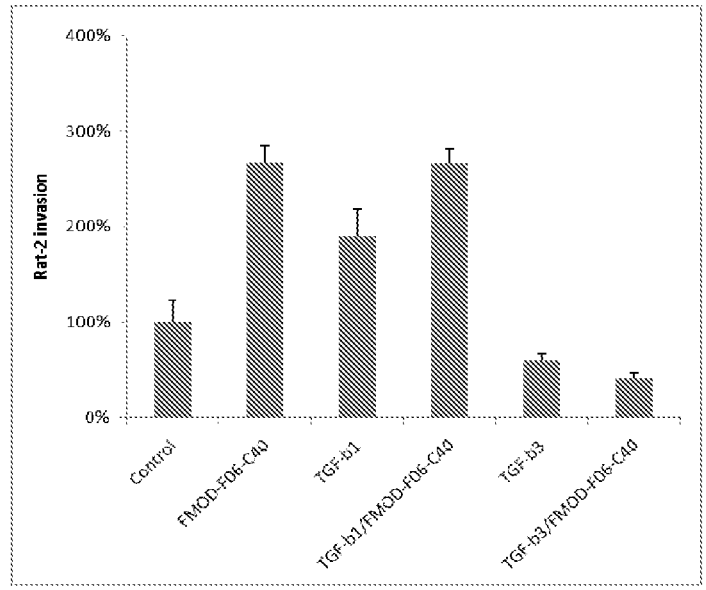
Figure 20E:
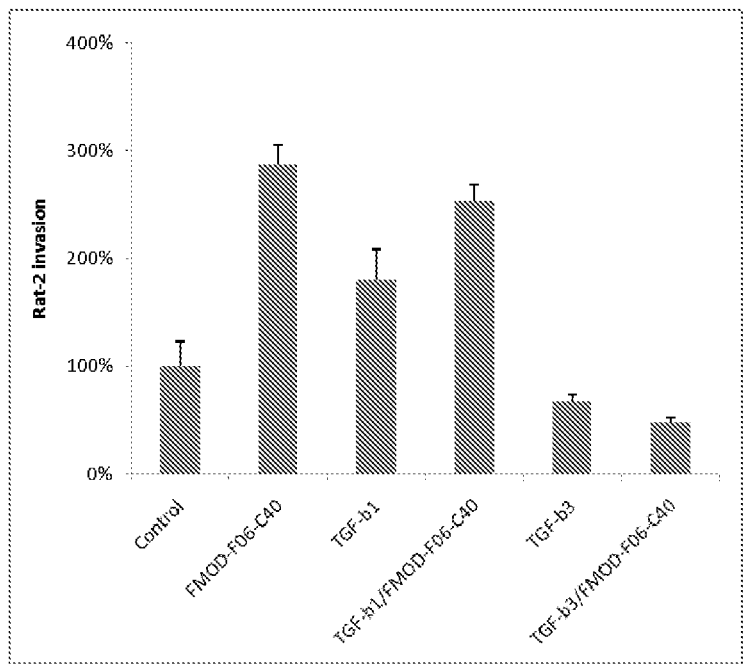

Passage 18 Rat-2 cells (20,000 cells/well) were used for the test under the treatment of 100 pM TGF-β1/β3 with/without 200 nM FMOD-F06-40C in DMEM-0.5% FBS (FIG. 20C). Repeat results were shown in FIGS. 20D and 27E. Surprisingly, FMOD-F06-40C promotes fibroblasts migration regardless TGF-β1 exists or not. However, FMOD-F06-40C could not eliminate the inhibition of TGF-β3 on fibroblast migration.

These data demonstrate that, when combined with TGF-β, FMOD peptides can demonstrate distinct different biological effects than FMOD whole protein. This difference can be used to regulate cell migration.

From a clinical standpoint, F07-C40 inhibition of TGF-β1 mediated cell migration in Matrigel demonstrates that F07-C40 can be used prevent tumor cell migration/metastasis (Muraoka, Dumont et al. 2002; Yang, Dukhanina et al. 2002) in situations with high basal TGF-β1. Alternatively, combined F07-C40 and TGF-β3 can be used even more effectively inhibit cell migration. In addition, FMOD can be added to promote cell migration in situations where cell migration is inhibited by high TGF-β3.

Example 5

Studies on FMOD and TGF-β or FMOD Peptides and TGF-β on CTGF Expression and Cell Aggregation Introduction TGF-β1 is a potent stimulator of connective tissue growth factor (CTGF) expression in cells such as fibroblasts and endothelial cells. CTGF has biological effects similar to TGF-β1, and CTGF has been shown to act as an essential downstream mediator of TGF-β1 [reviewed in (Song, Aswad et al. 2007)]. Although the effect of TGF-β1 on inducing CTGF expression has been described, using FMOD and TGF-β isoforms to modulate CTGF expression has not been described. Furthermore, using FMOD peptides and TGF-β isoforms to modulate CTGF expression also has not been described. Also, the effect of FMOD or FMOD peptides alone, FMOD and TGF-β, or FMOD peptides and TGF-β on cell morphology has not been described.

Results of exemplary tests on each of FMOD and FMOD-P, alone or in combination with TGF-β on CTGF expression are shown in FIGS. 28A-28D. In these tests, 4,000 cells/well passage 18 Rat-2 cells were seeded in 8-well chamber slices in DMEM medium with 10% FBS. After 6 h adhesion, fresh DMEM medium with 0.5% FBS was employed for overnight serum starvation and then treatment media added. Treatment media were changed after 24 h. Cells were fixed and staining at 48 h. Photos were captured at 630× magnifications using a confocal microscope. In these figures, the cells were stained for CTGF (connective tissue growth factor, a factor involved in cell proliferation, migration and matrix production) or DAPI (4',6-diamidino-2-phenylindole a fluorescent stain that binds strongly to DNA-used for nuclear staining). Merged images showing both CTGF and DAPI staining are also shown.

Figure 21A:
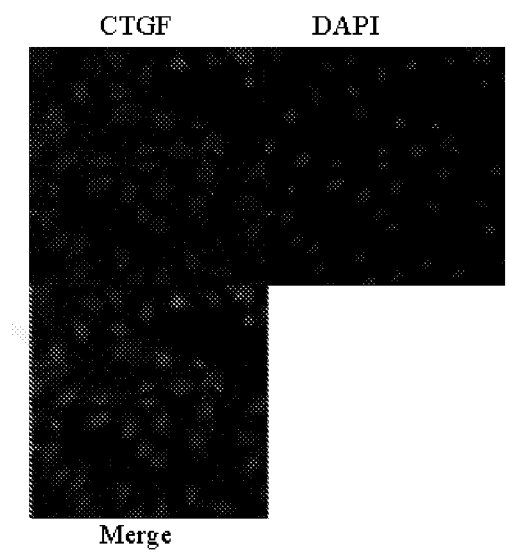

The results of control tests are shown in FIG. 21A. Minimal CTGF expression is present in controls.

Figure 21B:
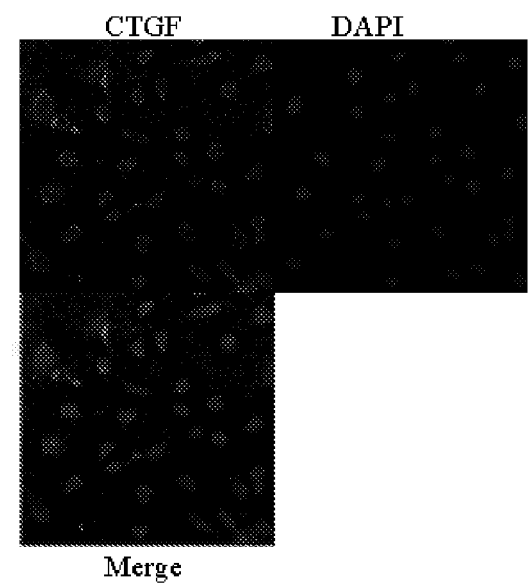

Results from 200 nM FMOD (SEQ ID NO:1) treatment are shown in FIG. 21B. Minimal CTGF expression is present in FMOD treated samples. FMOD treated Rat-2 cells appeared more flat and spread out when compared to the control group. Thus, FMOD alone may inhibit cell aggregation.

Figure 21C:
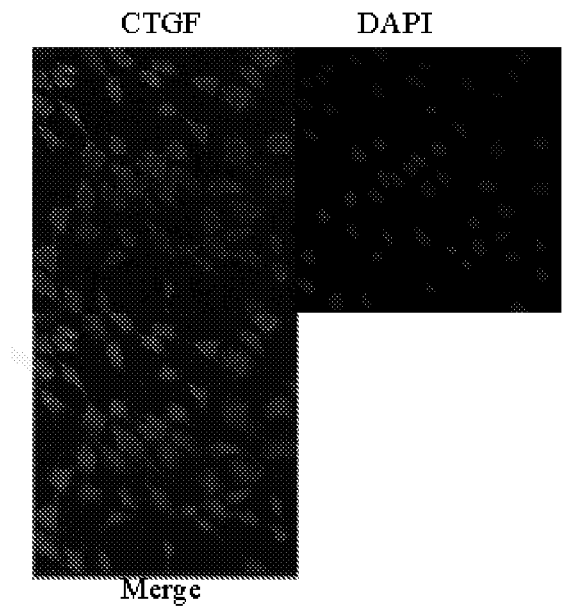

Results from 100 pM TGF-β1 (SEQ ID NO:64) treatment are shown in FIG. 21C. The data show that moderate CTGF expression is present in TGF-β1 treated samples.

Figure 21D:
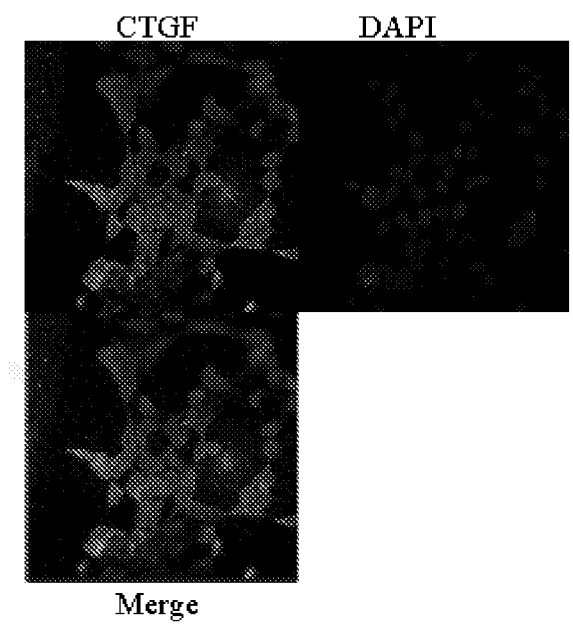

Results from 100 pM TGF-β1+200 nM FMOD treatment are shown in FIG. 21D.

FIGS. 21A-21D show that, unexpectedly, significantly higher CTGF expression is present in FMOD and TGF-β1 treated samples. This is also accompanied by significant cell aggregation.

H&E Morphology of Rat-2 Cells after FMOD, TGF-β1, or FMOD and TGF-β1 Treatment

Exemplary tests were performed to better delineate cell morphology. FIG. 22 shows the results from treatment by combinations of FMOD (SEQ ID NO:1) (0, 200 nM) and TGF-β (SEQ ID NO:20) (0, 100 nM).

FIG. 22 shows that 200 nM FMOD treatment resulted in a flat, spread-out Rat-2 cell morphology as well as lower cell aggregation/density relative to controls. Meanwhile, 100 pM TGF-β1 treat slightly increased the Rat-2 cell density, along with induction of small nodule-like cell aggregations/condensations that were observed rarely (<one nodule/well in 8-well chamber slides). Unexpectedly, 100 pM TGF-β1 and 200 nM FMOD combined treatment resulted in significantly increased cell density as well as increased nodule size and nodule number (about four nodules/well of 8-well chamber slides). These data confirm that FMOD can affect cell density, aggregation, and morphology.

Other Studies

Effects of FMOD, alone or in combination with TGF-β on expression of CTFG were repeated in a few more tests. The results are shown in FIGS. 23A-23E.

FIG. 23A shows the results from 2-day control treatment.

FIG. 23B shows the results from 2-day FMOD (SEQ ID NO:1) mono-treatment.

FIG. 23C shows the results from 2-day TGF-β1 (SEQ ID NO:64) mono-treatment.

FIG. 23D shows the results from 2-day FMOD+TGF-β1 combo-treatment.

FIG. 23E shows a comparison chart of the results in FIGS. 23A-23D, respectively.

In another set of similar studies, we see that TGF-β1 treatment increases expression of CTGF (green fluorescence), while TGF-β1/FMOD combo-treatment significantly increases expression of CTGF (green fluorescence) relative to TGF-β1 mono-treatment (FIG. 24). From a cell morphology standpoint, it can be seen that TGF-131/FMOD combo-treatment results in much more densely packed, aggregated cells with a significant degree of nodule formation (yellow arrows).

We then performed Z-axes series sequential images to determine the relative height of the nodules as shown in FIG. 24.

As can be seen from FIG. 24, under control or mono-treatment condition (TGF-0.131 or FMOD alone), Rat-2 fibroblasts maintained single layer cell morphology (no signals were observed above 8 μm height). But for the nodules formed with FMOD and TGF-β1 treatment (yellow arrows), the cells were stacked on top of one another to a height of about 48 μm. Interestingly, more CTGF expression was noted at the base of the nodule than at the top of the nodule.

From a clinical standpoint, the ability to control cell aggregation and density can be critical for many processes such as cartilage or bone formation (Song, Aswad et al. 2007) and wound healing. For example, FMOD and TGF-β1 can be used to promote mesenchymal condensations for cartilage regeneration.

Example 6

Studies on Effect of FMOD and TGF-β or FMOD Peptides and TGF-β on α-SMA Expression Introduction TGF-β profibrotic growth factor that regulates fibroblast proliferation, myofibroblast differentiation, and causes increased collagen deposition during fibrosis (Gharaee-Kermani, Hu et al. 2009). Myofibroblasts are specialized fibroblastic cells that appear during wound healing and in a variety of fibrocontractive diseases where they exert a significant contractile activity; they are characterized by well-developed microfilament bundles, which are analogous to stress fibers of fibroblasts in culture [reviewed in (Hinz, Dugina et al. 2003)]. In contrast, resident tissue fibroblasts do not exhibit such a contractile apparatus. On stimulation with TGF-β myofibroblasts express de novo α-smooth muscle actin (α-SMA); and form specialized adhesion structures with the ECM that are called fibronexus in vivo or "supermature" focal adhesions (FAs) in vitro [reviewed in (Hinz, Dugina et al. 2003)]. Although α-SMA expression is a prototypical myofibroblast feature (Eyden, Banerjee et al. 2009) and is correlated with contractile force generation (Tomasek, McRae et al. 2005), there is evidence that α-SMA absence can cause greater fibrotic response (Takeji, Moriyama et al. 2006). Specifically, α-SMA presence has been shown to decrease renal tissue fibrosis as well as suppress cell proliferation, procollagen synthesis, cell migration, and FA proteins (Takeji, Moriyama et al. 2006). Thus, therapies that increase α-SMA expression early on can suppress cell proliferation, procollagen synthesis, cell migration, and FA proteins—leading to overall less fibrosis. Although the effect of TGF-β1 on inducing α-SMA expression has been described, the novel concept of using FMOD and TGF-β isoforms to modulate α-SMA expression has not been described. Furthermore, the novel concept of using FMOD peptides and TGF-β isoforms to modulate α-SMA expression also has not been described.

Exemplary tests on effects of FMOD and TGF-β or FMOD peptides and TGF-β on α-SMA expression were performed and shown in FIGS. 25A-25D. Expression levels of α-SMA, which is a marker for the transition of fibroblasts to myofibroblasts, were measured and presented in staining in these figures.

FIG. 25A shows the results from control tests, which shows minimal α-SMA staining.

FIG. 25B shows the results from 200 nM FMOD (SEQ ID NO:1) treatment, which shows minimal α-SMA staining.

FIG. 25C shows the results from 100 pM TGF-β1 (SEQ ID NO:64) treatment, which shows moderate α-SMA staining.

FIG. 25D shows the results from 100 pM TGF-β1+200 nM Fibromodulin treatment, which shows significantly increased α-SMA staining accompanied by increased cell density/cell aggregation.

Overall, these studies demonstrate that FMOD (or FMOD peptides) and TGF-β can significantly promote α-SMA expression. Depending on the time frame FMOD (or FMOD peptides) and TGF-β are applied, it can be used to suppress cell proliferation, procollagen synthesis, cell migration, and FA proteins (applied earlier) or promote contraction (applied later).

From a clinical standpoint, early FMOD (or FMOD peptides) and TGF-β application can be used to decrease fibrosis, while late FMOD (or FMOD peptides) and TGF-β application can be used to promote contraction to decrease the size of open wounds.

Example 7

Studies on Effect of FMOD Peptides on ECM Organization

Introduction

Scar formation is the undesirable sequelae of adult-type tissue repair through fibroplasia rather than regeneration. Radiation-induced fibrosis or scar formation is a common sequela after therapeutic irradiation of head and neck cancers. A scar is comprised of a disorganized collection of collagen and other ECM components with interspersed dermal cells (primarily fibroblasts, myofibroblasts). We created novel FMOD peptides that exhibit significant effects on collagen fibrillogenesis and ECM organization by both qualitative and quantitative analyses. Thus, novel FMOD peptides can be used to reduce fibrosis and to promote more organized ECM architecture in conditions such as healing wounds, radiation fibrosis, and scleroderma.

Skin tissues were collected from pigs at 4 weeks post injury, 630×. Sample A is a control which is an unwounded skin tissue. Sample B is another control which is a wounded, but untreated skin tissue. Sample C is a wounded tissue treated by a FMOD-P at a concentration of 0.5 mg/ml. Sample D is a wounded tissue treated by a FMOD-P at a concentration of 2.0 mg/ml.

Healing by primary intention wounds were observed. The results are shown in FIGS. 26A-26B. FIG. 26B shows the fractal dimension of the control and treated tissues. Fractal dimension (higher $F_D$) provides a measure of how completely an object fills space and increases in value with increasing structural complexity (Smith, Lange et al. 1996). It has a value between 1 and 2. Lacunarity (L) is a measure of the non-uniformity (heterogeneity) of a structure or the degree of structural variance within an object (Smith, Lange et al. 1996). Therefore, low lacunarity objects are homogeneous because all gap sizes are the same, whereas high lacunarity objects are heterogeneous. Lacunarity has a value between 0 and 1 where a minimum value of 0 corresponds to an absolute homogeneous object.

In this study, we have shown that the collagen bundles in scar tissue have significantly denser (higher $F_D$) and significantly more homogeneous architecture (lower L) compared to the basket weaved and randomly organized normal tissue. We have also shown that individual collagen fibrils in scar tissue have much smaller diameter and much more narrow size distribution as compared to normal tissue. In contrast, the FMOD-P treated samples have collagen/ECM architecture that is much closer to unwounded tissue and $F_D$ and L measurements that are not significantly different from unwounded tissue.

These results indicate that FMOD peptide can optimize collagen fibrillogenesis and ECM architecture, especially in the closed wounds (E-wounds). No significance was obtained between 0.5 mg/ml and 2.0 mg/ml treatment in $F_D$ and L analysis. This indicates that FMOD peptides are effective across a wide dose range.

From a clinical standpoint, FMOD peptides can be used to decrease fibrosis in different organ systems such as, but not limited to lung, liver, kidney, skin, and heart.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention

REFERENCES

Abagyan, R., M. Totrov, D. Kuznetsov. (2004) "IM-A new method for protein modeling and design: application to docking and structure prediction from the distorted native conformation." *Journal of Computational Chemistry* 15 (5): 488-506.

Connolly, M. L. (1993) "The molecular surface package" *Journal of Molecular Graphics* 11 (2): 139-141.

Eyden, B., S. S. Banerjee, et al. (2009). "The myofibroblast and its tumours." *J Clin Pathol* 62(3): 236-49.

Gharaee-Kermani, M., B. Hu, et al. (2009). "Recent Advances in Molecular Targets and Treatment of Idiopathic Pulmonary Fibrosis: Focus on TGFbeta Signaling and the Myofibroblast." *Curr Med Chem* 16(11): 1400-17.

Hedbom, E. and D. Heinegard (1989). "Interaction of a 59-kDa connective tissue matrix protein with collagen I and collagen II" *The Journal of Biological Chemistry* 264 (12): 6898-6905.

Heinegard, D., T. Larsson, et al. (1986). "Two novel matrix proteins isolated from articular cartilage show wide distributions among connective tissues." *J Biol Chem* 261(29): 13866-72.

Hildebrand, A., M. Romaris, et al. (1994). "Interaction of the small interstitial proteoglycans biglycan, decorin and fibromodulin with transforming growth factor beta." *Biochem J* 302 (Pt 2): 527-34.

Hildebrand, A., M. Romaris, et al. (1994). "Interaction of the small interstitial proteoglycans biglycan, decorin and fibromodulin with transforming growth factor β." *Biochem. J.* 302: 527-534.

Hinz, B., V. Dugina, et al. (2003). "Alpha-smooth muscle actin is crucial for focal adhesion maturation in myofibroblasts." *Mol Biol Cell* 14(6): 2508-19.

Kalamajski, S. and A. Oldberg (2007). "Fibromodulin binds collagen type I via glu-353 and lys-355 in leucine-rich repeat 11." *Journal of Biological Chemistry* 282(37): 26740-26745.

Khorasani, H., Z. Zheng, et al. (2010). "A quantitative approach to scar analysis." In Submission.

Lim, C. P., T. T. Phan, et al. (2006). "Stat3 contributes to keloid pathogenesis via promoting collagen production, cell proliferation and migration." *Oncogene* 25(39): 5416-25.

Muraoka, R. S., N. Dumont, et al. (2002). "Blockade of TGF-beta inhibits mammary tumor cell viability, migration, and metastases." *J Clin Invest* 109(12): 1551-9.

Plaas, A. H. K., P. J. Neams, et al. (1990). "Identification of the keratan sulfate attachment sites on bovine fibromodulin." *The Journal of Biological Chemistry* 265(33): 20634-20640.

Roberts, A. B. and M. B. Sporn (1996). Transforming growth factor-beta. *The Molecular and Cellular Biology of Wound Repair*. R. A. F. Clark. New York, Plenum Press: 275-308.

Smith, T. G., Jr., G. D. Lange, et al. (1996). "Fractal methods and results in cellular morphology—dimensions, lacunarity and multifractals." *J Neurosci Methods* 69(2): 123-36.

Song, J. J., R. Aswad, et al. (2007). "Connective tissue growth factor (CTGF) acts as a downstream mediator of TGF-beta 1 to induce mesenchymal cell condensation." *J Cell Physiol* 210(2): 398-410.

Svensson, L., A. Aszodi, et al. (1999). "Fibromodulin-null mice have abnormal collagen fibrils, tissue organization, and altered lumican deposition in tendon." *J Biol Chem* 274(14): 9636-47.

Takeji, M., T. Moriyama, et al. (2006). "Smooth muscle alpha-actin deficiency in myofibroblasts leads to enhanced renal tissue fibrosis." *J Biol Chem* 281(52): 40193-200.

Tomasek, J. J., J. McRae, et al. (2005). "Regulation of alpha-smooth muscle actin expression in granulation tissue myofibroblasts is dependent on the intronic CArG element and the transforming growth factor-beta1 control element." *Am J Pathol* 166(5): 1343-51.

Yamaguchi, Y., D. M. Mann, et al. (1990). "Negative regulation of transforming growth factor-beta by the proteoglycan decorin." *Nature* 346(6281): 281-4.

Yang, Y. A., O. Dukhanina, et al. (2002). "Lifetime exposure to a soluble TGF-beta antagonist protects mice against metastasis without adverse side effects." *J Clin Invest* 109 (12): 1607-15.

---

We claim:

1. An isolated fibromodulin (FMOD) peptide (FMOD-P), wherein FMOD-P is a chemically modified isoform of a full length FMOD, wherein the FMOD-P consists of an amino acid sequence selected from the group consisting of SEQ ID NO: 18, SEQ ID NO: 19, SEQ ID NO:24, SEQ ID NO: 26, SEQ ID NO: 28, and SEQ ID NO: 34, and wherein the chemically modified isoform is achieved by using an acid, a base, esterification, PEGylation, or alkylation with a short chain alkyl group.

2. The FMOD-P of claim 1, wherein the isolated FMOD-P binds one TGF-β selected from the group consisting of TGF-β1, TGF-β2, and TGF-β3.

3. A composition, comprising a pharmaceutically acceptable carrier and an effective amount of any of the following ingredients:
   a) an isolated FMOD-P;
   b) a combination of two or more isolated FMOD-P;
   c) an isolated FMOD-P or a combination of two or more isolated FMOD-P and at least one TGF-β isoform;
   d) isolated FMOD and isolated FMOD-P or a combination of two or more isolated FMOD-P; and
   e) any combination of (a)-(d), wherein FMOD-P is an isoform of a full length FMOD, wherein the at least one TGF-β isoform is selected from the group consisting of TGF-β1, TGF-β2, TGF-β3, and a combination thereof, wherein the isolated FMOD-P consists of an amino acid sequence selected from the group consisting of SEQ ID NO: 18, SEQ ID NO: 19, SEQ ID NO: 24, SEQ ID NO: 26, SEQ ID NO: 28, and SEQ ID NO: 34, and wherein FMOD consists of an amino acid sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, and SEQ ID NO. 12.

4. The composition of claim 3, wherein the isolated FMOD-P binds one TGF-β selected from the group consisting of TGF-β1, TGF-β2, and TGF-β3.

5. The composition of claim 3, further comprising an excipient.

6. The composition of claim 5, wherein the excipient is a pharmaceutically acceptable carrier or dermatologically acceptable carrier.

7. A formulation comprising the composition of claim 3 and an excipient, wherein the formulation is for systemic or local delivery.

8. The formulation of claim 7, wherein the local delivery is topical delivery, transdermal delivery, intradermal delivery, micro needle delivery, delivery as a coating on medical devices, or delivery by impregnating or coating on scaffold devices, and wherein the systemic delivery is injection, oral administration, nasal delivery, or inhalation.

* * * * *

SEQUENCE LISTING

<160> NUMBER OF SEQ ID NOS: 68

<210> SEQ ID NO 1
<211> LENGTH: 376
<212> TYPE: PRT
<213> ORGANISM: Homo sapiens

<400> SEQUENCE: 1

```
Met Gln Trp Thr Ser Leu Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95
```

```
Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
        130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
            340                 345                 350

Asn Glu Ile Lys Arg Ser Ala Met Pro Ala Asp Ala Pro Leu Cys Leu
        355                 360                 365

Arg Leu Ala Ser Leu Ile Glu Ile
    370                 375

<210> SEQ ID NO 2
<211> LENGTH: 376
<212> TYPE: PRT
<213> ORGANISM: Homo sapiens

<400> SEQUENCE: 2

Met Gln Trp Thr Ser Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95
```

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
        130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
            340                 345                 350

Asn Glu Ile Lys Arg Ser Ala Met Pro Ala Asp Ala Pro Leu Cys Leu
        355                 360                 365

Arg Leu Ala Ser Leu Ile Glu Ile
    370                 375

<210> SEQ ID NO 3
<211> LENGTH: 58
<212> TYPE: PRT
<213> ORGANISM: Homo sapiens

<400> SEQUENCE: 3

Tyr Leu Gln Gly Asn Arg Ile Asn Glu Phe Ser Ile Ser Ser Phe Cys
1               5                   10                  15

Thr Val Val Asp Val Val Asn Phe Ser Lys Leu Gln Val Leu Arg Leu
            20                  25                  30

Asp Gly Asn Glu Ile Lys Arg Ser Ala Met Pro Ala Asp Ala Pro Leu
        35                  40                  45

Cys Leu Arg Leu Ala Ser Leu Ile Glu Ile
    50                  55

<210> SEQ ID NO 4
<211> LENGTH: 362
<212> TYPE: PRT

<213> ORGANISM: Homo sapiens

<400> SEQUENCE: 4

Met Gln Trp Thr Ser Leu Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Pro Phe Val Pro Ser Arg Met Lys Tyr Val
                85                  90                  95

Tyr Phe Gln Asn Asn Gln Ile Thr Ser Ile Gln Glu Gly Val Phe Asp
            100                 105                 110

Asn Ala Thr Gly Leu Leu Trp Ile Ala Leu His Gly Asn Gln Ile Thr
        115                 120                 125

Ser Asp Lys Val Gly Arg Lys Val Phe Ser Lys Leu Arg His Leu Glu
    130                 135                 140

Arg Leu Tyr Leu Asp His Asn Asn Leu Thr Arg Met Pro Gly Pro Leu
145                 150                 155                 160

Pro Arg Ser Leu Arg Glu Leu His Leu Asp His Asn Gln Ile Ser Arg
                165                 170                 175

Val Pro Asn Asn Ala Leu Glu Gly Leu Glu Asn Leu Thr Ala Leu Tyr
            180                 185                 190

Leu Gln His Asn Glu Ile Gln Glu Val Gly Ser Ser Met Arg Gly Leu
        195                 200                 205

Arg Ser Leu Ile Leu Leu Asp Leu Ser Tyr Asn His Leu Arg Lys Val
    210                 215                 220

Pro Asp Gly Leu Pro Ser Ala Leu Glu Gln Leu Tyr Met Glu His Asn
225                 230                 235                 240

Asn Val Tyr Thr Val Pro Asp Ser Tyr Phe Arg Gly Ala Pro Lys Leu
                245                 250                 255

Leu Tyr Val Arg Leu Ser His Asn Ser Leu Thr Asn Asn Gly Leu Ala
            260                 265                 270

Ser Asn Thr Phe Asn Ser Ser Leu Leu Glu Leu Asp Leu Ser Tyr
        275                 280                 285

Asn Gln Leu Gln Lys Ile Pro Pro Val Asn Thr Asn Leu Glu Asn Leu
    290                 295                 300

Tyr Leu Gln Gly Asn Arg Ile Asn Glu Phe Ser Ile Ser Ser Phe Cys
305                 310                 315                 320

Thr Val Val Asp Val Val Asn Phe Ser Lys Leu Gln Val Leu Arg Leu
                325                 330                 335

Asp Gly Asn Glu Ile Lys Arg Ser Ala Met Pro Ala Asp Ala Pro Leu
            340                 345                 350

Cys Leu Arg Leu Ala Ser Leu Ile Glu Ile
        355                 360

<210> SEQ ID NO 5
<211> LENGTH: 201
<212> TYPE: PRT
<213> ORGANISM: Homo sapiens

<400> SEQUENCE: 5

Met Lys Met Thr Leu Ile Gly Gly Ser Thr Thr Ser Ala Ala Ser Ser
1               5                   10                  15

Pro Pro Thr Thr Ile Pro Met Thr Leu Thr Arg Met Arg Pro Thr Ser
            20                  25                  30

Leu Thr Pro Met Gly Trp Met Lys Gly Gln Pro Thr Pro Thr Ala Leu
        35                  40                  45

His Leu Asp His Asn Gln Ile Ser Arg Val Pro Asn Asn Ala Leu Glu
    50                  55                  60

Gly Leu Glu Asn Leu Thr Ala Met Tyr Cys Asp Asn Arg Asn Leu Lys
65                  70                  75                  80

Tyr Leu Pro Phe Val Pro Ser Arg Met Lys Tyr Val Tyr Phe Gln Asn
                85                  90                  95

Asn Gln Ile Thr Ser Ile Gln Glu Gly Val Phe Asp Asn Ala Thr Gly
            100                 105                 110

Leu Leu Trp Ile Ala Leu His Gly Asn Gln Ile Thr Ser Asp Lys Val
        115                 120                 125

Gly Arg Lys Val Phe Ser Lys Leu Arg His Leu Glu Arg Leu Tyr Leu
    130                 135                 140

Asp His Asn Asn Leu Thr Arg Met Pro Gly Pro Leu Pro Arg Ser Leu
145                 150                 155                 160

Arg Glu Leu His Leu Asp His Asn Gln Ile Pro Ala Thr Ala Pro Arg
                165                 170                 175

Asn Ala Thr Ala His Pro Thr Ser Pro Arg Pro Cys Thr Ser Asn Thr
            180                 185                 190

Met Arg Ser Arg Lys Trp Ala Val Pro
        195                 200

<210> SEQ ID NO 6
<211> LENGTH: 287
<212> TYPE: PRT
<213> ORGANISM: Homo sapiens

<400> SEQUENCE: 6

Met Lys Met Thr Leu Ile Gly Gly Ser Thr Thr Ser Ala Ala Ser Ser
1               5                   10                  15

Pro Pro Thr Thr Ile Pro Met Thr Leu Thr Arg Met Arg Pro Thr Ser
            20                  25                  30

Leu Thr Pro Met Gly Trp Met Lys Gly Gln Pro Thr Pro Thr Ala Leu
        35                  40                  45

His Pro Leu Gln Ile Pro Ala Thr Ala Pro Arg Lys Val Phe Ser Lys
    50                  55                  60

Leu Arg His Leu Glu Arg Leu Tyr Leu Asp His Asn Asn Leu Thr Arg
65                  70                  75                  80

Met Pro Gly Pro Leu Pro Arg Ser Leu Arg Glu Leu His Leu Asp His
                85                  90                  95

Asn Gln Ile Ser Arg Val Pro Asn Asn Ala Leu Glu Gly Leu Glu Asn
            100                 105                 110

Leu Thr Ala Leu Tyr Leu Gln His Asn Glu Ile Gln Glu Val Gly Ser
        115                 120                 125

Ser Met Arg Gly Leu Arg Ser Leu Ile Leu Leu Asp Leu Ser Tyr Asn
    130                 135                 140

His Leu Arg Lys Val Pro Asp Gly Leu Pro Ser Ala Leu Glu Gln Leu
145                 150                 155                 160

```
Tyr Met Glu His Asn Asn Val Tyr Thr Val Pro Asp Ser Tyr Phe Arg
            165                 170                 175

Gly Ala Pro Lys Leu Leu Tyr Val Arg Leu Ser His Asn Ser Leu Thr
        180                 185                 190

Asn Asn Gly Leu Ala Ser Asn Thr Phe Asn Ser Ser Leu Leu Glu
        195                 200                 205

Leu Asp Leu Ser Tyr Asn Gln Leu Gln Lys Ile Pro Pro Val Asn Thr
    210                 215                 220

Asn Leu Glu Asn Leu Tyr Leu Gln Gly Asn Arg Ile Asn Glu Phe Ser
225                 230                 235                 240

Ile Ser Ser Phe Cys Thr Val Val Asp Val Val Asn Phe Ser Lys Leu
                245                 250                 255

Gln Val Leu Arg Leu Asp Gly Asn Glu Ile Lys Arg Ser Ala Met Pro
            260                 265                 270

Ala Asp Ala Pro Leu Cys Leu Arg Leu Ala Ser Leu Ile Glu Ile
            275                 280                 285

<210> SEQ ID NO 7
<211> LENGTH: 623
<212> TYPE: PRT
<213> ORGANISM: Homo sapiens

<400> SEQUENCE: 7

Met Ala Lys Ser Cys Pro Ser Val Cys Arg Cys Asp Ala Gly Phe Ile
1               5                   10                  15

Tyr Cys Asn Asp Arg Phe Leu Thr Ser Ile Pro Thr Gly Ile Pro Glu
                20                  25                  30

Asp Ala Thr Thr Leu Tyr Leu Gln Asn Asn Gln Ile Asn Asn Ala Gly
            35                  40                  45

Ile Pro Ser Asp Leu Lys Asn Leu Leu Lys Val Glu Arg Ile Tyr Leu
        50                  55                  60

Tyr His Asn Ser Leu Asp Glu Phe Pro Thr Asn Leu Pro Lys Tyr Val
65                  70                  75                  80

Lys Glu Leu His Leu Gln Glu Asn Asn Ile Arg Thr Ile Thr Tyr Asp
                85                  90                  95

Ser Leu Ser Lys Ile Pro Tyr Leu Glu Glu Leu His Leu Asp Asp Asn
            100                 105                 110

Ser Val Ser Ala Val Ser Ile Glu Glu Gly Ala Phe Arg Asp Ser Asn
        115                 120                 125

Tyr Leu Arg Leu Leu Phe Leu Ser Arg Asn His Leu Ser Thr Ile Pro
    130                 135                 140

Trp Gly Leu Pro Arg Thr Ile Glu Glu Leu Arg Leu Asp Asp Asn Arg
145                 150                 155                 160

Ile Ser Thr Ile Ser Ser Pro Ser Leu Gln Gly Leu Thr Ser Leu Lys
                165                 170                 175

Arg Leu Val Leu Asp Gly Asn Leu Leu Asn Asn His Gly Leu Gly Asp
            180                 185                 190

Lys Val Phe Phe Asn Leu Val Asn Leu Thr Glu Leu Ser Leu Val Arg
        195                 200                 205

Asn Ser Leu Thr Ala Ala Pro Val Asn Leu Pro Gly Thr Asn Leu Arg
    210                 215                 220

Lys Leu Tyr Leu Gln Asp Asn His Ile Asn Arg Val Pro Pro Asn Ala
225                 230                 235                 240

Phe Ser Tyr Leu Arg Gln Leu Tyr Arg Leu Asp Met Ser Asn Asn Asn
                245                 250                 255
```

```
Leu Ser Asn Leu Pro Gln Gly Ile Phe Asp Leu Asp Asn Ile Thr
            260                 265                 270
Gln Leu Ile Leu Arg Asn Asn Pro Trp Tyr Cys Gly Cys Lys Met Lys
        275                 280                 285
Trp Val Arg Asp Trp Leu Gln Ser Leu Pro Val Lys Val Asn Val Arg
290                 295                 300
Gly Leu Met Cys Gln Ala Pro Glu Lys Val Arg Gly Met Ala Ile Lys
305                 310                 315                 320
Asp Leu Asn Ala Glu Leu Phe Asp Cys Lys Asp Ser Gly Ile Val Ser
                325                 330                 335
Thr Ile Gln Ile Thr Thr Ala Ile Pro Asn Thr Val Tyr Pro Ala Gln
            340                 345                 350
Gly Gln Trp Pro Ala Pro Val Thr Lys Gln Pro Asp Ile Lys Asn Pro
        355                 360                 365
Lys Leu Thr Lys Asp His Gln Thr Thr Gly Ser Pro Ser Arg Lys Thr
    370                 375                 380
Ile Thr Ile Thr Val Lys Ser Val Thr Ser Asp Thr Ile His Ile Ser
385                 390                 395                 400
Trp Lys Leu Ala Leu Pro Met Thr Ala Leu Arg Leu Ser Trp Leu Lys
                405                 410                 415
Leu Gly His Ser Pro Ala Phe Gly Ser Ile Thr Glu Thr Ile Val Thr
            420                 425                 430
Gly Glu Arg Ser Glu Tyr Leu Val Thr Ala Leu Glu Pro Asp Ser Pro
        435                 440                 445
Tyr Lys Val Cys Met Val Pro Met Glu Thr Ser Asn Leu Tyr Leu Phe
    450                 455                 460
Asp Glu Thr Pro Val Cys Ile Glu Thr Glu Thr Ala Pro Leu Arg Met
465                 470                 475                 480
Tyr Asn Pro Thr Thr Thr Leu Asn Arg Glu Gln Glu Lys Glu Pro Tyr
                485                 490                 495
Lys Asn Pro Asn Leu Pro Leu Ala Ala Ile Ile Gly Gly Ala Val Ala
            500                 505                 510
Leu Val Thr Ile Ala Leu Leu Ala Leu Val Cys Trp Tyr Val His Arg
        515                 520                 525
Asn Gly Ser Leu Phe Ser Arg Asn Cys Ala Tyr Ser Lys Gly Arg Arg
    530                 535                 540
Arg Lys Asp Asp Tyr Ala Glu Ala Gly Thr Lys Lys Asp Asn Ser Ile
545                 550                 555                 560
Leu Glu Ile Arg Glu Thr Ser Phe Gln Met Leu Pro Ile Ser Asn Glu
                565                 570                 575
Pro Ile Ser Lys Glu Glu Phe Val Ile His Thr Ile Phe Pro Pro Asn
            580                 585                 590
Gly Met Asn Leu Tyr Lys Asn Asn His Ser Glu Ser Ser Ser Asn Arg
        595                 600                 605
Ser Tyr Arg Asp Ser Gly Ile Pro Asp Ser Asp His Ser His Ser
    610                 615                 620

<210> SEQ ID NO 8
<211> LENGTH: 376
<212> TYPE: PRT
<213> ORGANISM: Artificial Sequence
<220> FEATURE:
<223> OTHER INFORMATION: Synthetic peptide

<400> SEQUENCE: 8
```

```
Met Gln Trp Thr Ser Leu Leu Leu Ala Gly Leu Phe Ser Leu Ser
1               5                   10                  15

Gln Ala Gln Tyr Glu Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                      60

Tyr Gly Ser Pro Ser Pro Pro Asp Pro Arg Asp Cys Pro Gln Glu Cys
65              70                  75                      80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
                100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
            340                 345                 350

Asn Glu Ile Lys Arg Ser Ala Met Pro Ala Asp Ala Pro Leu Cys Leu
        355                 360                 365

Arg Leu Ala Ser Leu Ile Glu Ile
    370                 375

<210> SEQ ID NO 9
<211> LENGTH: 376
<212> TYPE: PRT
<213> ORGANISM: Homo sapiens
```

<400> SEQUENCE: 9

```
Met Gln Trp Thr Ser Leu Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
        115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
    210                 215                 220

Leu Tyr Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Gln Leu Gln Val Val Arg Leu Asp Gly
            340                 345                 350

Asn Glu Met Lys Arg Ser Ala Met Pro Ala Glu Ala Pro Leu Cys Leu
        355                 360                 365

Arg Leu Ala Ser Leu Ile Glu Ile
    370                 375
```

<210> SEQ ID NO 10
<211> LENGTH: 375
<212> TYPE: PRT
<213> ORGANISM: Homo sapiens

<400> SEQUENCE: 10

```
Met Gln Trp Ala Ser Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Leu Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
        115                 120                 125

Thr Gly Leu Leu Trp Ile Ala Leu His Gly Asn Gln Ile Thr Ser Asp
130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asp Glu Ile Gln Glu Val Gly Ser Ser Met Arg Gly Leu Arg Ser
210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Leu Glu Leu Asp Leu Ser Tyr Asn Gln Leu
290                 295                 300

Gln Lys Ile Pro Pro Val Asn Thr Asn Leu Glu Asn Leu Tyr Leu Gln
305                 310                 315                 320

Gly Asn Arg Ile Asn Glu Phe Ser Ile Ser Ser Phe Cys Thr Val Val
                325                 330                 335

Asp Val Val Asn Phe Ser Lys Leu Gln Val Val Arg Leu Asp Gly Asn
            340                 345                 350

Glu Ile Lys Arg Ser Ala Met Pro Ala Asp Ala Pro Leu Cys Leu Arg
        355                 360                 365

Leu Ala Ser Leu Ile Glu Ile
370                 375
```

<210> SEQ ID NO 11
<211> LENGTH: 376
<212> TYPE: PRT

<213> ORGANISM: Artificial Sequence
<220> FEATURE:
<223> OTHER INFORMATION: Synthetic peptide

<400> SEQUENCE: 11

Met Gln Trp Thr Ser Leu Leu Leu Ala Gly Leu Phe Ser Leu Ser
1               5                   10                  15

Gln Ala Gln Tyr Glu Asp Pro His Trp Trp Phe His Tyr Leu Arg
                20                  25                  30

Ser Gln Ser Thr Tyr Tyr Asp Pro Tyr Asp Pro Tyr Pro Tyr Glu
            35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
                100                 105                 110

Gln Asn Asn Gln Ile Thr Ser Ile Gln Glu Gly Val Phe Asp Asn Ala
                115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
                180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
                260                 265                 270

Val Arg Leu Ser His Asn Ser Leu Thr Asn Asn Gly Leu Ala Ser Asn
    275                 280                 285

Thr Phe Asn Ser Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
                340                 345                 350

Asn Glu Ile Lys Arg Ser Ala Met Pro Ala Asp Ala Pro Leu Cys Leu
                355                 360                 365

Arg Leu Ala Ser Leu Ile Gly Ile
    370                 375

```
<210> SEQ ID NO 12
<211> LENGTH: 377
<212> TYPE: PRT
<213> ORGANISM: Artificial Sequence
<220> FEATURE:
<223> OTHER INFORMATION: Synthetic peptide

<400> SEQUENCE: 12

Met Gln Trp Thr Ser Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
        35                  40                  45

Thr Tyr Glu Pro Tyr Pro Tyr Gly Val Asp Glu Gly Pro Ala Tyr Thr
    50                  55                  60

Tyr Gly Ser Pro Ser Pro Asp Pro Arg Asp Cys Pro Gln Glu Cys
65                  70              75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
        115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
            340                 345                 350

Asn Glu Ile Lys Arg Ser Ala Met Pro Ala Asp Ala Pro Leu Cys Leu
        355                 360                 365

Arg Leu Ala Ser Leu Ile Glu Ile Leu
```

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

```
Asn Arg Asn Leu Lys Tyr Leu Lys Pro Phe Val Pro Ser Arg Met Lys
1               5                   10                  15
```

<210> SEQ ID NO 14
<211> LENGTH: 21
<212> TYPE: PRT
<213> ORGANISM: Artificial Sequence
<220> FEATURE:
<223> OTHER INFORMATION: Synthetic peptide

<400> SEQUENCE: 14

```
Phe Gln Asn Asn Gln Ile Thr Ser Ile Gln Glu Gly Val Phe Asp Asn
1               5                   10                  15

Ala Thr Gly Leu Leu
            20
```

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

```
Asn Arg Asn Leu Lys Tyr Lys Pro Phe Val Pro Ser Arg Met Lys
1               5                   10                  15
```

<210> SEQ ID NO 16
<211> LENGTH: 64
<212> TYPE: PRT
<213> ORGANISM: Artificial Sequence
<220> FEATURE:
<223> OTHER INFORMATION: Synthetic peptide

<400> SEQUENCE: 16

```
Tyr Leu Arg Ser Gln Gln Ser Thr Tyr Tyr Asp Pro Tyr Asp Pro Tyr
1               5                   10                  15

Pro Tyr Glu Thr Tyr Glu Pro Tyr Pro Tyr Gly Val Asp Glu Gly Pro
            20                  25                  30

Ala Tyr Thr Tyr Gly Ser Pro Ser Pro Pro Asp Pro Arg Asp Cys Pro
        35                  40                  45

Gln Glu Cys Asp Cys Pro Pro Asn Phe Pro Thr Ala Met Tyr Cys Asp
    50                  55                  60
```

<210> SEQ ID NO 17
<211> LENGTH: 40
<212> TYPE: PRT
<213> ORGANISM: Artificial Sequence
<220> FEATURE:
<223> OTHER INFORMATION: Synthetic peptide

<400> SEQUENCE: 17

```
Pro Tyr Gly Val Asp Glu Gly Pro Ala Tyr Thr Tyr Gly Ser Pro Ser
1               5                   10                  15
```

```
Pro Pro Asp Pro Arg Asp Cys Pro Gln Glu Cys Asp Cys Pro Pro Asn
            20                  25                  30

Phe Pro Thr Ala Met Tyr Cys Asp
            35                  40
```

<210> SEQ ID NO 18
<211> LENGTH: 39
<212> TYPE: PRT
<213> ORGANISM: Artificial Sequence
<220> FEATURE:
<223> OTHER INFORMATION: Synthetic peptide

<400> SEQUENCE: 18

```
Ser Arg Met Lys Tyr Val Tyr Phe Gln Asn Asn Gln Ile Thr Ser Ile
1               5                   10                  15

Gln Glu Gly Val Phe Asp Asn Ala Thr Gly Leu Leu Trp Ile Ala Leu
            20                  25                  30

His Gly Asn Gln Ile Thr Ser
            35
```

<210> SEQ ID NO 19
<211> LENGTH: 50
<212> TYPE: PRT
<213> ORGANISM: Artificial Sequence
<220> FEATURE:
<223> OTHER INFORMATION: Synthetic peptide

<400> SEQUENCE: 19

```
Asn Arg Asn Leu Lys Tyr Leu Pro Phe Val Pro Ser Arg Met Lys Tyr
1               5                   10                  15

Val Tyr Phe Gln Asn Asn Gln Ile Thr Ser Ile Gln Glu Gly Val Phe
            20                  25                  30

Asp Asn Ala Thr Gly Leu Leu Trp Ile Ala Leu His Gly Asn Gln Ile
            35                  40                  45

Thr Ser
    50
```

<210> SEQ ID NO 20
<211> LENGTH: 45
<212> TYPE: PRT
<213> ORGANISM: Artificial Sequence
<220> FEATURE:
<223> OTHER INFORMATION: Synthetic peptide

<400> SEQUENCE: 20

```
Asp Lys Val Gly Arg Lys Val Phe Ser Lys Leu Arg His Leu Glu Arg
1               5                   10                  15

Leu Tyr Leu Asp His Asn Asn Leu Thr Arg Met Pro Gly Pro Leu Pro
            20                  25                  30

Arg Ser Leu Arg Glu Leu His Leu Asp His Asn Gln Ile
            35                  40                  45
```

<210> SEQ ID NO 21
<211> LENGTH: 68
<212> TYPE: PRT
<213> ORGANISM: Artificial Sequence
<220> FEATURE:
<223> OTHER INFORMATION: Synthetic peptide

<400> SEQUENCE: 21

```
Ser Arg Val Pro Asn Asn Ala Leu Glu Gly Leu Glu Asn Leu Thr Ala
1               5                   10                  15
```

```
Leu Tyr Leu Gln His Asn Glu Ile Gln Val Gly Ser Ser Met Arg
                20                  25                  30

Gly Leu Arg Ser Leu Ile Leu Leu Asp Leu Ser Tyr Asn His Leu Arg
            35                  40                  45

Lys Val Pro Asp Gly Leu Pro Ser Ala Leu Gln Leu Tyr Met Glu
    50                  55                  60

His Asn Asn Val
65

<210> SEQ ID NO 22
<211> LENGTH: 69
<212> TYPE: PRT
<213> ORGANISM: Artificial Sequence
<220> FEATURE:
<223> OTHER INFORMATION: Synthetic peptide

<400> SEQUENCE: 22

Tyr Thr Val Pro Asp Ser Tyr Phe Arg Gly Ala Pro Lys Leu Leu Tyr
1               5                   10                  15

Val Arg Leu Ser His Asn Ser Leu Thr Asn Asn Gly Leu Ala Ser Asn
                20                  25                  30

Thr Phe Asn Ser Ser Leu Leu Glu Leu Asp Leu Ser Tyr Asn Gln
            35                  40                  45

Leu Gln Lys Ile Pro Pro Val Asn Thr Asn Leu Glu Asn Leu Tyr Leu
    50                  55                  60

Gln Gly Asn Arg Ile
65

<210> SEQ ID NO 23
<211> LENGTH: 51
<212> TYPE: PRT
<213> ORGANISM: Artificial Sequence
<220> FEATURE:
<223> OTHER INFORMATION: Synthetic peptide

<400> SEQUENCE: 23

Asn Glu Phe Ser Ile Ser Ser Phe Cys Thr Val Val Asp Val Val Asn
1               5                   10                  15

Phe Ser Lys Leu Gln Val Leu Arg Leu Asp Gly Asn Glu Ile Lys Arg
                20                  25                  30

Ser Ala Met Pro Ala Asp Ala Pro Leu Cys Leu Arg Leu Ala Ser Leu
            35                  40                  45

Ile Glu Ile
    50

<210> SEQ ID NO 24
<211> LENGTH: 40
<212> TYPE: PRT
<213> ORGANISM: Artificial Sequence
<220> FEATURE:
<223> OTHER INFORMATION: Synthetic peptide

<400> SEQUENCE: 24

Gln Trp Thr Ser Leu Leu Leu Ala Gly Leu Phe Ser Leu Ser Gln
1               5                   10                  15

Ala Gln Tyr Glu Asp Asp Pro His Trp Trp Phe His Tyr Leu Arg Ser
                20                  25                  30

Gln Gln Ser Thr Tyr Tyr Asp Pro
            35                  40
```

```
<210> SEQ ID NO 25
<211> LENGTH: 40
<212> TYPE: PRT
<213> ORGANISM: Artificial Sequence
<220> FEATURE:
<223> OTHER INFORMATION: Synthetic peptide

<400> SEQUENCE: 25

Asp Asp Pro His Trp Trp Phe His Tyr Leu Arg Ser Gln Gln Ser Thr
1               5                   10                  15

Tyr Tyr Asp Pro Tyr Asp Pro Tyr Pro Tyr Glu Thr Tyr Glu Pro Tyr
            20                  25                  30

Pro Tyr Gly Val Asp Glu Gly Pro
        35                  40

<210> SEQ ID NO 26
<211> LENGTH: 50
<212> TYPE: PRT
<213> ORGANISM: Artificial Sequence
<220> FEATURE:
<223> OTHER INFORMATION: Synthetic peptide

<400> SEQUENCE: 26

Asp Pro Arg Asp Cys Pro Gln Glu Cys Asp Cys Pro Pro Asn Phe Pro
1               5                   10                  15

Thr Ala Met Tyr Cys Asp Asn Arg Asn Leu Lys Tyr Leu Pro Phe Val
            20                  25                  30

Pro Ser Arg Met Lys Tyr Val Tyr Phe Gln Asn Asn Gln Ile Thr Ser
        35                  40                  45

Ile Gln
    50

<210> SEQ ID NO 27
<211> LENGTH: 51
<212> TYPE: PRT
<213> ORGANISM: Artificial Sequence
<220> FEATURE:
<223> OTHER INFORMATION: Synthetic peptide

<400> SEQUENCE: 27

Tyr Gly Ser Pro Ser Pro Pro Asp Pro Arg Asp Cys Pro Gln Glu Cys
1               5                   10                  15

Asp Cys Pro Pro Asn Phe Pro Thr Ala Met Tyr Cys Asp Asn Arg Asn
            20                  25                  30

Leu Lys Tyr Leu Pro Phe Val Pro Ser Arg Met Lys Tyr Val Tyr Phe
        35                  40                  45

Gln Asn Asn
    50

<210> SEQ ID NO 28
<211> LENGTH: 50
<212> TYPE: PRT
<213> ORGANISM: Artificial Sequence
<220> FEATURE:
<223> OTHER INFORMATION: Synthetic peptide

<400> SEQUENCE: 28

Phe Pro Thr Ala Met Tyr Cys Asp Asn Arg Asn Leu Lys Tyr Leu Pro
1               5                   10                  15

Phe Val Pro Ser Arg Met Lys Tyr Val Tyr Phe Gln Asn Asn Gln Ile
            20                  25                  30

Thr Ser Ile Gln Glu Gly Val Phe Asp Asn Ala Thr Gly Leu Leu Trp
```

```
                     35                  40                  45

Ile Ala
    50

<210> SEQ ID NO 29
<211> LENGTH: 58
<212> TYPE: PRT
<213> ORGANISM: Artificial Sequence
<220> FEATURE:
<223> OTHER INFORMATION: Synthetic peptide

<400> SEQUENCE: 29

Leu Leu Trp Ile Ala Leu His Gly Asn Gln Ile Thr Ser Asp Lys Val
1               5                   10                  15

Gly Arg Lys Val Phe Ser Lys Leu Arg His Leu Glu Arg Leu Tyr Leu
            20                  25                  30

Asp His Asn Asn Leu Thr Arg Met Pro Gly Pro Leu Pro Arg Ser Leu
        35                  40                  45

Arg Glu Leu His Leu Asp His Asn Gln Ile
    50                  55

<210> SEQ ID NO 30
<211> LENGTH: 50
<212> TYPE: PRT
<213> ORGANISM: Artificial Sequence
<220> FEATURE:
<223> OTHER INFORMATION: Synthetic peptide

<400> SEQUENCE: 30

Ala Tyr Thr Tyr Gly Ser Pro Ser Pro Pro Asp Pro Arg Asp Cys Pro
1               5                   10                  15

Gln Glu Cys Asp Cys Pro Pro Asn Phe Pro Thr Ala Met Tyr Cys Asp
            20                  25                  30

Asn Arg Asn Leu Lys Tyr Leu Pro Phe Val Pro Ser Arg Met Lys Tyr
        35                  40                  45

Val Tyr
    50

<210> SEQ ID NO 31
<211> LENGTH: 47
<212> TYPE: PRT
<213> ORGANISM: Artificial Sequence
<220> FEATURE:
<223> OTHER INFORMATION: Synthetic peptide

<400> SEQUENCE: 31

Ser Arg Val Pro Asn Asn Ala Leu Glu Gly Leu Glu Asn Leu Thr Ala
1               5                   10                  15

Leu Tyr Leu Gln His Asn Glu Ile Gln Glu Val Gly Ser Ser Met Arg
            20                  25                  30

Gly Leu Arg Ser Leu Ile Leu Leu Asp Leu Ser Tyr Asn His Leu
        35                  40                  45

<210> SEQ ID NO 32
<211> LENGTH: 46
<212> TYPE: PRT
<213> ORGANISM: Artificial Sequence
<220> FEATURE:
<223> OTHER INFORMATION: Synthetic peptide

<400> SEQUENCE: 32

Arg Lys Val Pro Asp Gly Leu Pro Ser Ala Leu Glu Gln Leu Tyr Met
```

```
                1               5                  10                  15
Glu His Asn Asn Val Tyr Thr Val Pro Asp Ser Tyr Phe Arg Gly Ala
                        20                  25                  30

Pro Lys Leu Leu Tyr Val Arg Leu Ser His Asn Ser Leu Thr
            35                  40                  45
```

<210> SEQ ID NO 33
<211> LENGTH: 44
<212> TYPE: PRT
<213> ORGANISM: Artificial Sequence
<220> FEATURE:
<223> OTHER INFORMATION: Synthetic peptide

<400> SEQUENCE: 33

```
Asn Asn Gly Leu Ala Ser Asn Thr Phe Asn Ser Ser Leu Leu Glu
1               5                  10                  15

Leu Asp Leu Ser Tyr Asn Gln Leu Gln Lys Ile Pro Pro Val Asn Thr
                20                  25                  30

Asn Leu Glu Asn Leu Tyr Leu Gln Gly Asn Arg Ile
            35                  40
```

<210> SEQ ID NO 34
<211> LENGTH: 50
<212> TYPE: PRT
<213> ORGANISM: Artificial Sequence
<220> FEATURE:
<223> OTHER INFORMATION: Synthetic peptide

<400> SEQUENCE: 34

```
Thr Ser Ile Gln Glu Gly Val Phe Asp Asn Ala Thr Gly Leu Leu Trp
1               5                  10                  15

Ile Ala Leu His Gly Asn Gln Ile Thr Ser Asp Lys Val Gly Arg Lys
                20                  25                  30

Val Phe Ser Lys Leu Arg His Leu Glu Arg Leu Tyr Leu Asp His Asn
            35                  40                  45

Asn Leu
    50
```

<210> SEQ ID NO 35
<211> LENGTH: 47
<212> TYPE: PRT
<213> ORGANISM: Artificial Sequence
<220> FEATURE:
<223> OTHER INFORMATION: Synthetic peptide

<400> SEQUENCE: 35

```
Thr Arg Met Pro Gly Pro Leu Pro Arg Ser Leu Arg Glu Leu His Leu
1               5                  10                  15

Asp His Asn Gln Ile Ser Arg Val Pro Asn Asn Ala Leu Glu Gly Leu
                20                  25                  30

Glu Asn Leu Thr Ala Leu Tyr Leu Gln His Asn Glu Ile Gln Glu
            35                  40                  45
```

<210> SEQ ID NO 36
<211> LENGTH: 42
<212> TYPE: PRT
<213> ORGANISM: Artificial Sequence
<220> FEATURE:
<223> OTHER INFORMATION: Synthetic peptide

<400> SEQUENCE: 36

```
Val Gly Ser Ser Met Arg Gly Leu Arg Ser Leu Ile Leu Leu Asp Leu
```

```
            1               5                  10                 15
Ser Tyr Asn His Leu Arg Lys Val Pro Asp Gly Leu Pro Ser Ala Leu
                    20                  25                 30

Glu Gln Leu Tyr Met Glu His Asn Asn Val
            35                  40
```

<210> SEQ ID NO 37
<211> LENGTH: 49
<212> TYPE: PRT
<213> ORGANISM: Artificial Sequence
<220> FEATURE:
<223> OTHER INFORMATION: Synthetic peptide

<400> SEQUENCE: 37

```
Tyr Thr Val Pro Asp Ser Tyr Phe Arg Gly Ala Pro Lys Leu Leu Tyr
1               5                  10                 15

Val Arg Leu Ser His Asn Ser Leu Thr Asn Asn Gly Leu Ala Ser Asn
                    20                  25                 30

Thr Phe Asn Ser Ser Ser Leu Leu Glu Leu Asp Leu Ser Tyr Asn Gln
                    35                  40                  45

Leu
```

<210> SEQ ID NO 38
<211> LENGTH: 50
<212> TYPE: PRT
<213> ORGANISM: Artificial Sequence
<220> FEATURE:
<223> OTHER INFORMATION: Synthetic peptide

<400> SEQUENCE: 38

```
Gln Lys Ile Pro Pro Val Asn Thr Asn Leu Glu Asn Leu Tyr Leu Gln
1               5                  10                 15

Gly Asn Arg Ile Asn Glu Phe Ser Ile Ser Ser Phe Cys Thr Val Val
                    20                  25                 30

Asp Val Val Asn Phe Ser Lys Leu Gln Val Leu Arg Leu Asp Gly Asn
                    35                  40                  45

Glu Ile
    50
```

<210> SEQ ID NO 39
<211> LENGTH: 58
<212> TYPE: PRT
<213> ORGANISM: Artificial Sequence
<220> FEATURE:
<223> OTHER INFORMATION: Synthetic peptide

<400> SEQUENCE: 39

```
Asp Lys Val Gly Arg Lys Val Phe Ser Lys Leu Arg His Leu Glu Arg
1               5                  10                 15

Leu Tyr Leu Asp His Asn Asn Leu Thr Arg Met Pro Gly Pro Leu Pro
                    20                  25                 30

Arg Ser Leu Arg Glu Leu His Leu Asp His Asn Gln Ile Ser Arg Val
                    35                  40                  45

Pro Asn Asn Ala Leu Glu Gly Leu Glu Asn
    50                  55
```

<210> SEQ ID NO 40
<211> LENGTH: 40
<212> TYPE: PRT
<213> ORGANISM: Artificial Sequence
<220> FEATURE:

<223> OTHER INFORMATION: Synthetic peptide

<400> SEQUENCE: 40

Asn Ala Thr Gly Leu Leu Trp Ile Ala Leu His Gly Asn Gln Ile Thr
1               5                   10                  15

Ser Asp Lys Val Gly Arg Lys Val Phe Ser Lys Leu Arg His Leu Glu
            20                  25                  30

Arg Leu Tyr Leu Asp His Asn Asn
        35                  40

<210> SEQ ID NO 41
<211> LENGTH: 75
<212> TYPE: PRT
<213> ORGANISM: Artificial Sequence
<220> FEATURE:
<223> OTHER INFORMATION: Synthetic peptide

<400> SEQUENCE: 41

Asn Ala Thr Gly Leu Leu Trp Ile Ala Leu His Gly Asn Gln Ile Thr
1               5                   10                  15

Ser Asp Lys Val Gly Arg Lys Val Phe Ser Lys Leu Arg His Leu Glu
            20                  25                  30

Arg Leu Tyr Leu Asp His Asn Asn Leu Thr Arg Met Pro Gly Pro Leu
        35                  40                  45

Pro Arg Ser Leu Arg Glu Leu His Leu Asp His Asn Gln Ile Ser Arg
    50                  55                  60

Val Pro Asn Asn Ala Leu Glu Gly Leu Glu Asn
65                  70                  75

<210> SEQ ID NO 42
<211> LENGTH: 91
<212> TYPE: PRT
<213> ORGANISM: Artificial Sequence
<220> FEATURE:
<223> OTHER INFORMATION: Synthetic peptide

<400> SEQUENCE: 42

Asn Leu Thr Ala Leu Tyr Leu Gln His Asn Glu Ile Gln Glu Val Gly
1               5                   10                  15

Ser Ser Met Arg Gly Leu Arg Ser Leu Ile Leu Leu Asp Leu Ser Tyr
            20                  25                  30

Asn His Leu Arg Lys Val Pro Asp Gly Leu Pro Ser Ala Leu Glu Gln
        35                  40                  45

Leu Tyr Met Glu His Asn Asn Val Tyr Thr Val Pro Asp Ser Tyr Phe
    50                  55                  60

Arg Gly Ala Pro Lys Leu Leu Tyr Val Arg Leu Ser His Asn Ser Leu
65                  70                  75                  80

Thr Asn Asn Gly Leu Ala Ser Asn Thr Phe Asn
                85                  90

<210> SEQ ID NO 43
<211> LENGTH: 68
<212> TYPE: PRT
<213> ORGANISM: Artificial Sequence
<220> FEATURE:
<223> OTHER INFORMATION: Synthetic peptide

<400> SEQUENCE: 43

Thr Arg Met Pro Gly Pro Leu Pro Arg Ser Leu Arg Glu Leu His Leu
1               5                   10                  15

```
Asp His Asn Gln Ile Ser Arg Val Pro Asn Asn Ala Leu Glu Gly Leu
                20                  25                  30

Glu Asn Leu Thr Ala Leu Tyr Leu Gln His Asn Glu Ile Gln Glu Val
            35                  40                  45

Gly Ser Ser Met Arg Gly Leu Arg Ser Leu Ile Leu Leu Asp Leu Ser
    50                  55                  60

Tyr Asn His Leu
65

<210> SEQ ID NO 44
<211> LENGTH: 56
<212> TYPE: PRT
<213> ORGANISM: Artificial Sequence
<220> FEATURE:
<223> OTHER INFORMATION: Synthetic peptide

<400> SEQUENCE: 44

Arg Lys Val Pro Asp Gly Leu Pro Ser Ala Leu Glu Gln Leu Tyr Met
1               5                   10                  15

Glu His Asn Asn Val Tyr Thr Val Pro Asp Ser Tyr Phe Arg Gly Ala
                20                  25                  30

Pro Lys Leu Leu Tyr Val Arg Leu Ser His Asn Ser Leu Thr Asn Asn
            35                  40                  45

Gly Leu Ala Ser Asn Thr Phe Asn
        50                  55

<210> SEQ ID NO 45
<211> LENGTH: 44
<212> TYPE: PRT
<213> ORGANISM: Artificial Sequence
<220> FEATURE:
<223> OTHER INFORMATION: Synthetic peptide

<400> SEQUENCE: 45

Asn Ser Ser Ser Leu Leu Glu Leu Asp Leu Ser Tyr Asn Gln Leu Gln
1               5                   10                  15

Lys Ile Pro Pro Val Asn Thr Asn Leu Glu Asn Leu Tyr Leu Gln Gly
                20                  25                  30

Asn Arg Ile Asn Glu Phe Ser Ile Ser Ser Phe Cys
            35                  40

<210> SEQ ID NO 46
<211> LENGTH: 34
<212> TYPE: PRT
<213> ORGANISM: Artificial Sequence
<220> FEATURE:
<223> OTHER INFORMATION: Synthetic peptide

<400> SEQUENCE: 46

Cys Thr Val Val Asp Val Val Asn Phe Ser Lys Leu Gln Val Leu Arg
1               5                   10                  15

Leu Asp Gly Asn Glu Ile Lys Arg Ser Ala Met Pro Ala Asp Ala Pro
                20                  25                  30

Leu Cys

<210> SEQ ID NO 47
<211> LENGTH: 62
<212> TYPE: PRT
<213> ORGANISM: Artificial Sequence
<220> FEATURE:
<223> OTHER INFORMATION: Synthetic peptide
```

-continued

<400> SEQUENCE: 47

Gln Lys Ile Pro Pro Val Asn Thr Asn Leu Glu Asn Leu Tyr Leu Gln
1               5                   10                  15

Gly Asn Arg Ile Asn Glu Phe Ser Ile Ser Ser Phe Cys Thr Val Val
            20                  25                  30

Asp Val Val Asn Phe Ser Lys Leu Gln Val Leu Arg Leu Asp Gly Asn
        35                  40                  45

Glu Ile Lys Arg Ser Ala Met Pro Ala Asp Pro Leu Cys
    50                  55                  60

<210> SEQ ID NO 48
<211> LENGTH: 42
<212> TYPE: PRT
<213> ORGANISM: Artificial Sequence
<220> FEATURE:
<223> OTHER INFORMATION: Synthetic peptide

<400> SEQUENCE: 48

Cys Pro Gln Glu Cys Asp Cys Pro Pro Asn Phe Pro Thr Ala Met Tyr
1               5                   10                  15

Cys Asp Asn Arg Asn Leu Lys Tyr Leu Pro Phe Val Pro Ser Arg Met
            20                  25                  30

Lys Tyr Val Tyr Phe Gln Asn Asn Gln Ile
        35                  40

<210> SEQ ID NO 49
<211> LENGTH: 62
<212> TYPE: PRT
<213> ORGANISM: Artificial Sequence
<220> FEATURE:
<223> OTHER INFORMATION: Synthetic peptide

<400> SEQUENCE: 49

Ala Thr Gly Leu Leu Trp Ile Ala Leu His Gly Asn Gln Ile Thr Ser
1               5                   10                  15

Asp Lys Val Gly Arg Lys Val Phe Ser Lys Leu Arg His Leu Glu Arg
            20                  25                  30

Leu Tyr Leu Asp His Asn Asn Leu Thr Arg Met Pro Gly Pro Leu Pro
        35                  40                  45

Arg Ser Leu Arg Glu Leu His Leu Asp His Asn Gln Ile Ser
    50                  55                  60

<210> SEQ ID NO 50
<211> LENGTH: 49
<212> TYPE: PRT
<213> ORGANISM: Artificial Sequence
<220> FEATURE:
<223> OTHER INFORMATION: Synthetic peptide

<400> SEQUENCE: 50

Asn Leu Thr Arg Met Pro Gly Pro Leu Pro Arg Ser Leu Arg Glu Leu
1               5                   10                  15

His Leu Asp His Asn Gln Ile Ser Arg Val Pro Asn Asn Ala Leu Glu
            20                  25                  30

Gly Leu Glu Asn Leu Thr Ala Leu Tyr Leu Gln His Asn Glu Ile Gln
        35                  40                  45

Glu

<210> SEQ ID NO 51
<211> LENGTH: 36

```
<212> TYPE: PRT
<213> ORGANISM: Artificial Sequence
<220> FEATURE:
<223> OTHER INFORMATION: Synthetic peptide

<400> SEQUENCE: 51

Asn Leu Thr Arg Met Pro Gly Pro Leu Pro Arg Ser Leu Arg Glu Leu
1               5                   10                  15

His Leu Asp His Asn Gln Ile Ser Arg Val Pro Asn Asn Ala Leu Glu
            20                  25                  30

Gly Leu Glu Asn
        35

<210> SEQ ID NO 52
<211> LENGTH: 47
<212> TYPE: PRT
<213> ORGANISM: Artificial Sequence
<220> FEATURE:
<223> OTHER INFORMATION: Synthetic peptide

<400> SEQUENCE: 52

Gly Leu Pro Ser Ala Leu Glu Gln Leu Tyr Met Glu His Asn Asn Val
1               5                   10                  15

Tyr Thr Val Pro Asp Ser Tyr Phe Arg Gly Ala Pro Lys Leu Leu Tyr
            20                  25                  30

Val Arg Leu Ser His Asn Ser Leu Thr Asn Asn Gly Leu Ala Ser
        35                  40                  45

<210> SEQ ID NO 53
<211> LENGTH: 40
<212> TYPE: PRT
<213> ORGANISM: Artificial Sequence
<220> FEATURE:
<223> OTHER INFORMATION: Synthetic peptide

<400> SEQUENCE: 53

His Leu Asp His Asn Gln Ile Ser Arg Val Pro Asn Asn Ala Leu Glu
1               5                   10                  15

Gly Leu Glu Asn Leu Thr Ala Leu Tyr Leu Gln His Asn Glu Ile Gln
            20                  25                  30

Glu Val Gly Ser Ser Met Arg Gly
        35                  40

<210> SEQ ID NO 54
<211> LENGTH: 34
<212> TYPE: PRT
<213> ORGANISM: Artificial Sequence
<220> FEATURE:
<223> OTHER INFORMATION: Synthetic peptide

<400> SEQUENCE: 54

Phe Ser Lys Leu Gln Val Leu Arg Leu Asp Gly Asn Glu Ile Lys Arg
1               5                   10                  15

Ser Ala Met Pro Ala Asp Ala Pro Leu Cys Leu Arg Leu Ala Ser Leu
            20                  25                  30

Ile Glu

<210> SEQ ID NO 55
<211> LENGTH: 39
<212> TYPE: PRT
<213> ORGANISM: Artificial Sequence
<220> FEATURE:
<223> OTHER INFORMATION: Synthetic peptide
```

```
<400> SEQUENCE: 55

Pro Asn Asn Ala Leu Glu Gly Leu Glu Asn Leu Thr Ala Leu Tyr Leu
1               5                   10                  15

Gln His Asn Glu Ile Gln Glu Val Gly Ser Ser Met Arg Gly Leu Arg
            20                  25                  30

Ser Leu Ile Leu Leu Asp Leu
        35

<210> SEQ ID NO 56
<211> LENGTH: 49
<212> TYPE: PRT
<213> ORGANISM: Artificial Sequence
<220> FEATURE:
<223> OTHER INFORMATION: Synthetic peptide

<400> SEQUENCE: 56

Pro Asp Gly Leu Pro Ser Ala Leu Glu Gln Leu Tyr Met Glu His Asn
1               5                   10                  15

Asn Val Tyr Thr Val Pro Asp Ser Tyr Phe Arg Gly Ala Pro Lys Leu
            20                  25                  30

Leu Tyr Val Arg Leu Ser His Asn Ser Leu Thr Asn Asn Gly Leu Ala
        35                  40                  45

Ser

<210> SEQ ID NO 57
<211> LENGTH: 40
<212> TYPE: PRT
<213> ORGANISM: Artificial Sequence
<220> FEATURE:
<223> OTHER INFORMATION: Synthetic peptide

<400> SEQUENCE: 57

Leu Leu Asp Leu Ser Tyr Asn His Leu Arg Lys Val Pro Asp Gly Leu
1               5                   10                  15

Pro Ser Ala Leu Glu Gln Leu Tyr Met Glu His Asn Asn Val Tyr Thr
            20                  25                  30

Val Pro Asp Ser Tyr Phe Arg Gly
        35                  40

<210> SEQ ID NO 58
<211> LENGTH: 50
<212> TYPE: PRT
<213> ORGANISM: Artificial Sequence
<220> FEATURE:
<223> OTHER INFORMATION: Synthetic peptide

<400> SEQUENCE: 58

Ser Lys Leu Arg His Leu Glu Arg Leu Tyr Leu Asp His Asn Asn Leu
1               5                   10                  15

Thr Arg Met Pro Gly Pro Leu Pro Arg Ser Leu Arg Glu Leu His Leu
            20                  25                  30

Asp His Asn Gln Ile Ser Arg Val Pro Asn Asn Ala Leu Glu Gly Leu
        35                  40                  45

Glu Asn
    50

<210> SEQ ID NO 59
<211> LENGTH: 40
<212> TYPE: PRT
<213> ORGANISM: Artificial Sequence
```

```
<220> FEATURE:
<223> OTHER INFORMATION: Synthetic peptide

<400> SEQUENCE: 59

Leu Arg Ser Leu Ile Leu Leu Asp Leu Ser Tyr Asn His Leu Arg Lys
1               5                   10                  15

Val Pro Asp Gly Leu Pro Ser Ala Leu Glu Gln Leu Tyr Met Glu His
            20                  25                  30

Asn Asn Val Tyr Thr Val Pro Asp
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic peptide

<400> SEQUENCE: 60

Tyr Val Arg Leu Ser His Asn Ser Leu Thr Asn Asn Gly Leu Ala Ser
1               5                   10                  15

Asn Thr Phe Asn Ser Ser Ser Leu Leu Glu Leu Asp Leu Ser Tyr Asn
            20                  25                  30

Gln Leu Gln Lys Ile Pro Pro Val
        35                  40

<210> SEQ ID NO 61
<211> LENGTH: 40
<212> TYPE: PRT
<213> ORGANISM: Artificial Sequence
<220> FEATURE:
<223> OTHER INFORMATION: Synthetic peptide

<400> SEQUENCE: 61

Asn Asn Gly Leu Ala Ser Asn Thr Phe Asn Ser Ser Ser Leu Leu Glu
1               5                   10                  15

Leu Asp Leu Ser Tyr Asn Gln Leu Gln Lys Ile Pro Pro Val Asn Thr
            20                  25                  30

Asn Leu Glu Asn Leu Tyr Leu Gln
        35                  40

<210> SEQ ID NO 62
<211> LENGTH: 51
<212> TYPE: PRT
<213> ORGANISM: Artificial Sequence
<220> FEATURE:
<223> OTHER INFORMATION: Synthetic peptide

<400> SEQUENCE: 62

His Trp Trp Phe His Tyr Leu Arg Ser Gln Gln Ser Thr Tyr Tyr Asp
1               5                   10                  15

Pro Tyr Asp Pro Tyr Pro Tyr Glu Thr Tyr Glu Pro Tyr Pro Tyr Gly
            20                  25                  30

Val Asp Glu Gly Pro Ala Tyr Thr Tyr Gly Ser Pro Ser Pro Pro Asp
        35                  40                  45

Pro Arg Asp
    50

<210> SEQ ID NO 63
<211> LENGTH: 39
<212> TYPE: PRT
<213> ORGANISM: Artificial Sequence
```

```
<220> FEATURE:
<223> OTHER INFORMATION: Synthetic peptide

<400> SEQUENCE: 63

His Asn Ser Leu Thr Asn Asn Gly Leu Ala Ser Asn Thr Phe Asn Ser
1               5                   10                  15

Ser Ser Leu Leu Glu Leu Asp Leu Ser Tyr Asn Gln Leu Gln Lys Ile
                20                  25                  30

Pro Pro Val Asn Thr Asn Leu
            35

<210> SEQ ID NO 64
<211> LENGTH: 112
<212> TYPE: PRT
<213> ORGANISM: Homo sapiens

<400> SEQUENCE: 64

Ala Leu Asp Thr Asn Tyr Cys Phe Ser Thr Glu Lys Asn Cys Cys
1               5                   10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 65
<211> LENGTH: 100
<212> TYPE: PRT
<213> ORGANISM: Homo sapiens

<400> SEQUENCE: 65

Gln Asp Asn Cys Cys Leu Arg Pro Leu Tyr Ile Asp Phe Lys Arg Asp
1               5                   10                  15

Leu Gly Trp Lys Trp Ile His Glu Pro Lys Gly Tyr Asn Ala Asn Phe
                20                  25                  30

Cys Ala Gly Ala Cys Pro Tyr Leu Trp Ser Ser Asp Thr Gln His Arg
            35                  40                  45

Val Leu Ser Leu Tyr Asn Thr Ile Asn Pro Glu Ala Ser Ala Ser Pro
        50                  55                  60

Cys Cys Val Ser Gln Asp Leu Glu Pro Leu Thr Ile Leu Tyr Tyr Ile
65                  70                  75                  80

Gly Lys Thr Pro Lys Ile Glu Gln Leu Ser Asn Met Ile Val Lys Ser
                85                  90                  95

Cys Lys Cys Ser
            100

<210> SEQ ID NO 66
<211> LENGTH: 99
<212> TYPE: PRT
<213> ORGANISM: Homo sapiens

<400> SEQUENCE: 66
```

Asn Cys Cys Val Arg Pro Leu Tyr Ile Asp Phe Arg Gln Asp Leu Gly
1               5                   10                  15

Trp Lys Trp Val His Glu Pro Lys Gly Tyr Tyr Ala Asn Phe Cys Ser
            20                  25                  30

Gly Pro Cys Pro Tyr Leu Arg Ser Ala Asp Thr Thr His Ser Thr Val
        35                  40                  45

Leu Gly Leu Tyr Asn Thr Leu Asn Pro Glu Ala Ser Ala Ser Pro Cys
    50                  55                  60

Cys Val Pro Gln Asp Leu Glu Pro Leu Thr Ile Leu Tyr Tyr Val Gly
65              70                  75                  80

Arg Thr Pro Lys Val Glu Gln Leu Ser Asn Met Val Val Lys Ser Cys
                85                  90                  95

Lys Cys Ser

<210> SEQ ID NO 67
<211> LENGTH: 305
<212> TYPE: PRT
<213> ORGANISM: Homo sapiens
<400> SEQUENCE: 67

Asp Pro Arg Asp Cys Pro Gln Glu Cys Asp Cys Pro Pro Asn Phe Pro
1               5                   10                  15

Thr Ala Met Tyr Cys Asp Asn Arg Asn Leu Lys Tyr Leu Pro Phe Val
            20                  25                  30

Pro Ser Arg Met Lys Tyr Val Tyr Phe Gln Asn Asn Gln Ile Thr Ser
        35                  40                  45

Ile Gln Glu Gly Val Phe Asp Asn Ala Thr Gly Leu Leu Trp Ile Ala
    50                  55                  60

Leu His Gly Asn Gln Ile Thr Ser Asp Lys Val Gly Arg Lys Val Phe
65              70                  75                  80

Ser Lys Leu Arg His Leu Glu Arg Leu Tyr Leu Asp His Asn Asn Leu
                85                  90                  95

Thr Arg Met Pro Gly Pro Leu Pro Arg Ser Leu Arg Glu Leu His Leu
            100                 105                 110

Asp His Asn Gln Ile Ser Arg Val Pro Asn Asn Ala Leu Glu Gly Leu
        115                 120                 125

Glu Asn Leu Thr Ala Leu Tyr Leu Gln His Asn Glu Ile Gln Glu Val
    130                 135                 140

Gly Ser Ser Met Arg Gly Leu Arg Ser Leu Ile Leu Leu Asp Leu Ser
145                 150                 155                 160

Tyr Asn His Leu Arg Lys Val Pro Asp Gly Leu Pro Ser Ala Leu Glu
                165                 170                 175

Gln Leu Tyr Met Glu His Asn Asn Val Tyr Thr Val Pro Asp Ser Tyr
            180                 185                 190

Phe Arg Gly Ala Pro Lys Leu Leu Tyr Val Arg Leu Ser His Asn Ser
        195                 200                 205

Leu Thr Asn Asn Gly Leu Ala Ser Asn Thr Phe Asn Ser Ser Ser Leu
    210                 215                 220

Leu Glu Leu Asp Leu Ser Tyr Asn Gln Leu Gln Lys Ile Pro Pro Val
225                 230                 235                 240

Asn Thr Asn Leu Glu Asn Leu Tyr Leu Gln Gly Asn Arg Ile Asn Glu
                245                 250                 255

Phe Ser Ile Ser Ser Phe Cys Thr Val Val Asp Val Val Asn Phe Ser
            260                 265                 270

```
Lys Leu Gln Val Leu Arg Leu Asp Gly Asn Glu Ile Lys Arg Ser Ala
            275                 280                 285

Met Pro Ala Asp Ala Pro Leu Cys Leu Arg Leu Ala Ser Leu Ile Glu
    290                 295                 300

Ile
305

<210> SEQ ID NO 68
<211> LENGTH: 305
<212> TYPE: PRT
<213> ORGANISM: Bos taurus

<400> SEQUENCE: 68

Gly Pro Val Cys Pro Phe Arg Cys Gln Cys His Leu Arg Val Val Gln
1               5                   10                  15

Cys Ser Asp Leu Gly Leu Glu Lys Val Pro Lys Asp Leu Pro Pro Asp
            20                  25                  30

Thr Ala Leu Leu Asp Leu Gln Asn Asn Lys Ile Thr Glu Ile Lys Asp
        35                  40                  45

Gly Asp Phe Lys Asn Leu Lys Asn Leu His Thr Leu Ile Leu Ile Asn
50                  55                  60

Asn Lys Ile Ser Lys Ile Ser Pro Gly Ala Phe Ala Pro Leu Val Lys
65                  70                  75                  80

Leu Glu Arg Leu Tyr Leu Ser Lys Asn Gln Leu Lys Glu Leu Pro Glu
                85                  90                  95

Lys Met Pro Lys Thr Leu Gln Glu Leu Arg Val His Gly Asn Glu Ile
            100                 105                 110

Thr Lys Val Arg Lys Ser Val Phe Asn Gly Leu Asn Gln Met Ile Val
        115                 120                 125

Val Glu Leu Gly Thr Asn Pro Leu Lys Ser Ser Gly Ile Glu Asn Gly
130                 135                 140

Ala Phe Gln Gly Met Lys Lys Leu Ser Tyr Ile Arg Ile Ala Asp Thr
145                 150                 155                 160

Asn Ile Thr Thr Ile Pro Gln Gly Leu Pro Pro Ser Leu Thr Glu Leu
                165                 170                 175

His Leu Asp Gly Asn Lys Ile Thr Lys Val Asp Ala Ala Ser Leu Lys
            180                 185                 190

Gly Leu Asn Asn Leu Ala Lys Leu Gly Leu Ser Phe Asn Ser Ile Ser
        195                 200                 205

Ala Val Asp Asn Gly Ser Leu Ala Asn Thr Pro His Leu Arg Glu Leu
210                 215                 220

His Leu Asn Asn Asn Lys Leu Val Lys Val Pro Gly Gly Leu Ala Asp
225                 230                 235                 240

His Lys Tyr Ile Gln Val Val Tyr Leu His Asn Asn Asn Ile Ser Ala
                245                 250                 255

Ile Gly Ser Asn Asp Phe Cys Pro Pro Gly Tyr Asn Thr Lys Lys Ala
            260                 265                 270

Ser Tyr Ser Gly Val Ser Leu Phe Ser Asn Pro Val Gln Tyr Trp Glu
        275                 280                 285

Ile Gln Pro Ser Thr Phe Arg Cys Val Tyr Val Arg Ala Ala Val Gln
290                 295                 300

Leu
305
```